United States Patent
Wang et al.

(10) Patent No.: US 10,890,641 B2
(45) Date of Patent: Jan. 12, 2021

(54) SYSTEM AND METHOD OF ROBUST QUANTITATIVE SUSCEPTIBILITY MAPPING

(71) Applicant: CORNELL UNIVERSITY, Ithaca, NY (US)

(72) Inventors: Yi Wang, New York, NY (US); Zhe Liu, New York, NY (US); Youngwook Kee, New York, NY (US); Alexey Dimov, New York, NY (US); Yan Wen, New York, NY (US); Jingwei Zhang, Woodside, NY (US); Pascal Spincemaille, New York, NY (US)

(73) Assignee: Cornell University, Ithaca, NY (US)

( * ) Notice: Subject to any disclaimer, the term of this patent is extended or adjusted under 35 U.S.C. 154(b) by 170 days.

(21) Appl. No.: 15/943,753

(22) Filed: Apr. 3, 2018

(65) Prior Publication Data
US 2018/0321347 A1 Nov. 8, 2018

Related U.S. Application Data

(60) Provisional application No. 62/482,864, filed on Apr. 7, 2017.

(51) Int. Cl.
*G06K 9/00* (2006.01)
*G01R 33/56* (2006.01)
(Continued)

(52) U.S. Cl.
CPC ........ *G01R 33/5608* (2013.01); *A61B 5/0042* (2013.01); *A61B 5/0263* (2013.01);
(Continued)

(58) Field of Classification Search
None
See application file for complete search history.

(56) References Cited

U.S. PATENT DOCUMENTS 8,781,197 B2    7/2014   Wang et al.
9,213,076 B2 * 12/2015   Liu .................. G01R 33/56545
(Continued)

OTHER PUBLICATIONS

Dong et al., Simultaneous phase unwrapping and removal of chemical shift (SPURS) using graph cuts: application in quantitative susceptibility mapping, IEEE Transactions on Medical Imaging, vol. 34, No. 2, Feb. 2015 (Year: 2015).*

(Continued)

*Primary Examiner* — Soo Jin Park
(74) *Attorney, Agent, or Firm* — Scully Scott Murphy & Presser

(57) ABSTRACT

Exemplary quantitative susceptibility mapping methods, systems and computer-accessible medium can be provided to generate images of tissue magnetism property from complex magnetic resonance imaging data using the Bayesian inference approach, which minimizes a cost function consisting of a data fidelity term and two regularization terms. The data fidelity term is constructed directly from the complex magnetic resonance imaging data. The first prior is constructed from matching structures or information content in known morphology. The second prior is constructed from a region having an approximately homogenous and known susceptibility value and a characteristic feature on anatomic images. The quantitative susceptibility map can be determined by minimizing the cost function. Thus, according to the exemplary embodiment, system, method and computer-accessible medium can be provided for determining magnetic susceptibility information associated with at least one structure.

20 Claims, 50 Drawing Sheets

(51) Int. Cl.
  A61B 5/055   (2006.01)
  G01R 33/565  (2006.01)
  G01R 33/24   (2006.01)
  A61B 5/026   (2006.01)
  A61B 5/00    (2006.01)
  G01R 33/50   (2006.01)
  G01R 33/48   (2006.01)
  A61B 5/145   (2006.01)

(52) U.S. Cl.
  CPC ............ *A61B 5/055* (2013.01); *A61B 5/7203* (2013.01); *G01R 33/24* (2013.01); *G01R 33/56527* (2013.01); A61B 5/0035 (2013.01); A61B 5/14542 (2013.01); A61B 5/4082 (2013.01); A61B 5/4088 (2013.01); A61B 5/4504 (2013.01); A61B 5/4872 (2013.01); G01R 33/4828 (2013.01); G01R 33/50 (2013.01); G01R 33/5602 (2013.01); G01R 33/56536 (2013.01)

(56) References Cited

U.S. PATENT DOCUMENTS

| | | | | |
|---|---|---|---|---|
| 9,612,300 | B2* | 4/2017 | Sharma | G01R 33/243 |
| 9,943,246 | B2* | 4/2018 | Reeder | A61B 5/055 |
| 2011/0044524 | A1* | 2/2011 | Wang | G01R 33/54 |
| | | | | 382/131 |
| 2013/0221961 | A1* | 8/2013 | Liu | G01R 33/56545 |
| | | | | 324/307 |
| 2018/0310869 | A1* | 11/2018 | Yablonskiy | A61B 5/055 |
| 2019/0261906 | A1* | 8/2019 | Shirai | G01R 33/5602 |

OTHER PUBLICATIONS

Hernando et al., "Magnetic susceptibility as a B0 field strength independent MRI biomarker of liver iron overload", Magnetic Resonance in Medicine 70:648-656 (2013) (Year: 2013).*

Cho J. et al., "Cerebral Metabolic Rate of Oxygen (CMRO2) Mapping by Combining Quantitative Susceptibility Mapping (QSM) and Quantitative Blood Oxygenation Level-Dependent Imaging (qBOLD)", Magnetic Resonance in Medicine, pp. 1-10 (Jan. 2018).

Dimov A.V. et al., "Bone Quantitative Susceptibility Mapping Using a Chemical Species-Specific R2 Signal Model With Ultra-short and Conventional Echo Data", Magnetic Resonance in Medicine 79:121-128 (2018).

Kee Y. et al., "Coherence Enhancement in Quantitative Susceptibility Mapping by Means of Anisotropic Weighting in Morphology Enabled Dipole Inversion", Magnetic Resonance in Medicine 79:1172-1180 (2018).

Kee Y. et al., "Primal-Dual and Forward Gradient Implementation for Quantitative Susceptibility Mapping", Magnetic Resonance in Medicine 78:2416-2427 (2017).

Li, Ph.D. J. et al., "Quantitative Susceptibility Mapping (QSM) Minimizes Interference from Cellular Pathology in R2 Estimation of Liver Iron Concentration", Journal of Magnetic Resonance Imaging, pp. 1-11 (Mar. 2018).

Liu Z. et al., "MEDI+0 Morphology Enabled Dipole Inversion With Automatic Uniform Cerebrospinal Fluid Zero Reference for Quantitative Susceptibility Mapping", Magnetic Resonance in Medicine 79:2795-2803 (2018).

Liu Z. et al., "Preconditioned Total Field Inversion (TFI) Method for Quantitative Susceptibility Mapping", Magnetic Resonance in Medicine 78:303-315 (2017).

Wen Y. et al., "Cardiac Quantitative Susceptibility Mapping (QSM) for Heart Chamber Oxygenation", Magnetic Resonance in Medicine 79:1545-1552 (2018).

Zhang J. et al., "Quantitative Susceptibility Mapping-Based Cerebral Metabolic Rate of Oxygen Mapping With Minimum Local Variance", Magnetic Resonance in Medicine 79:172-179 (2018).

* cited by examiner a b

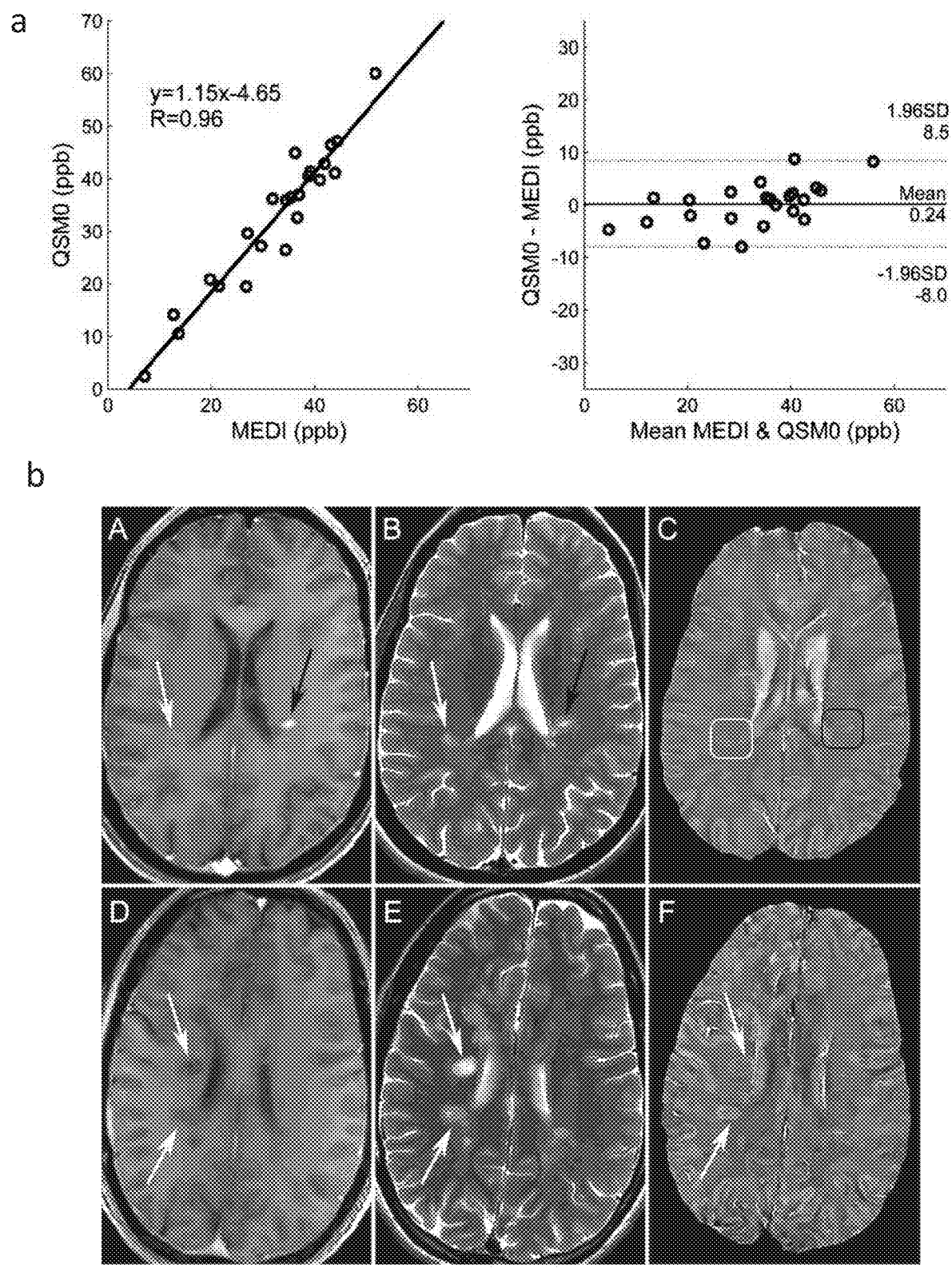
FIG.24 a & b

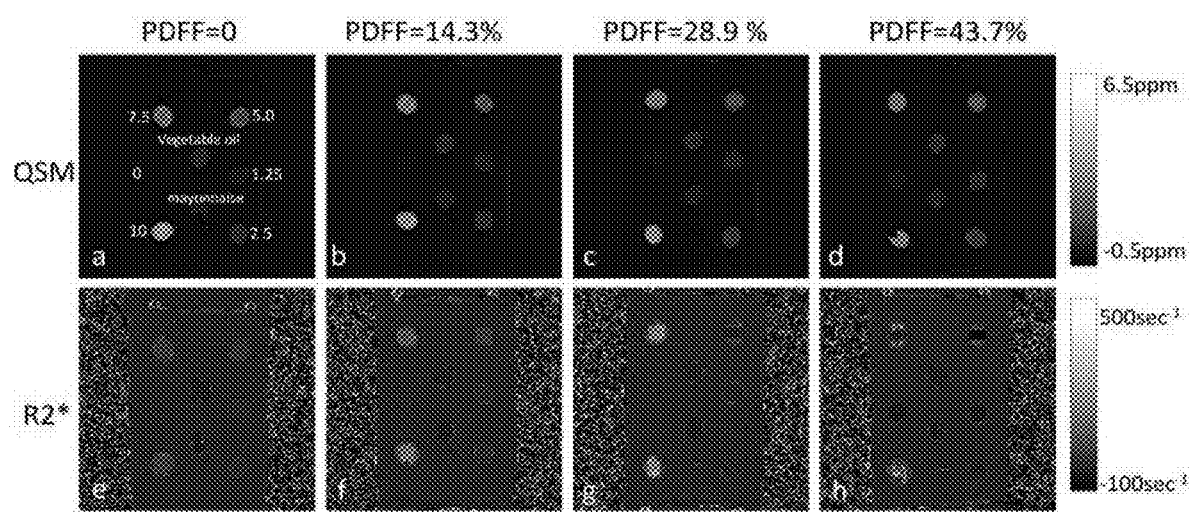
FIG. 25 a – h

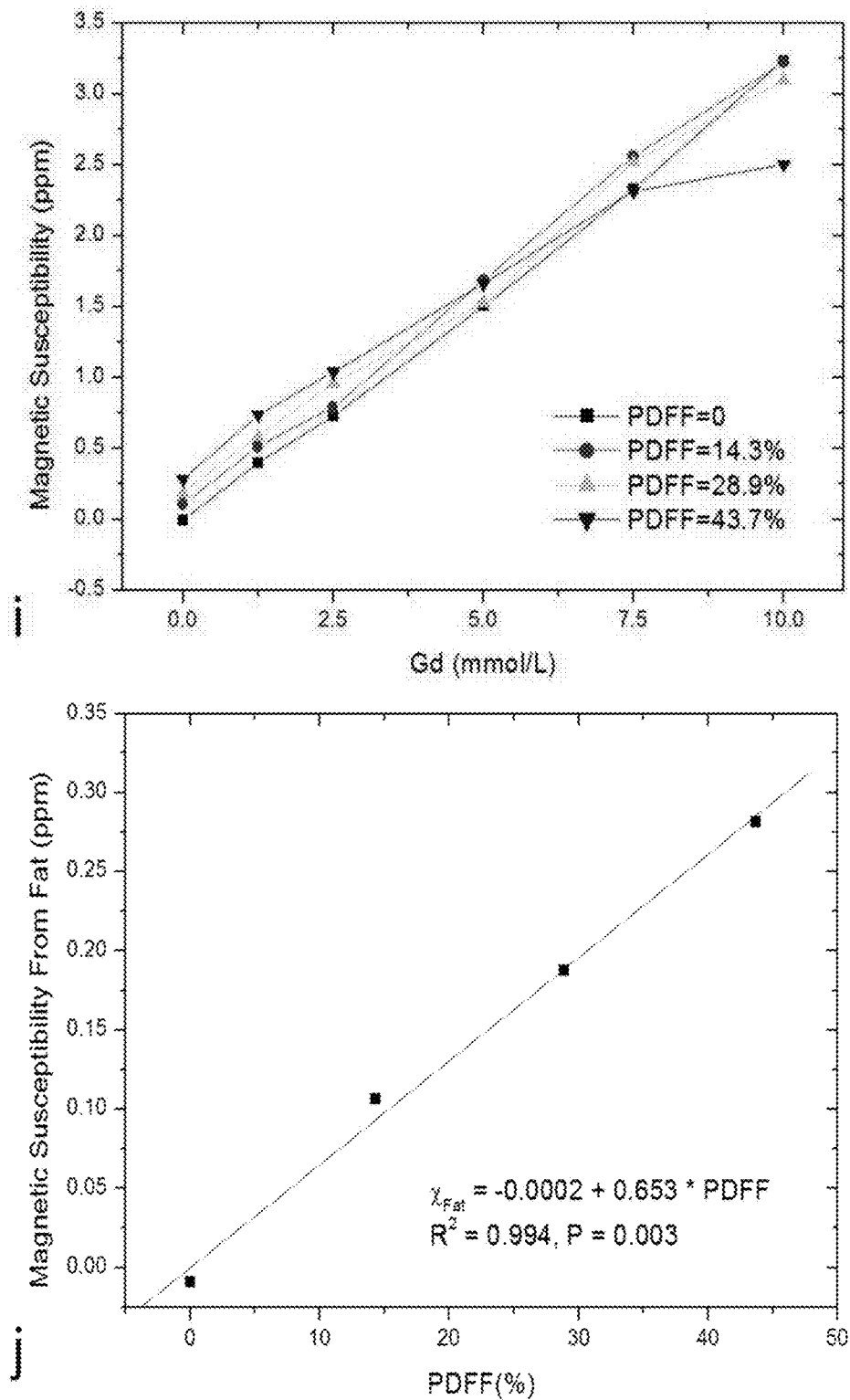
FIG.25 i & j

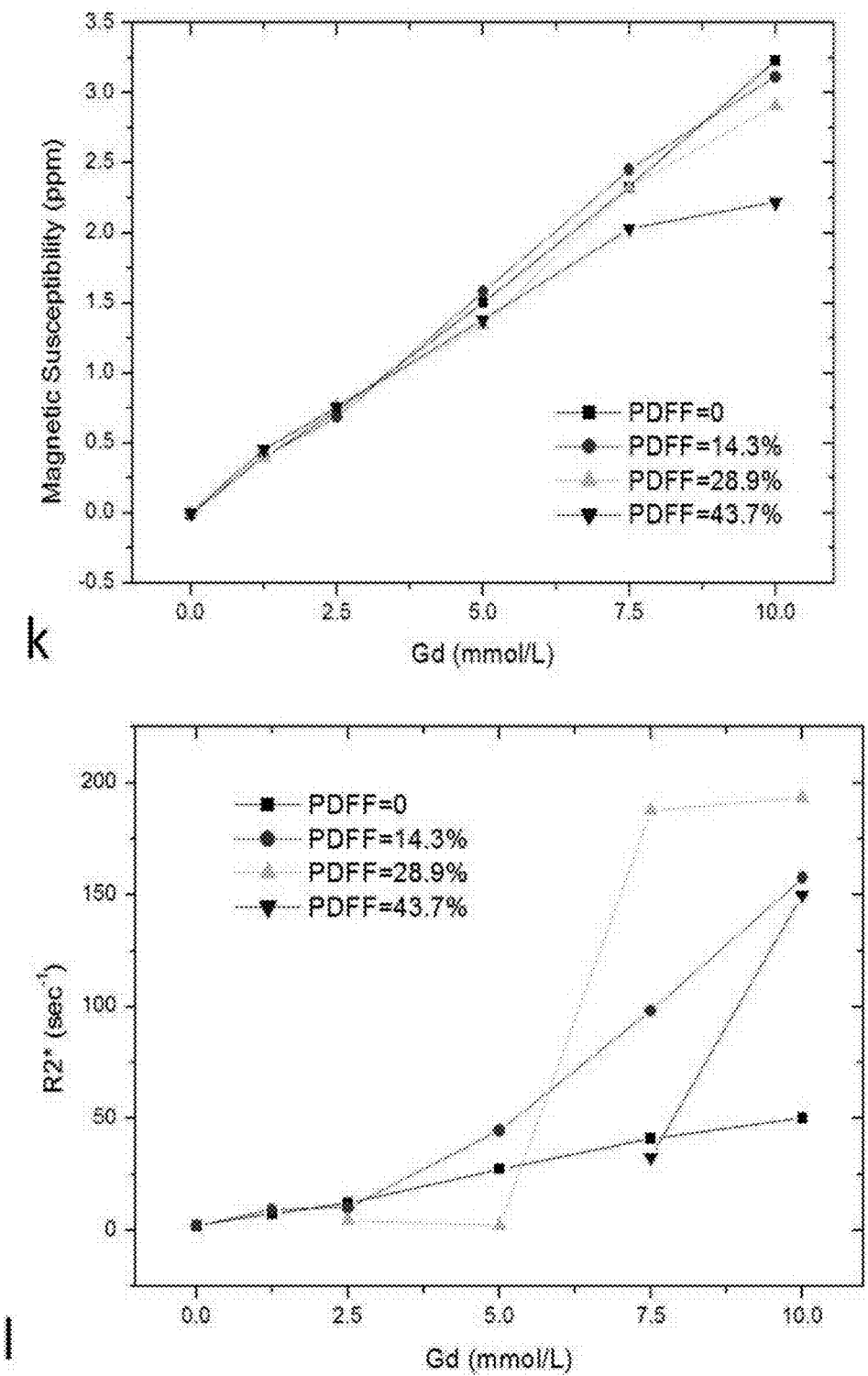
FIG.25 k & l

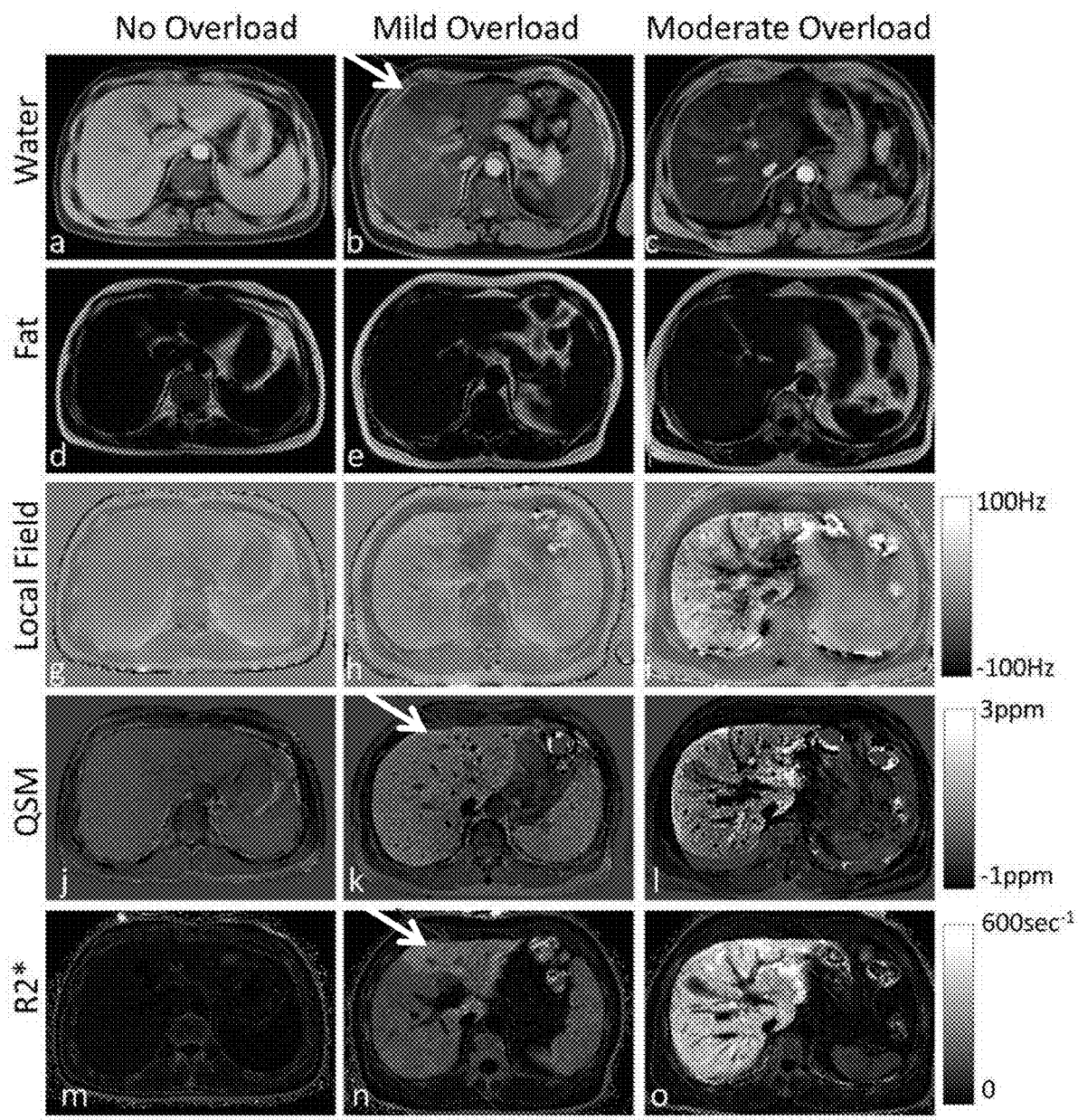
FIG.30 a – o

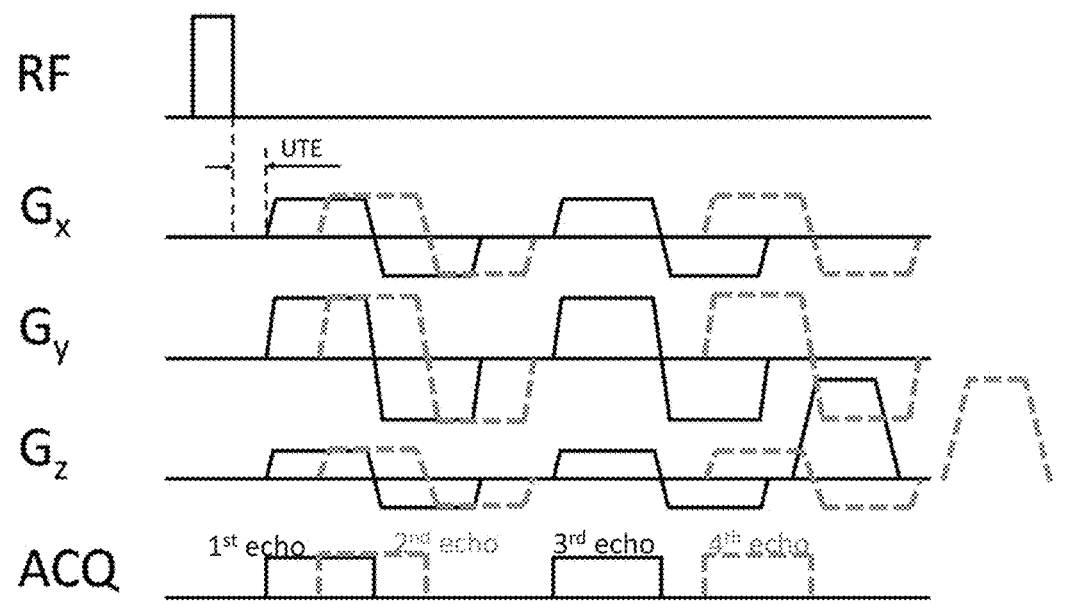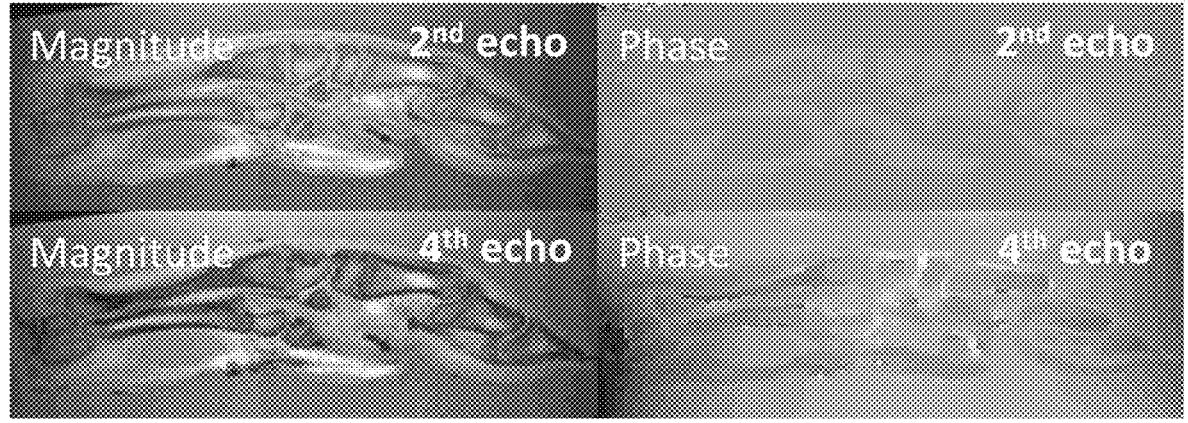
FIG.32

SYSTEM AND METHOD OF ROBUST QUANTITATIVE SUSCEPTIBILITY MAPPING

CROSS REFERENCE TO RELATED APPLICATIONS

This application claims priority from U.S. Provisional Application No. 62/482,864, filed Apr. 7, 2017, the entire contents of which are incorporated herein by reference.

STATEMENT REGARDING FEDERALLY SPONSORED RESEARCH AND DEVELOPMENT

This invention was made with government support under Grant No. NS072370, NS090464, NS095562 and CA181566 awarded by the National Institutes of Health. The government has certain rights in this invention.

TECHNICAL FIELD

This invention relates to magnetic resonance imaging, and more particularly to quantitatively mapping material intrinsic physical properties using signals collected in magnetic resonance imaging.

BACKGROUND

Quantitative susceptibility mapping (QSM) in magnetic resonance imaging (MRI) has received increasing clinical and scientific interest. QSM has shown promise in characterizing and quantifying chemical compositions such as iron, calcium, and contrast agents including gadolinium and superparamagnetic iron oxide (SPIO) nanoparticles. Tissue composition of these compounds may be altered in various neurological disorders, such as Parkinson's disease, Alzheimer's disease, stroke, multiple sclerosis, hemochromatosis, and tumor as well as other disease throughout the body. QSM is able to unravel novel information related to the magnetic susceptibility (or simply referred as susceptibility), a physical property of underlying tissue. Due to the prevalence of iron and calcium in living organisms, their active involvement in vital cellular functions, their important roles in the musculoskeletal system, QSM is in general very useful to study the molecular biology of iron/calcium by tracking iron in the circulation system and the metabolic activities by using iron and calcium as surrogate marks. Therefore, accurate mapping of the magnetic susceptibility induced by iron, calcium and contrast agents will provide tremendous benefit to clinical researchers to probe the structure and functions of human body, and to clinicians to better diagnose various diseases and provide relevant treatment.

SUMMARY

Implementations of systems and methods for collecting and processing MRI signals of a subject, and reconstructing maps of physical properties intrinsic to the subject (e.g., magnetic susceptibility) are described below. In some implementations, MR signal data corresponding to a subject can be transformed into susceptibility-based images that quantitatively depict the structure and/or composition and/or function of the subject. Using this quantitative susceptibility map, one or more susceptibility-based images of the subject can be generated and displayed to a user. The user can then use these images for diagnostic or experimental purposes, for example to investigate the structure and/or composition and/or function of the subject, and/or to diagnose and/or treat various conditions or diseases based, at least in part, on the images. As one or more of the described implementations can result in susceptibility-based images having higher quality and/or accuracy compared to other susceptibility mapping techniques, at least some of these implementations can be used to improve a user's understanding of a subject's structure and/or composition and/or function, and can be used to improve the accuracy of any resulting medical diagnoses or experimental analyses.

Some of the implementations described below can be used to evaluate the magnetic dipole inversion while allowing incorporation of preconditioning, anisotropic weighting, primal dual solver, chemical composition based fat compensation, and enforcement of regional known near-constant susceptibility is disclosed to improve susceptibility map quality including suppression of artificial signal variation in homogenous regions and to provide absolute susceptibility values, which are pressing concerns to ensure quantification accuracy, experimental repeatability and reproducibility.

In general, one aspect of the invention disclosed here enables an absolute quantification of tissue magnetic susceptibility by referencing to a region of tissue with known homogenous susceptibility, such as zero susceptibility for cerebrospinal fluid (CSF) in the brain and fully oxygenated aorta in the body. This aspect of invention solves the practical problem of zero-reference in longitudinal and cross-center studies and in studies requiring absolute quantifications. The invention disclosed here also enables reduction of shadow artifacts caused by field data that are not compatible with the dipole field model, in addition to reducing streaking artifacts caused by granular noise in data.

In general, another aspect of the invention disclosed here enables accurate tissue structure matching using an orientation dependent L1 norm and a primal-dual computation of its derivative in numerical searching for the best match. The disclosed preconditioned total field inversion method bypasses the background field removal step, the robustness of which may be affected by phase unwrapping, skull stripping, and boundary conditions.

In general, another aspect of the invention disclosed here enables accurate imaging methods to quantify liver iron by correcting for effects from fat, fibrosis and edema that confound traditional T2 and T2* methods, to quantify cerebral metabolic rate of oxygen consumption by incorporating cerebral blood flow information, to quantify bone mineralization and other calcifications in the body, and to quantify chamber blood oxygenation level and intramyocardial hemorrhage in the heart.

Implementations of these aspects may include one or more of the following features.

In some implementations, the cerebrospinal fluid in the ventricles in the brain is segmented based on low R2* values by applying R2* thresholding and connectivity.

In some implementations, the prior information regarding the magnetic susceptibility distribution is determined based on an L1 norm and structural information of the object estimated from acquired images of the object.

In some implementations, the object comprises a cortex, a putamen, a globus pallidus, a red nucleus, a substantia nigra, or a subthalamic nucleus of a brain, or a liver in an abdomen, and generating one or more images of the object comprises generating one or more images depicting the cortex, the putamen, the globus pallidus, the red nucleus, the substantia nigra, or the subthalamic nucleus of the brain, or the liver in the abdomen.

In some implementations, the object comprises at least one of a multiple sclerosis lesion, a cancerous lesion, a calcified lesion, or a hemorrhage, and generating one or more images of the object comprises generating one or more images depicting at least one of the multiple sclerosis lesion, the cancerous lesion, the calcified lesion, or the hemorrhage.

In some implementations, the operations further comprise of quantifying, based on the one or more images, a distribution of contrast agents introduced into the object in the course of a contrast enhanced magnetic resonance imaging procedure.

In some implementations, tissue chemical composition is fat and water, and the magnetic field, the water fraction and the fat fraction in a voxel are computed iteratively from the complex Mill data using an appropriate initialization.

The details of one or more embodiments are set forth in the accompanying drawings and the description below. Other features and advantages will be apparent from the description and drawings, and from the claims.

DESCRIPTION OF DRAWINGS

FIGS. 11a-11b. Computed susceptibility map. (a) Cornell MRI research lab data ($\lambda/2=1000$); and (b) QSM 2016 reconstruction challenge data ($\lambda/2=235$). The first, second, and last columns from the left are axial, sagittal, and coronal views, respectively. Streaking artifacts manifested as spurious dots in axial view, and streaks in sagittal and coronal views were substantially suppressed in anisotropic weighting. These can be seen across the images (globally). Arrows were also placed where the artifacts are conspicuous. Note that the artifacts are seen more clearly once images are zoomed in.

FIGS. 25a-25l. Measured susceptibility and R2* maps from fat-water-Gadolinium phantoms. a-d: measured susceptibility maps; c-h: measured R2* maps; i: measured solution total susceptibility values versus varying Gd concentrations; j: Fat contribution (measured at vials of zero Gd) to solution total susceptibility versus varying fat concentrations; k: fat-corrected susceptibility values vs Gd concentration; l: measured R2* values versus varying Gd concentrations. PDFF, proton-density fat-fraction.

FIG. 32. Top: Dual echo gradient echo acquisition for acquiring one ultra-short echo and one conventional echo image. Both echoes are shifted between successive TRs to acquire four unique echo time values (echoes acquired in the same TR are shown using the same line type). Images below compare magnitudes and phases of two of the acquired echoes (phase of the first echo is set to zero during coil combination to eliminate phase offsets of different channels).

Like reference symbols in the various drawings indicate like elements.

DETAILED DESCRIPTION

Figures 1A, 1B, 1C, 1D, 1E, 1F, 1G, 1H, 1I:
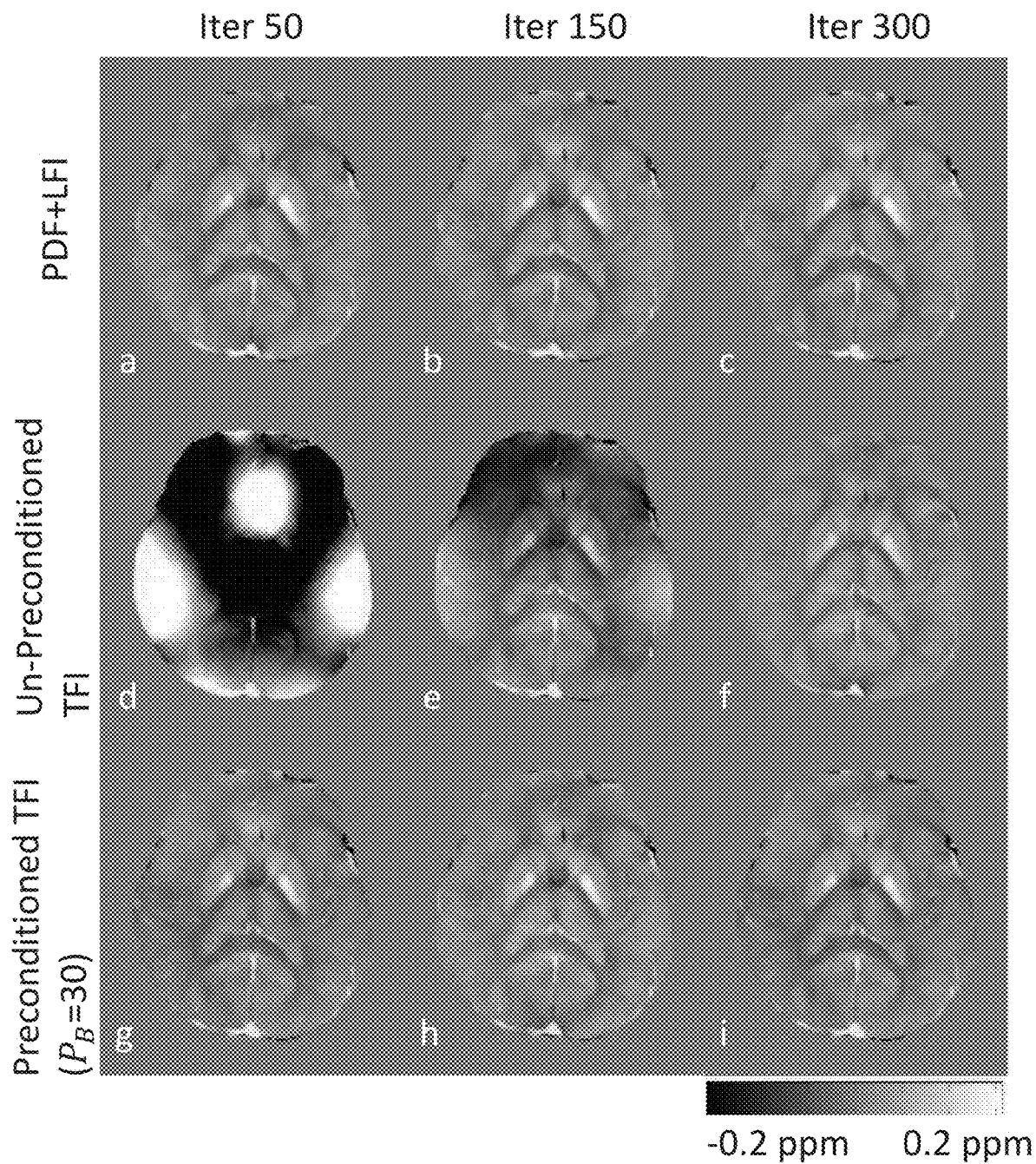
FIGS. 1a-1i show a human brain QSM reconstructed using traditional PDF+LFI, un-preconditioned TFI, and preconditioned TFI at different CG iterations (Iter). In order to produce a QSM similar to PDF+LFI with 50 iterations, TFI without preconditioning required 300 iterations, Preconditioning reduces this number down to 50.

Implementations of systems and methods for collecting and processing MRI signals of a subject, and reconstructing maps of physical properties intrinsic to the subject (e.g., magnetic susceptibility) are described below. Some of the disclosed implementations overcome limitations in quantitative susceptibility mapping (QSM), where the computation speed and accuracy and the Bayesian prior information affect QSM image quality and practical usage. In some implementations, to reconstruct maps of a subject's magnetic susceptibility, the iterative computation process of finding the susceptibility distribution that optimally fit available field data and tissue structure prior information is accelerated using preconditioning and primal dual optimization method and is computed more accurately using primal dual optimization method. In some implementations, the tissue structure prior information in a Bayesian method for estimating susceptibility is improved using anisotropic edge weighting and using additional information of the near-zero susceptibility of the cerebrospinal fluid (CSF) in the lateral ventricles that can be automatically segmented from the brain image. Implementations of these improvements have made QSM technology robust and accurate, extending QSM usage from the brain to including the skull, bone, heart and liver, and to quantification of deoxyheme associated with aerobic energy metabolism.

QSM is based on minimizing a cost function that fits the measured tissue magnetic field b (r) (in unit B0) to the dipole field $$d(r) = \frac{2z^2 - x^2 - y^2}{4\pi|r|^5}.$$

Approximating noise in b as Gaussian, the data fidelity term is $$\int_{\mathbb{R}^3} w(r)|d^*\chi(r)-b(r)|^2 dr \equiv \|d-\chi-b\|_w^2 \quad [1]$$

This integral form b=d*χ allows numerical estimation of the susceptibility solution, typically under a regularization associated with a prior information. As known from physics of Maxwell equation, the integral form may represent a solution to the governing partial differential equation (PDE). For mathematical analysis of susceptibility solution, the equivalent PDE that can be derived directly from Maxwell's equation with Lorentz sphere correction offers useful insights:

$$(\partial_z^2 - (\partial_x^2 + \partial_y^2)^{1/2})\chi = -3/2\Delta b. \quad [2]$$

Eq.2 is a wave equation with respect to susceptibility χ (z-axis is time) and a Laplacian equation with respect to field b. In the continuous space without any error with b(r)=d*χ(r), B(k)=D(k)χ(k), a precise solution of no streaking can be obtained: $\chi = \lim_{\epsilon \searrow 0} \mathcal{F}^{-1}((1-\eta_\epsilon)(B/D))$. $\eta_\epsilon=1$ if $D(k)<\epsilon/2$ otherwise 0. Any field data that cannot be fitted to the dipole field is referred as the incompatible field data v(r), which may come from various causes including noise, digitiztion error, and anisotropy source. This incompatible field causes artifacts according to the wave propagation solution:

$$\chi_V(r) = \int \frac{-\frac{3}{2}\Delta'v(r')}{2\pi\sqrt{(z-z')^2 - 2((x-x')^2 + (y-y')^2)}} dr', \quad [3]$$

$$(z-z')^2 > 2((x-x')^2 + (y-y')^2).$$

Here $\frac{1}{2\pi\sqrt{(z-z')^2 - 2((x-x')^2 + (y-y')^2)}}$ is the wave propagator having large values at magic-angle cones above and below the incompatible source −3/2Δ'v(r'). The dipole incompatible part, including noise, discretization error, and anisotropy sources, generates artifacts defined by the wave propagator with the B0 field direction as the time axis. Granular noise causes streaking and contiguous error causes both streaking and shadow artifacts.

The invention described here makes use of the above mathematical fact to improve QSM speed and accuracy. Streaking artifacts are characterized by edges along the magic angle (54.7°) in k-space or the complimentary magic angle in image space, which are almost completely distinct from tissue edges. Accordingly, they can be can be minimized during numerical optimization by a regularization term based upon tissue structure information to identify solution of no streaking, which is the morphology enable dipole inversion (MEDI) approach. Tissue structure information is numerically evaluated using edge gradient and L1 norm. This calculation was previously performed by approximating the derivative of L1 norm as a continuous function and by ignoring the edge gradient direction. This approximation can be improved in terms of both accuracy and speed using the primal dual optimization method and using anisotropic weighting according to edge gradient direction.

Shadow artifacts have low spatial frequency contents, which can be minimized accordingly by incorporating cost function terms of low spatial frequencies. Additionally, penalty terms can be formulated using specific tissue structure and shadow structure information. One specific tissue structure is that CSF in the ventricles of the brain is almost pure water with very little cellular contents. Therefore, ventricular susceptibility map should be nearly uniform, and any deviation from uniformity should be regarded as shadow artifacts to be penalized during numerical optimization by incorporating a regularization term. One specific shadow structure information is that shadow generated by smoothly distributed error source over a large region, such as white matter anisotropic component, which is strong above and below the region, spreads cross the whole region, and consists of components of low spatial frequencies. Therefore, the shadow artifacts can be penalized during numerical optimization using a $k^2$ weighting (Laplacian operation) as a preconditioner to avoid low spatial frequency in Krylov space, or using a regularization term imposing costs on low spatial frequencies with corresponding long spatial wavelengths such as object size and half object size and a cost function associated with an estimated white matter anisotropic contribution. In another implementation, the white matter anisotropy effect modeled according to a brain atlas as a dipole-incompatible part is tuned such that the CSF susceptibility in the segmented ventricle region is uniform, which at the same time minimizing shadow artifacts in the brain QSM.

The iteration for finding the optimal susceptibility distribution according to available field data and tissue prior information can be hugely accelerated using preconditioning. This is particularly beneficial for searching in a large range of possible susceptibility values. As a result, the improvement in QSM system and method described in this invention enables fast, accurate and robust QSM, which improves applications in the brain and enables applications in other organs outside the brain.

Robust QSM improves upon many applications, including brain QSM with reduced shadow and streaking artifacts and with uniform ventricle CSF as an automatic and consistent zero reference, whole brain QSM without skull stripping and bone mineralization where bone diamagnetic susceptibility being proportional to CT attenuation coefficients can be used for positron emission tomography attenuation correction, liver iron content mapping without R2/R2* confounding errors, mapping cerebral metabolic rate of oxygen consumption, mapping susceptibility sources in the heart including oxygenation level and intramyocardial hemorrhage, and mapping susceptibility sources in vessel wall plaque differentiating intraplaque hemorrhage from plaque calcification.

1. Preconditioned Total Field Inversion for QSM

In this section, we describe a QSM improvement that uses preconditioning to speed up the convergence of QSM, allowing integration of background field removal and tissue field inversion.

1.1. Introduction

Quantitative susceptibility mapping (QSM) extracts the spatial distribution of tissue magnetic susceptibility from the gradient echo signal phase. Current QSM methods consist of two steps: i) background field removal to determine the local field generated by tissue, and ii) inversion from the local field to the tissue susceptibility. This allows a fairly robust mapping of the central brain regions, particularly for iron deposition in the mid brain nuclei. However, several technical challenges remain.

A major challenge is imprecise separation of background and tissue fields caused by the assumptions made in background field removal methods. This is particularly problematic near the brain boundary where a large tissue-air susceptibility difference is present. To avoid the separate fitting of background and local field, Laplacian-based QSM methods have been proposed based on the partial differential formulation of the forward signal equation. The Laplacian operation implicitly eliminates the background field. However, the practical implementation of the Laplacian requires a trade-off between robustness to error amplification and the integrity of the visualized cortical brain tissue. The necessary erosion of the brain mask may prevent visualization of certain structures at the brain boundary, such as the superior sagittal sinus.

The presence of a large susceptibility dynamic range within the region of interest (ROI) is similarly a challenge in QSM, often leading to streaking artifacts. For example, the susceptibility difference between intracerebral hemorrhage (ICH) and surrounding tissue can exceed 1.6 ppm. Using a nonlinear QSM model of ICH signal can reduce these streaking artifacts, but does not eliminate them. Recent work has focused on this challenge by separating the fitting processes for sources of strong (such as ICH) and weak (normal brain) susceptibilities, hence preventing ICH-related artifact from permeating into the normal brain. However, these methods require carefully choosing the regularization parameter or threshold for detecting ICH to minimize artifacts in the subsequent inversion for weak susceptibilities.

In this work, we address both challenges using a generalized inverse problem that is suitable for large dynamic ranges in susceptibility. We propose a preconditioned QSM to perform total field inversion (TFI), strongly reducing the error propagation associated with imprecise background field removal, and suppressing streaking artifacts in intracerebral hemorrhage QSM.

1.2. Theory

For QSM, the total magnetic field is conventionally decomposed into two components: the local field $f_L$ defined as the magnetic field generated by the susceptibility $\chi_L$ inside a given region of interest M (local susceptibility), and the background field $f_B$ defined as the magnetic field generated by the susceptibility $X_B$ outside M (background susceptibility):

$$f = f_B + f_L = d * (\chi_B + \chi_L) \qquad [4]$$

Here * is the convolution operator, and d is the the field generated by a unit dipole with Lorentz sphere correction. The components $f_B$ and $f_L$ may be estimated separately: estimation of $\chi_B$ or $f_B$ is referred to as background field removal. A variety of background field removal methods have been proposed, such as high-pass filtering (HPF), projection onto dipole fields (PDF) or Laplacian based methods: $\chi_L$ is then obtained from the local field $f - f_B$, typically using regularization. This step is referred to as local field inversion (LFI). Errors in the background field propagate into the subsequent local field, ultimately leading to errors in the final susceptibility. Although recent work allows updating the background field during local field inversion, it requires a prior susceptibility atlas and co-registration to estimate the background susceptibility first.

Here, we propose to estimate $\chi_B$ and $\chi_L$ jointly using a total field inversion (TFI):

$$\chi^* = \operatorname{argmin}_\chi \tfrac{1}{2}\|w(f - d^*\chi)\|_2^2 + \lambda\|M_G\nabla\chi\|_1 \quad [5]$$

thus using the same formulation as the traditional QSM inversion problem. Here $\chi = \chi_L + \chi_B$ represents the total susceptibility in the entire image volume. The data weighting w can be derived from the magnitude images by calculating the error propagation from the MRI data into the total field. A weighted total variation term is used to suppress the streaking artifacts induced by the presence of zeroes in the dipole kernel d.

The use of iterative optimization algorithms, such as conjugate gradient (CG), in solving Eq. 5 can lead to slow convergence, as illustrated in a healthy brain in FIGS. 1a-1i. Here, Eq. 5 is linearized at $\chi=0$ and solved using CG. During early iterations, part of the background field is fitted as local field, generating an unreasonable local susceptibility map (FIG. 1d). To address this problem, we use prior-enhanced preconditioning to improve convergence. If the solution $\chi$ is a Gaussian random vector with mean $0 \in \mathbb{R}^n$ and covariance matrix $\Gamma \in \mathbb{R}^{n \times n}$, then a right-hand preconditioner P (see below) that approximates the covariance matrix $\Gamma$, or $P^H P \approx \Gamma$, will increase convergence speed. For TFI, a binary diagonal preconditioner P is constructed as follows:

$$P_i = \begin{cases} 1, & i \in M \\ P_B(P_B > 1), & i \notin M \end{cases}, \quad [6]$$

where i denotes the voxel, and M the tissue ROI. It is designed such that the difference in the matrix $P^H P$ between a voxel outside and inside M is approximately equal to the difference in susceptibility between the local and the background region, which includes bone and air. We further modify this P to account for strong susceptibility within M (e.g. intracerebral hemorrhage) by thresholding the R2* map: $M_{R2^*} := R2^* < R2_{th}^*$, assuming that voxels with high R2* have strong susceptibility. Thus, P is defined as:

$$P_i = \begin{cases} 1, & i \in M \cap M_{R2^*} \\ P_B(P_B > 1), & \text{otherwise} \end{cases} \quad [7]$$

The preconditioned TFI problem then becomes:

$$y^* = \operatorname{argmin}_y \Phi(y) = \operatorname{argmin}_y \tfrac{1}{2}\|w(f - d*Py)\|_2^2 + \lambda\|M_G\nabla Py\|_1 \quad [8]$$

The final susceptibility is computed as $\chi^* = Py^*$. Eq. 8 is solved using a Gauss-Newton method as follows:

$$y^* = \operatorname{argmin}_y \Phi(y) = \operatorname{argmin}_y \tfrac{1}{2}\|W(f - F^H DFPy)\|_2^2 + \lambda\|M_G GPy\|_1$$

Where F is the Fourier transform, $$D(k) = \frac{1}{3} - \frac{k_z^2}{k^2}$$

is the k-space dipole kernel and G the finite difference operator. At the n-th Newton iteration, $\Phi$ is linearized at the current solution $y_n$:

$$\Phi(y_n + dy_n) = \tfrac{1}{2}\|W((f - F^H DFPy_n) - F^H DFPdy_n)\|_2^2 + \lambda\|M_G GP(y_n + dy_n)\|_1$$

Using weak derivatives, the update $dy_n$ is found by solving:

$$0 = \nabla_{dy_n}\Phi = -(WF^H DFP)^H W((f - F^H DFPy_n) - F^H DFPdy_n) + \lambda(M_G GP)^H \operatorname{diag}\left\{\frac{1}{\sqrt{|M_G GPy_n|^2 + \epsilon}}\right\} M_G GP(y_n + dy_n)$$

Or:

$$\left[PF^H DFW^2 F^H DFP + \lambda PG^H M_G \operatorname{diag}\left\{\frac{1}{\sqrt{|M_G GPy_n|^2 + \epsilon}}\right\} M_G GP\right] dy_n =$$

$$\left[PF^H DFW^2(f - F^H DFPy_n) - \lambda PG^H M_G \operatorname{diag}\left\{\frac{1}{\sqrt{|M_G GPy_n|^2 + \epsilon}}\right\} MGPy_n\right],$$

which is solved using the conjugate gradient (CG) method. Note that we use $M_G GPy_n \approx \sqrt{|M_G GPy_n|^2 + \epsilon}$ where $\epsilon = 10^{-6}$ to avoid division by zero. The stopping criteria are: maximum number of iterations=100 or relative residual<0.01. The Gauss-Newton method is terminated when the relative update $\|dy_n\|_2/\|y_n\|_2$ is smaller than 0.01.

A number of recently proposed methods similarly circumvent background field removal to estimate susceptibility directly from the total field. These methods are based on the partial differential formulation of the signal equation (Eq. 4):

$$\Delta f = \Delta(d*(\chi_B + \chi_L)) = \left(\frac{1}{3}\Delta - \frac{\partial^2}{\partial z^2}\right)\chi_L \quad [9]$$

Here, $\Delta$ denotes the Laplacian. Notice that the contribution from background sources $\chi_B$ disappears after applying the Laplacian. Two examples of these methods are:

i) Single-Step QSM (SSQSM):

$$\chi^* = \operatorname{argmin}_\chi \tfrac{1}{2}\left\|\Delta f - \left(\tfrac{1}{3}\Delta - \frac{\partial^2}{\partial z^2}\right)\chi\right\|_2^2 + \lambda\|M_G\nabla\chi\|_2^2, \quad [10]$$

where $M_G$ is a binary mask derived from the magnitude image. It can be efficiently optimized using a preconditioned conjugate gradient solver.

ii) Differential QSM:

$$\chi^* = \operatorname{argmin}_\chi \tfrac{1}{2}\|w(e^{-iGMLf} - e^{-iGMP\chi})\|_2^2 + \lambda\|M_G\nabla\chi\|_1 \quad \text{with} \quad [11]$$

$$GMLf(r) \stackrel{def}{=} \int_M \frac{1}{|r - r'|}\Delta f(r')dr' \quad \text{and}$$

$$GMP\chi(r) \stackrel{def}{=} \int_M \frac{1}{|r - r'|}\left(\tfrac{1}{3}\Delta - \partial 2\partial z2\chi(r')\right)dr'.$$

Laplacian-based methods enable QSM reconstruction within a single step. However, the practical implementation of Laplacian necessitates the erosion of the ROI M. The amount of erosion depends on the width of the kernel used for computing the Laplacian.

1.3. Materials and Methods

For developing and evaluating the proposed total field inversion (TFI) with preconditioning, we performed simulations, phantom imaging, in vivo imaging of the brain of healthy subjects using COSMOS as a reference and of patients suffering from hemorrhages. Finally, we explored whole brain QSM. The optimal $P_B$ in Eq. 7 was empirically determined to ensure that, for a given number of CG iterations, the Gauss-Newton solver arrived at a solution with minimal error with respect to a reference susceptibility. Then this $P_B$ value was used for other similar datasets. In this work, we used $R2_{th}^* = 30 \text{ s}^{-1}$. The performance of the proposed TFI method in phantom and in vivo was compared with SSQSM and Differential QSM. In this work, the Spherical Mean Value (SMV) with variable kernel size was used to implement the Laplacian in SSQSM and Differential QSM, where the kernel diameter was varied from d to 3 voxels, and the ROI mask was eroded accordingly for these two methods. The kernel diameter d at the most central ROI was optimized as described below.

Simulation

Accuracy of PDF+LFI and TFI. We constructed a numerical brain phantom of size 80×80×64. Brain tissue susceptibilities were set to 0 ppm, except for a single point susceptibility source of 0.1 ppm. Background susceptibilities were set to 0, and the total field was computed with the forward model $f = Md^*\chi$. Both LFI and TFI without preconditioning ($P_B=1$) were used, and the estimation for the point source $X_S$ was compared to the truth $\chi_{ST}$ (0.1 ppm). For sequential inversion, both PDF and LBV were used for background field removal and MEDI for local field inversion. This process was repeated by moving the point source across the entire ROI, which generated an error map showing the spatial variation of the estimation error $|X_S - \chi_{ST}|/\chi_{ST}$ for each method. The regularization parameter $\lambda$ was set to $10^{-3}$ for PDF+LFI, LBV+LFI and TFI.

Effect of the preconditioner in TFI. A numerical brain phantom of size 256×256×98 was constructed with known susceptibilities simulating different brain tissues: white matter (WM) −0.046 ppm, gray matter (GM) 0.053 ppm, globus pallidus (GP) 0.19 ppm, and cerebrospinal fluid (CSF) 0, Background susceptibilities were set to 9 ppm to simulate air outside the ROI. The total field was computed from the true susceptibility map $\chi_T$ (FIG. 3a) using the forward model. Gaussian white noise (SNR=200) was added to the field. We applied the proposed TFI method using four different preconditioners: $P_B=1$(no preconditioning), 5, 30 and 80 and using Eq. 6. During reconstruction, the discrepancy $\|M(f-d^*\chi)\|_2$ and the root mean square error (RMSE) $\text{Err}_{simu} = \|M\chi - M\chi_T\|_2/\sqrt{n}$ between the estimated susceptibility $M\chi$ and the true susceptibility $M\chi_T$ (n is the number of voxels inside M) were examined to compare convergence. The regularization parameter $\lambda$ was set to $10^{-3}$.

Phantom Experiment

To examine the accuracy of our TFI method, a phantom with 5 gadolinium solution filled balloons were embedded in agarose (1%), with expected magnetic susceptibilities $\chi_{ref}$ of 0.049, 0.098, 0.197, 0.394 and 0.788 ppm, respectively. The measured susceptibilities were referenced to the agarose background. The phantom was scanned at 3T (GE, Waukesha, Wis.) using a multi-echo gradient echo sequence with monopolar Cartesian readout (anterior/posterior) without flow compensation. Imaging parameters were: FA=15, FOV=13 cm, $\text{TE}_1$=3.6 ms, TR=71 ms, #TE=8, $\Delta\text{TE}$=3.5 ms, acquisition matrix 130×130×116, voxel size=1×1×1 mm$^3$, BW=±31.25 kHz and a total scan time of 13 min.

Next, PDF+LFI, TFI, SSQSM and Differential QSM were performed on the same phantom data. Nonlinear field map estimation followed by graph-cut-based phase unwrapping was used to generate the total field. We optimized $P_B$ in Eq. 7, by repeating the TFI methods for a range of $P_B$ values and selecting the value that produced the smallest error between the mean estimated susceptibility $\chi$ for each balloon and its corresponding reference susceptibilities $\chi X_{ref}$: $\text{Err}_{phantom} = \Sigma_{i=1}^{5}((\chi_i - \chi_{refi})/\chi_{refi})^2$ at the end of the 300th CG iteration. The regularization parameter $\lambda$ was determined by minimizing $\text{Err}_{phantom}$ for PDF+LFI, which was then also used for TFI. For SSQSM and Differential QSM, $\lambda$ and the maximum kernel diameter d for the variable radius SMV were jointly determined by minimizing $\text{Err}_{phantom}$

In Vivo Experiment: Healthy Brain

The brains of 5 healthy subjects were imaged using multi-echo GRE at 3T (GE, Waukesha, Wis.) with monopolar readout without compensation. All studies in this work were conducted with the approval of our institutional review board. Imaging parameters were: FA=15, FOV=24 cm, $\text{TE}_1$=3.5 ms, TR=40 ms, #TE=6, ATE=3.6 ms, acquisition matrix=240×240×46, voxel size=1×1×3 mm$^3$, BW=±62.5 kHz and a total scan time of 9 min. For each subject, 3 orientations were imaged, and the reference brain QSM $\chi_{Lref}$ was reconstructed using COSMOS. For PDF+LFI, TFI, SSQSM and Differential QSM, only one orientation was used. The ROI was obtained automatically using BET. Data from one subject was used to optimize $P_B$ by minimizing the RMSE $\text{Err}_{invivo} = \|\chi_L - \chi_{Lref}\|_2/\sqrt{n}$ between the estimated susceptibility $\chi_L$ and the reference $\chi_{Lref}$ at the end of the 300th CG iteration (n is the number of voxels inside the ROI. The obtained weight $P_B$ was then used for the remaining 4 subjects. The CSF was chosen as the reference for the in vivo susceptibility value in this work. Susceptibilities were measured within ROIs of the GP, putamen (PT), thalamus (TH) and caudate nucleus (CN) for quantitative analysis. The relative difference $(\chi_{GP} - \chi_{GP}^{COSMOS})/\chi_{GP}^{COSMOS}$ was calculated for each subject, with $\chi_{GP}$ the mean susceptibility measurement of GP for each subject. The regularization parameter $\lambda$ was chosen by minimizing $\text{Err}_{invivo}$ for PDF+LFI while TFI used the same $\lambda$. The maximum kernel diameter d and the regularization parameter $\lambda$ were jointly determined by minimizing $\text{Err}_{invivo}$ for SSQSM and Differential QSM.

In vivo Experiment: Patient Study

We acquired human data in 18 patients, each with intracerebral hemorrhage (ICH), brain tumors that including cancerous lesions, and calcified lesions, using multi-echo GRE at 3T (GE, Waukesha, Wis.) with monopolar readout without flow compensation. Imaging parameters were: FA=15, FOV=24 cm, $\text{TE}_1$=5 ms, TR=45 ms, #TE=−8, $\Delta\text{TE}$=5 ms, acquisition matrix=256×256×28~52, voxel size=1×1×2.8 mm$^3$, BW=±31.25 kHz and parallel imaging factor R=2. Total scan time was proportional to the number of slices (about 10 slices/min). For each case, we applied PDF+LFI, TFI, SSQSM and Differential QSM to estimate the QSM of brain with ICH. For TFI, Eq. 4 was used and $P_B$ was determined from the previous in vivo COSMOS experiment. The R2* threshold was $R2_{th}^* = 30 \text{ s}^{-1}$, which, in preliminary studies, was empirically determined to effectively distinguish the hemorrhage site from surrounding brain tissue. The regularization parameter $\lambda$ was chosen using L-curve analysis for PDF+LFI, SSQSM and Differential QSM, while TFI used the same λ as in PDF+LFI. The same kernel diameters d as in the COSMOS experiment were used here for SSQSM and Differential QSM, respectively. To quantify the shadow artifact around ICH, the mean susceptibility within a 5 mm wide layer surrounding each ICH was computed for PDF+LFI and TFI. The reduction in standard deviation (SD) in non-ICH regions was also computed as a measure for ICH-related artifact reduction. It was defined as $R = SD(\chi_{PDF}|M_{non-ICH}) - SD(\chi_{TFI}|M_{non-ICH}))/SD(\chi_{PDF}|M_{non-ICH})$, where $\chi|M_{non-ICH}$ denotes the susceptibilities in the non-ICH region.

In vivo Experiment: Whole Head QSM

Since the proposed method no longer separates background field removal and local field inversion, it is possible to generate a susceptibility map for the entire head by including tissues outside the brain (e.g. scalp, muscles and oral soft tissues) into the ROI M in Eq. 8. We acquired one healthy human brain data at 3T (GE, Waukesha, Wis.) using a multi-echo gradient echo sequence with monopolar 3D radial readout for large spatial coverage. Flow compensation was off. Imaging parameters were: FA=15, FOV=26 cm, $TE_1$=1 ms, TR=34 ms, #TE=9, ΔTE=3 ms, acquisition matrix=256×256×256, voxel size=1×1×1 mm$^3$, BW=±62.5 kHz, number of radial projections=30000, scan time of 15 min, and reconstruction using regridding. TFI was used with $P_B$ determined from the previous in vivo COSMOS experiment. The ROI M in Eq. 8 was determined by thresholding the magnitude image I: M:= I>0.1 max(I). The total field was estimated using a graph cut based concurrent phase unwrapping and chemical shift determination. As phase wrapping is an integer operation in unit of 2π and graph cut technique is best for handling such discrete integration operation. Water fat separation problem can be estimated in two steps: 1) generate an initial estimate of phase unwrapping, susceptibility field and chemical shift by simplifying a voxel composition as either water or fat, 2) input the initial estimates into a full water-fat signal model to fine-tune susceptibility and water-fat fraction through numerical optimization. As water-fat is not a convex problem, the first step based on graph cut provides a robust initialization for water-fat numerical optimization procedure to converge to a realistic solution.

Differential QSM was also applied using this ROI. For comparison, QSM of only the brain was also reconstructed with TFI using the mask obtained from BET. The regularization parameter λ was chosen using L-curve analysis for brain-only TFI, Differential QSM and whole head TFI.

All computations in this work were performed in MATLAB on a desktop computer with a 6-core CPU (Intel Core i7) and 32 GB memory.

1.4. Results

Simulation

Figure 2:
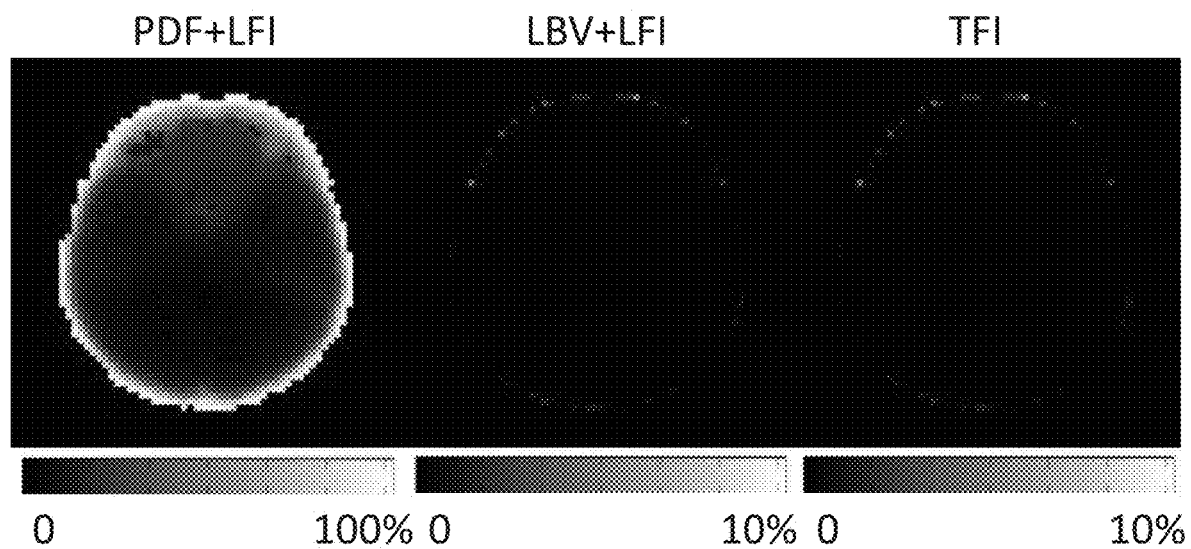
FIG. 2 shows an error map for PDF+LFI, LBV+LFI, and TFI for the 0.1 ppm point source simulation. When the point source is close to the ROI boundary, the error when using TFI is significantly smaller than that using PDF+LFI.

Accuracy of PDF+LFI and TFI In FIG. 2, the PDF+LFI method shows an estimation error of less than 10%, except near the boundary of the ROI when the source was within 4 voxels of the boundary, the error was at least 40%. In contrast, the maximum error for both LBV+LFI and the proposed TFI were 4.8% throughout the ROI, including the boundary.

Figures 3A, 3B, 3C:
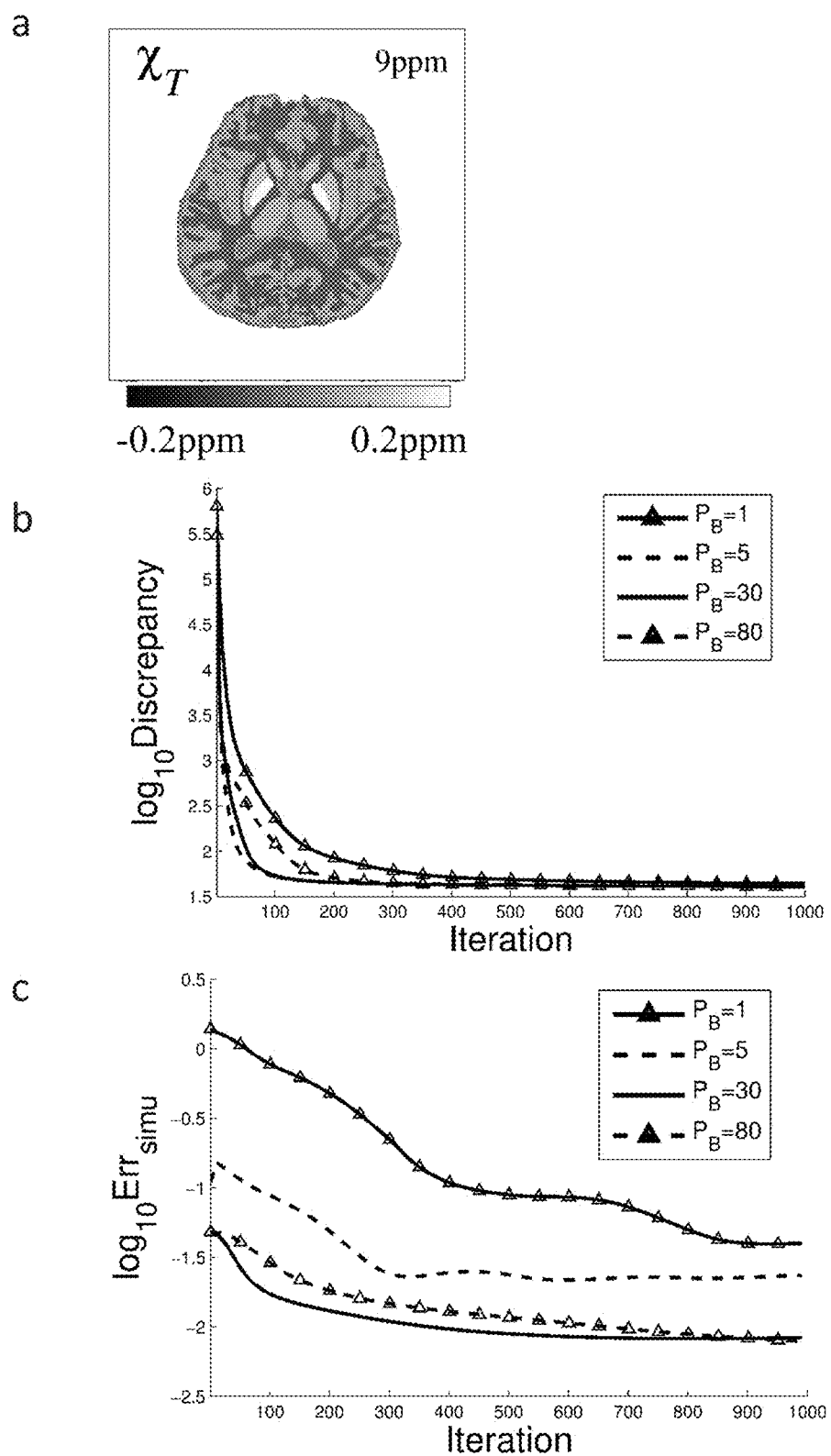
FIGS. 3a-3c show a true susceptibility map (a) used in simulation. Discrepancy (b) and error (c) between estimated and true brain QSM in simulation with different preconditioning weights $P_B$

Effect of preconditioner P in TFI. FIG. 3b shows that for $P_B$>1, the discrepancy between the measured and the estimated total field decreased faster compared to using no preconditioning ($P_B$=1), FIG. 3c shows that, for large enough CG iteration numbers (>1000), the preconditioned solvers converged to $Err_{simu}$<0.04 with respect to the reference for all $P_B$ values. On the other hand, at CG iteration 100, $P_B$=30 achieved a smaller $Err_{simu}$ (FIG. 3c) compared to $P_B$=5 or 80.

Phantom

Figure 4A:
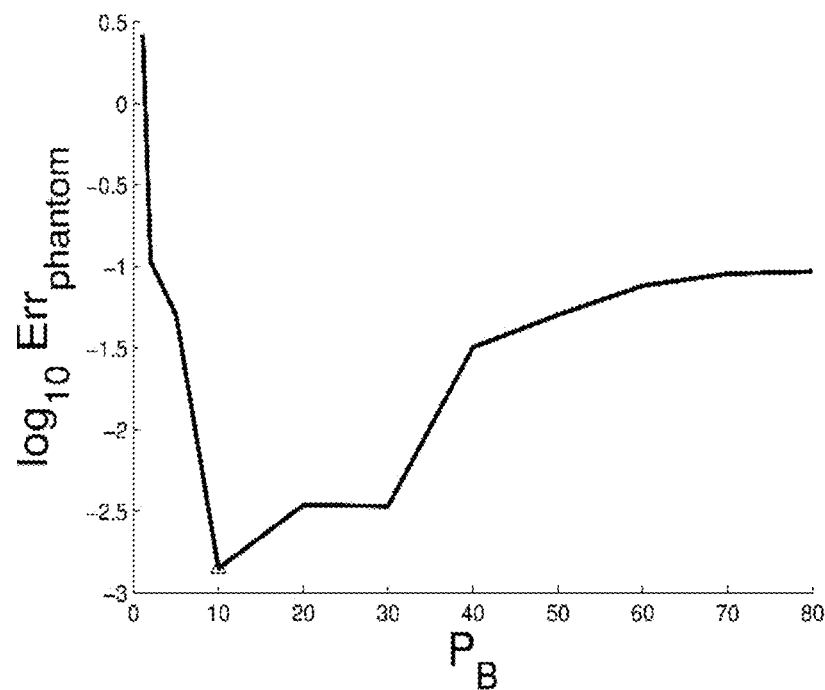
FIGS. 4a-4b show the weight $P_B$ in preconditioner is optimized by minimizing the error between the estimated QSM and the reference value both in the phantom (a) and in vivo (b) an example magnitude component of the MRI signal collected from a water phantom with Gadolinium doped balloons using a gradient echo sequence.

The optimized regularization parameter λ was 2×10$^{-2}$ for both PDF+LFI and TFI, 5×10$^{-1}$ for SSQSM and 5×10$^{-3}$ for Differential QSM. The optimized kernel diameter d was 13 for SSQSM and 3 for Differential QSM. The weight $P_B$=10 was found to be optimal here (FIG. 4a). Linear regression between the estimated (y) and reference (x) balloon susceptibilities were: PDF+LFI y=0.978x−0.004 (R=1.000); TFI y=0.973x+0.004 (R=1.000); SSQSM y=0.833x+0.019 (R=0.999); Differential QSM y=0.971x+0.004 (R=1.000). $Err_{phantom}$ were: PDF+LFI: 0.0158, TFI: 0.0050, SSQSM: 0.0350, Differential QSM: 0.0010.

In vivo Imaging: Healthy Brain

Figure 4B:
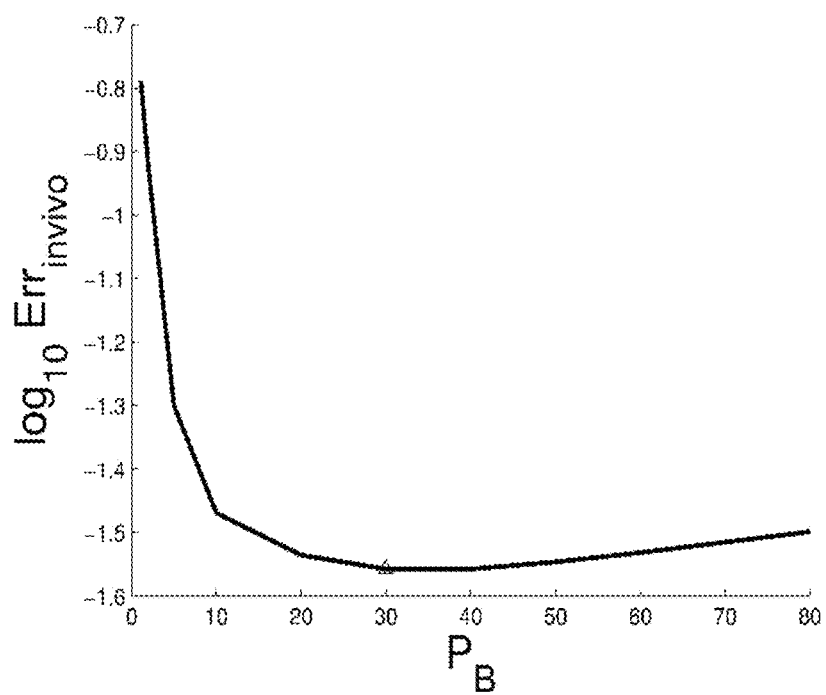

FIGS. 1a-1i shows brain QSMs reconstructed using PDF+LFI, un-preconditioned TFI ($P_B$=1) and preconditioned TFI ($P_B$=30), at different CG iterations. With preconditioning ($P_B$=30), CG generated a local tissue susceptibility similar to that obtained with PDF+LFI in 50 iterations, while the un-preconditioned TFI needed 300 iterations to reach a comparable solution, $P_B$=30 was determined by minimizing $Err_{invivo}$ (FIG. 4b). The average reconstruction time was 232 seconds for PDF+LFI, 270 seconds for TFI, 50 seconds for SSQSM and 284 seconds for Differential QSM. The regularization parameter λ was 10$^{-3}$ for both PDF+LFI and TFI, 5×10$^{-2}$ for SSQSM and 1×10$^{-3}$ for Differential QSM. The maximum kernel diameter d was 17 for SSQSM and 3 for Differential QSM.

Figure 5:
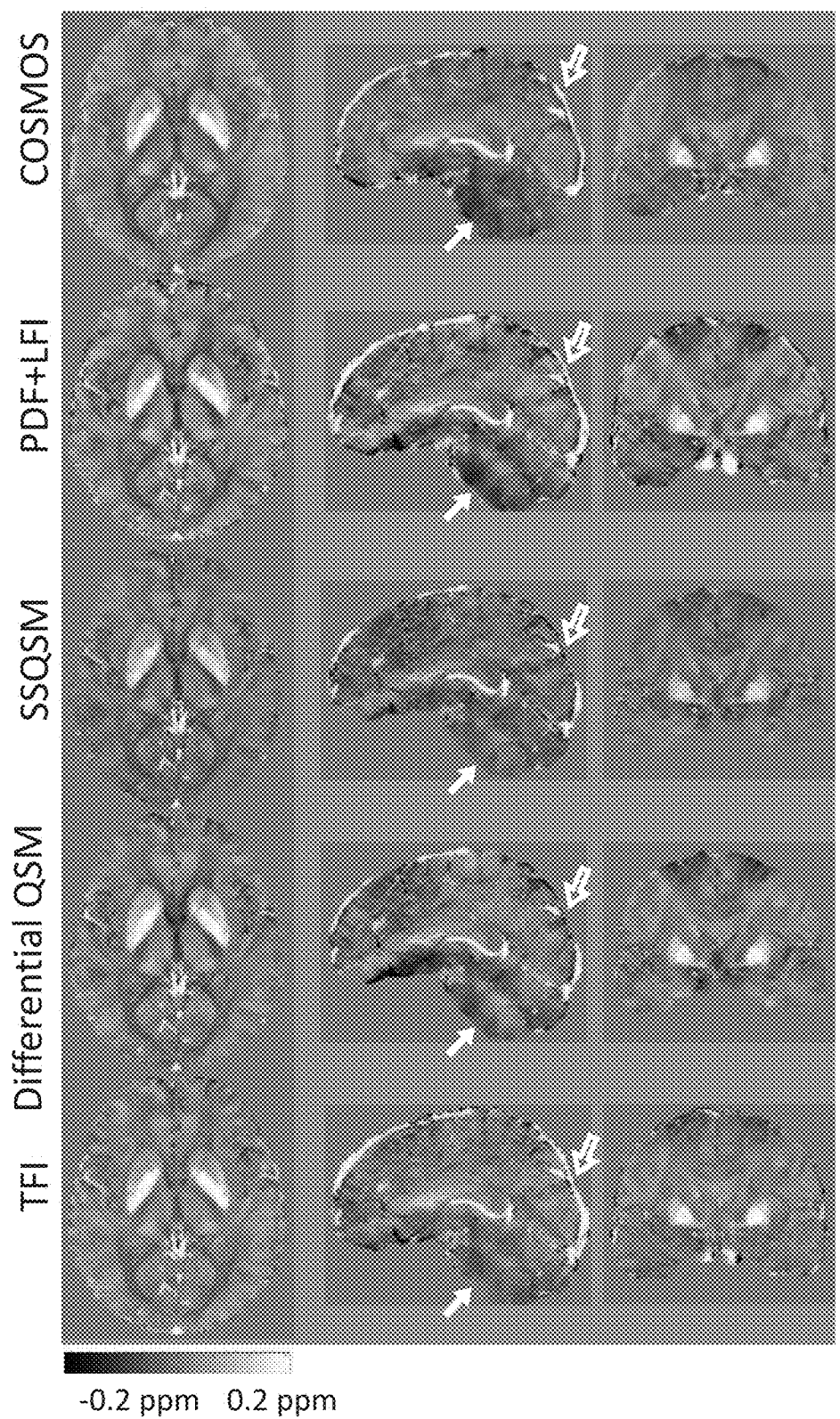
FIG. 5 shows in vivo healthy QSM estimated with COSMOS, PDF+LFI, SSQSM, Differential QSM and proposed TFI. Both PDF+LFI and TFI give more complete depiction of superior sagittal sinus than SSQSM or Differential QSM, especially at posterior brain boundary (hollow arrow). At the bottom of the cerebrum (solid arrow), TFI's result is more homogeneous than PDF+FLI.
Figure 6:
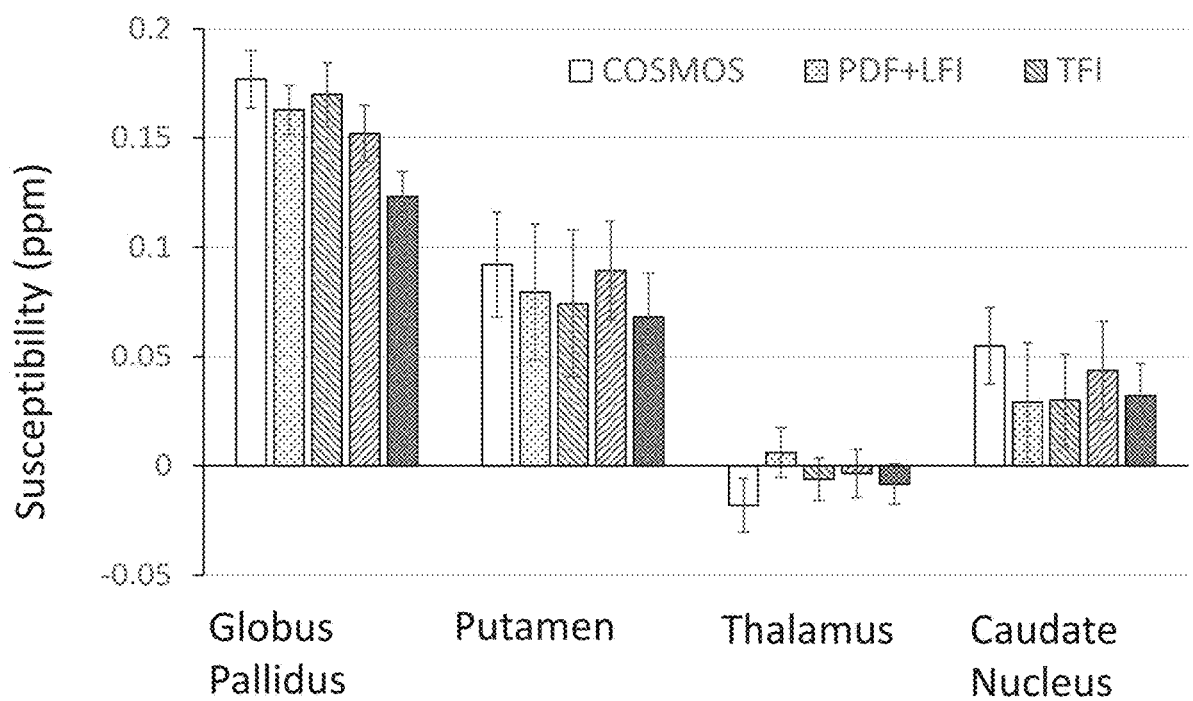
FIG. 6 shows the mean and standard deviation of measured susceptibilities of globus pallidus, putamen, thalamus and caudate nucleus in FIG. 5 for COSMOS, PDF+LFI, TFI, Differential QSM and SSQSM. These 5 methods show comparable measurement for putamen, thalamus and caudate nucleus. For globus pallidus, SSQSM shows significant underestimation than COSMOS, PDF+LFI, TFI or Differential QSM.

FIG. 5 shows that the QSM for all methods were consistent with the COSMOS map near the center of the brain. Meanwhile, homogeneity of QSM in the lower cerebrum (solid arrow in FIG. 5) was improved using TFI compared to PDF+LFI. The superior sagittal sinus was better visualized with PDF+LFI and TFI than with SSQSM and Differential QSM, especially at the posterior brain cortex (hollow arrow in FIG. 5). The measured susceptibilities for deep GM are shown in FIG. 6. Using COSMOS as reference, significant underestimation was observed for SSQSM in the measurement of GP susceptibility compared to Differential QSM, PDF+LFI or TFI. This underestimation was observed in other subjects as well. Compared to the COSMOS measurement, SSQSM underestimated the susceptibility of the GP by 27.4% on average, compared to 5.4%, 9.6% and 8.9% for PDF+LFI, TFI and Differential QSM, respectively.

In vivo Imaging Brain with Hemorrhage

Figure 7:
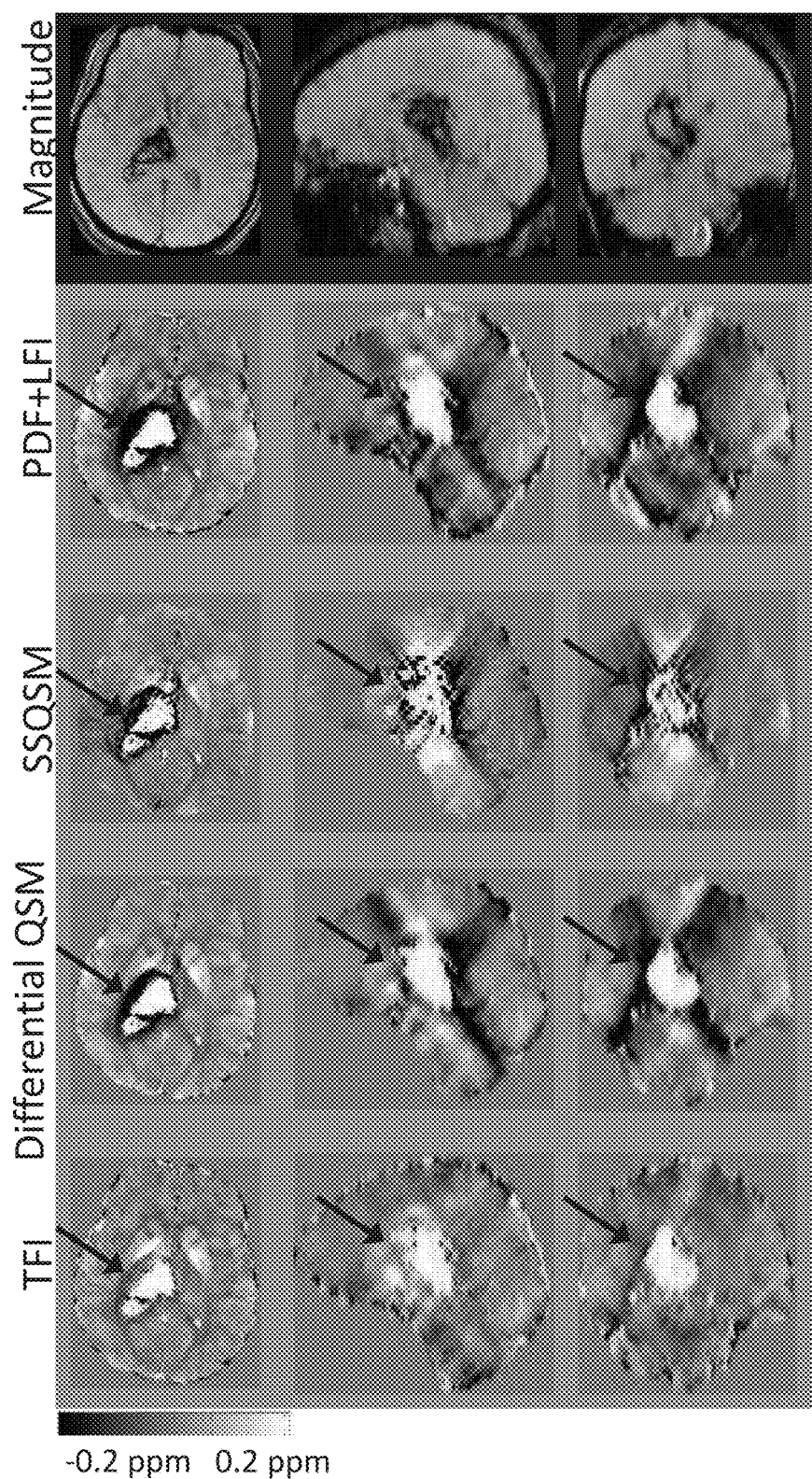
FIG. 7 shows an in vivo result in one patient suffering from intracerebral hemorrhage. From top to bottom: T2*-weighted magnitude image, QSM reconstructed using PDF+LFI, SSQSM, Differential QSM and proposed TFI.

All hemorrhage patient brain images were reconstructed using $P_B$=30 for TFI. The average reconstruction time was 328 seconds for PDF+LFI, 325 seconds for TFI, 50 seconds for SSQSM and 344 seconds for Differential QSM. The regularization parameter λ was 10$^{-3}$ for both PDF+LFI and TFI, 2×10$^{-3}$ for SSQSM and 5×10$^{-4}$ for Differential QSM. Maximum kernel diameter d was 17 for SSQSM and 3 for Differential QSM. FIG. 7 shows one example with reduced shadowing artifacts around the ICH site using the proposed preconditioned TFI method as compared to using PDF+LFI, SSQSM or Differential QSM, in particular, we observed that the GP structure was more discernible with the shadowing artifact removed (as indicated by arrows in FIG. 7). Considering that the shadow artifact around ICH manifests itself as negative susceptibility, the increase in the mean susceptibility within ICH's vicinity indicates a reduction of the artifact. The standard deviation reduction similarly points to the reduction of this shadow artifact.

Whole Head QSM

Figure 8:
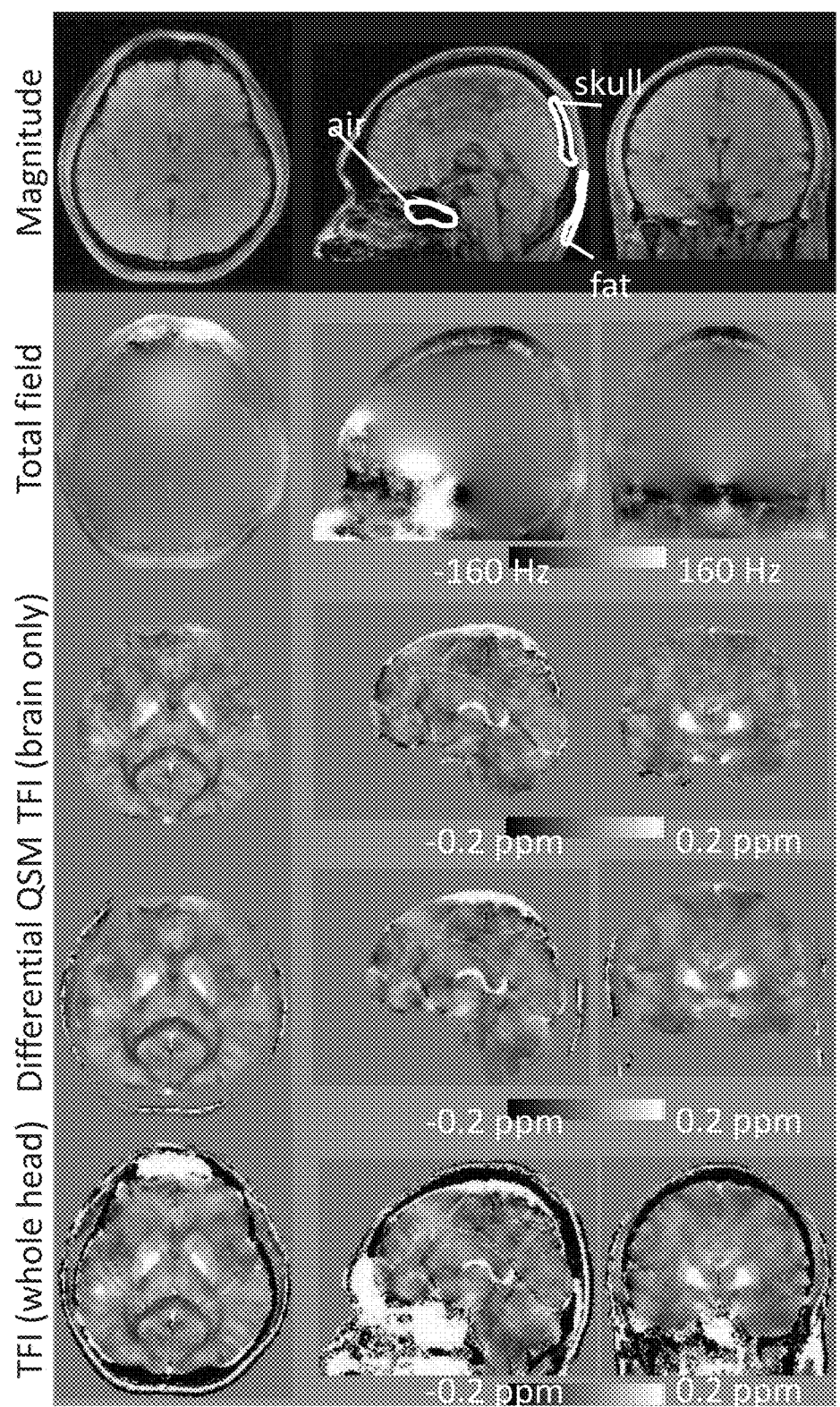
FIG. 8 Magnitude (first row), total field (second row), TFI-generated brain QSM (third row), Differential QSM (fourth row) and TFI-generated whole head QSM (bottom row) are shown in axial (left column), sagittal (middle column) and coronal (right column) views. The susceptibility distribution for skull, air filled sinuses and subcutaneous fat is clearly depicted with whole head TFI. Example ROIs are shown and mean susceptibility values are calculated for: nasal air=7.38 ppm, skull=−1.36 ppm and fat=0.64 ppm.

The whole head QSM was compared with the magnitude/phase image and brain QSM (FIG. 8). The reconstruction time was 13.4 minutes for brain-only TFI, 19 minutes for Differential QSM and 14.2 minutes for whole head TFI. The regularization parameter λ was $10^{-3}$ for both brain-only TFI and Differential QSM, and $2.5 \times 10^{-3}$ for whole head TFI. The results show that the intracerebral map in whole head TFI QSM was consistent with the brain-only TFI, although the brain-only TFI generated slightly better homogeneity at top part of the brain as seen in the sagittal and coronal view. Meanwhile, whole head QSM also provided additional mapping of susceptibility for extracerebral structures, such as the skull, air-filled sinuses and subcutaneous fat. Since the ROI was determined by thresholding magnitude images, the exterior of the brain was more distinct in whole head QSM compared to brain-only QSM, especially at brain stem and cerebellum. Additionally, whole head QSM clearly discriminated the skull and the sinus air, which was hard to distinguish in the magnitude image due to the loss of MR signal in both regions. Example ROIs were delineated for sinus air, skull and fat, as in FIG. 8, and the mean susceptibility was calculated to be 7.38 ppm for the sphenoidal sinus, −1.36 ppm for the skull, and 0.64 ppm for fat. These susceptibility values are consistent with prior literature. When comparing Differential QSM and whole head TFI, a similar susceptibility map was obtained within the brain, while Differential QSM did not depict the susceptibilities of the skull and sinus air.

1.5. Conclusion

Our data demonstrate that total field inversion (TFI) for QSM eliminates the need for separate background field removal and local field inversion (LFI), and that preconditioning can accelerate TFI convergence. Compared to the traditional PDF+LFI approach, TFI provides more robust QSM in regions near high susceptibility regions such as those containing air or hemosiderin present in hemorrhages, within similar reconstruction time. It is also demonstrated that TFI is able to generate the whole head QSM without the need for brain extraction.

The sequential background field removal and LFI process the same data using the same Maxwell equations but require an assumption or regularization) to differentiate the background field and the local field. For the background field removal exemplified here using PDF, it is assumed that the Hilbert space L spanned by all possible local unit dipole fields $f_{dL}$ is orthogonal to the Hilbert space B spanned by all possible background unit dipole fields $f_{dB}$. However, this orthogonality assumption is not valid when the local unit dipole is close to the ROI boundary, and will cause error in PDF. This error or similar error introduced by any other background field removal method propagates into the subsequent LFI and produces an inaccurate local susceptibility estimation. However, there is no need to break the problem of fitting MRI data with the Maxwell equations into two separate background field removal and LFI problems. Our proposed TFI eliminates this separation and avoids the associated error propagation. Improvement of TFI over PDF+LFI is shown in Simulation (FIG. 2) and in vivo (FIG. 5), especially when the local source of interest is close to the ROI boundary. It is noted that LBV+LFI also outperforms PDF+LFI in separating local and background field, but in order to exclude noisy phase from Laplacian operation at ROI boundary, LBV requires an accurate ROI mask, which might be challenging for in vivo brain QSM.

Preconditioning is necessary to achieve practical performance with TFI. FIGS. 1a-1i shows that for brain QSM, non-preconditioned TFI takes 300 CG iterations to converge to a solution comparable to PDF+FLI, but the latter method takes only 50 iterations. Here we introduced a prior-enhanced right-preconditioner specific to our TFI problem (Eq. 7). Similar work on a prior-enhanced preconditioner can be found in MR dynamic imaging, where a right-preconditioner is constructed as a smooth filter which incorporates the prior knowledge that coil sensitivities are generally spatially smooth. In a QSM scenario, we consider the susceptibility gap between strong susceptibility sources (e.g. air, skull or hemorrhage) and weak susceptibility sources (e.g. normal brain tissue), by assigning a larger weight ($P_B > 1$) to the strong susceptibility regions in the preconditioner (Eq. 7). This preconditioner P is aimed to approximate a covariance matrix Γ by $P^H P \approx \Gamma$, under the assumption that the solution χ for Eq. 5 is a Gaussian random vector $\chi \sim N(0, \Gamma)$. The convergence of iterative Krylov subspace solvers (such as the CG) can be improved using this preconditioner. This is confirmed with our result shown in FIGS. 1a-1i, where preconditioning reduced the required number of CG iterations by a factor of 6 for TFI. The proposed preconditioner is different from another preconditioner that the system matrix for local field inversion is approximated by a diagonal matrix and used as a preconditioner after inverting. It may therefore be possible to combine both preconditioners in TFI for further speedup.

Since our preconditioner is designed for a large dynamic range of susceptibilities, it straightforwardly applies to intracerebral hemorrhage (ICH). As shown in FIG. 7, preconditioned TFI effectively suppresses the artifact near the hemorrhage site and enhances the QSM quality for ICH. Previous work in handling a large range of susceptibilities is based on the piecewise constant model either explicitly specified as in, or implicitly using a strong edge regularization. In these methods, different regularization parameters need to be carefully chosen for strong and weak susceptibilities, respectively. Otherwise, under-regularization would induce streaking artifacts near the hemorrhage site, or over-regularization would sacrifice fine detail in weak susceptibility regions. Our proposed TFI method utilizes preconditioning to improve convergence towards an artifact-reduced solution, as opposed to using multiple levels of regularization. This eliminates the need for combining QSMs from multiple local field inversion instances. On the other hand, the described preconditioning can be applied to LFI to suppress the artifact near the hemorrhage site in QSM of ICH, similar to preconditioned TFI. For whole head. QSM (FIG. 8), our proposed preconditioned produces intracerebral (weak) and extracerebral (strong) QSM simultaneously, whereas the intracerebral component is less well seen in due to over-regularization.

Laplacian-based methods, SSQSM and Differential QSM use the harmonic property of the background field $f_B$ ($\Delta f_B = 0$ within the ROI) to eliminate both phase unwrapping and background field removal, enabling local susceptibility estimation in a single step SSQSM further speeds up by omitting the SNR weighting and using L2 norm for regularization. However, Laplacian-based methods suffer from brain erosion: The Laplacian is implemented using the finite difference operator or the spherical kernel operator, both requiring the ROI mask to be eroded. As a consequence, erosion of superior sagittal sinus can be seen in SSQSM and Differential QSM (FIG. 5). This brain erosion problem is avoided in PDF+LFI and TFI that do not evaluate the Laplacian. Furthermore, SSQSM suffers from substantial susceptibility underestimation in phantom and in vivo, compared to Differential QSM, PDF+LFI and TFI. This underestimation was also observed for a range of values for the regularization parameter λ around the reported value (results not shown). This may be caused by the use of L2-norm regularization, which has been shown to underestimate susceptibility compared to L1-norm regularization. Moreover, Differential QSM does not estimate the susceptibilities of the skull and sinus air (FIG. 8). This is consistent with previous literature. The reason is that, since ROI is determined by thresholding the magnitude image, the skull and sinus air are not included and are considered as "background". Therefore, the Laplacian operation removes the field generated by the skull and sinus air. On the contrary, TFI preserves the field they generate and depicts their susceptibilities (FIG. 8).

The capability of quantitatively mapping both diamagnetic and paramagnetic materials as demonstrated here for the whole head QSM can be applied to atherosclerotic imaging to resolve and define calcification (diamagnetic with negative susceptibility) and intraplaque hemorrhage (paramagnetic with positive susceptibility) in plaques found in carotid arteries, coronary arteries, aorta and other vessel walls. The multi-echo gradient echo 3D sequence can be modified to include EEG gating to reduce effects from pulsatile changes over the cardiac cycle, and the flow compensation can be included to minimize flow generated phase. The QSM of plaque calcification and intraplaque hemorrhage components would solve the problem of confounding calcification and hemorrhage, both of which appear hypointense in magnitude images, allowing measurement of intraplaque hemorrhage that is a major determinant of plaque vulnerability.

The whole head QSM provides skull bone calcification spatial distribution quantification, which has been shown to be linearly proportional to the attenuation coefficients measured on CT. This skull bone and other intracranial calcifications measured on QSM can be used to correct for ultrasound attenuation and scattering in magnetic resonance guided focused ultrasound (MRgFUS), and to correct for gamma attenuation MR/PET that simultaneously forms MRI and positron emission tomography (PET) images. Both MRgFUS and MR/PET requires correction based on quantitative bone spatial distribution, which are not available from standard MRI and may require an additional CT imaging session with costs and radiation. Bone defined on QSM can eliminate this CT need for MRgFUS and MR/PET.

The preliminary implementation of preconditioned TFI can be further developed with the following considerations. First, the current choice of the preconditioner P is empirical and performance may be improved by selecting a patient specific value or model. Further work might focus on determining P from physical or statistical models of the susceptibility distribution for better approximation of the covariance matrix Γ. A prior QSM estimation, which can be calculated very fast by methods such as SSQSM, might also be helpful in modeling this distribution and constructing the preconditioner. Second, the construction of our preconditioner requires R2* map to extract intracerebral region with strong susceptibility, such as ICH. If the R2* information is not available, especially when only single-echo image is acquired, the preconditioned TFI might be less effective in suppressing ICH-based shadow artifact. In future work, we will focus on incorporating other contrast (magnitude, T1-weighted or T2-weighted image) into constructing the preconditioner. Third, for whole head QSM, the skull has very short T2*, such that the multi-echo GRE sequence fails to acquire skull MR signal for field estimation. In future work, the use of an ultra-short echo time (UTE) pulse sequence to provide phase information in the skull will likely lead to a more accurate susceptibility map. The magnitude signal from UTE sequence might also be used for differentiating skull and air-filled sinus, hence enabling more effective preconditioning by assigning different weight $P_B$ for these regions. Finally, the proposed TFI method uses a linear signal model but can be extended to a non-linear formulation similar to that of, in order to bypass the phase unwrapping step and improve the noise modeling. However, caution is needed because the non-linear and non-convex objective function has multiple local minimum. Given the fact that the desired solution is fairly large outside the ROI, such as that of air, the all-zero initial guess used in this work may cause the solver to converge to an incorrect local minimum. Future work will be focused on construction of an initial guess robust against this problem. The current linear solution may provide such an initial guess.

In summary, we describe a preconditinoed total field inversion (TFI) algorithm for QSM reconstruction. This eliminates the need for sequential background field removal and local field inversion, and it achieves a higher accuracy at the boundary of the susceptibility map. We also introduce a preconditioner to improve convergence, We show that the proposed preconditioned TFI: suppresses streaking artifacts in QSM of intracerebral hemorrhage. TFI is also capable of mapping the susceptibility of the entire head including brain tissue, skull, air-filled sinus and subcutaneous fat.

2. Anisotropic Weighting for Structure Prior

In this section, we present an improvement on constructing the structure prior by taking into account of the structural edge orientation.

2.1. Introduction

Using a mathematical analysis of the field-to-susceptibility inverse problem, it has been shown that streaking artifacts in QSM are originated from the dipole-incompatible part of the field. This incompatible part includes noise, discretization induced error, anisotropic sources or chemical shift. Furthermore, it is shown that streaking-free solutions can be obtained from the dipole-compatible part of the field only. However, noise is omnipresent in practice, discretization is indispensable for numerical computation, and anisotropic sources cannot be measured reliably in a single-angle acquisition. Therefore, regularization in image space plays a crucial role in computing solutions with minimal streaking.

Among others, morphology enabled dipole inversion (MEDI) is an approach capable of enhancing tissue structure by imposing spatial consistency (edge information) between a candidate susceptibility map and the magnitude image associated with the susceptibility map. To be specific, the structural prior is incorporated into total variation (TV) regularization as an isotropic matrix. This aims at 1) preserving common edges between the magnitude image and a candidate susceptibility map tissue structure; and 2) penalizing strong gradients elsewhere streaking artifacts. Therefore, its performance largely depends on how to design such a structural prior (matrix). This paper focuses on the design of this structural prior that takes into account orientation information which was previously missing in isotropic weighting.

The remainder of this paper is organized as follows: In THEORY, we consider anisotropic weighting (AW) for a structural prior that takes into account orientation consistency. In METHODS and RESULTS, we demonstrate the effectiveness of AW in two in vivo brain MRI datasets where COSMOS or the component of the susceptibility tensor $\chi X_{33}$ are available as reference. In DISCUSSION and CON- CLUSION, we conclude with some discussion on our results. MATLAB source codes will be available at http://weill.cornell.edu/mri/.

2.2. Theory

In a spatially continuous setting, the problem of regularized dipole inversion within a region of interest $\Omega$ is written as the following variational problem:

$$\chi^* = \arg\min_{\chi \in BV(\Omega;\mathbb{R})} \frac{\lambda}{2} \int_\Omega |w(d*\chi - b)|^2 + Reg(\chi) \quad [12]$$

where the susceptibility distribution $\chi$: $(\Omega \subset \mathbb{R}^3) \to \mathbb{R}$ ($L^1$-integrable) is estimated from the measured local field b: $\Omega \to \mathbb{R}$ The admissible solution space BV ($\Omega;\mathbb{R}$) of bounded variation (BV) allows the existence of jumps (sharp edges). The map w: $L^1 \to L^1$ in the data fidelity term compensates for the non-uniform phase noise (SNR weighting). Here, d and * are the unit dipole kernel and the convolution operation, respectively. The regularization term $Reg(\chi)$ is designed in such a way that it effectively penalizes streaking artifacts originated from the dipole-incompatible part of the field b. In MEDI, for instance, the regularization term is formulated as follows:

$$Reg(\chi) := \int_\Omega \|M_G \nabla \chi\|_1 = \quad [13]$$

$$\int_\Omega \left\| \begin{pmatrix} 1-\delta_x(r) & 0 & 0 \\ 0 & 1-\delta_y(r) & 0 \\ 0 & 0 & 1-\delta_z(r) \end{pmatrix} \begin{pmatrix} \partial_x \chi(r) \\ \partial_y \chi(r) \\ \partial_z \chi(r) \end{pmatrix} \right\|_1 dr,$$

where $\delta_x(r)$, $\delta_y(r)$, and $\delta_z(r)$ are edge indicators for the x-, y-, and z-directions at r=(x, y, z), respectively. That is, $\delta_x(x_0, y_0, z_0)=1$ if there is an edge along the x-axis at $r_0=(r_0, y_0, z_0)$; otherwise $\delta_x(r_0)$. Likewise, $\delta_y(r)$ and $\delta_z(r)$ are defined. Since these edge indicators are computed from the magnitude image associated with the unknown susceptibility map under the assumption that edges in the two images coexist, the regularizer $Reg(\chi)$ penalizes only the regions where tissue structure (edges) is not expected. Note that $\lambda>0$ is a tuning parameter that balances data fidelity and regularization.

In order to take into account edge orientation information, an anisotropic weighting can be defined as follows:

$$Reg^\perp(\chi) := \int_\Omega \|P_{\perp\xi} \nabla \chi\|_1 = \int_\Omega \left\| \left(I - \frac{\xi\xi^T}{\xi^T\xi}\right) \nabla \chi \right\|_1 = \quad [14]$$

$$\int_\Omega \left\| \begin{pmatrix} 1-\xi_1^2(r) & -\xi_1(r)\xi_2(r) & -\xi_1(r)\xi_3(r) \\ -\xi_2(r)\xi_1(r) & 1-\xi_2^2(r) & -\xi_2(r)\xi_3(r) \\ -\xi_3(r)\xi_1(r) & -\xi_3(r)\xi_2(r) & 1-\xi_3^2(r) \end{pmatrix} \begin{pmatrix} \partial_x \chi(r) \\ \partial_y \chi(r) \\ \partial_z \chi(r) \end{pmatrix} \right\|_1 dr,$$

where $\xi(r)$ is the edge indicator $\delta$: $\Omega \to \mathbb{R}$, $r \mapsto \delta_x(r) \vee \delta_y(r) \vee \delta_z(r)$ multiplied by the gradient vector of the magnitude image Mag(r) at r as follows:

$$\xi(r) = \begin{pmatrix} \delta(r) & 0 & 0 \\ 0 & \delta(r) & 0 \\ 0 & 0 & \delta(r) \end{pmatrix} \begin{pmatrix} \partial_x Mag(r) \\ \partial_y Mag(r) \\ \partial_z Mag(r) \end{pmatrix}. \quad [15]$$

Figure 9:
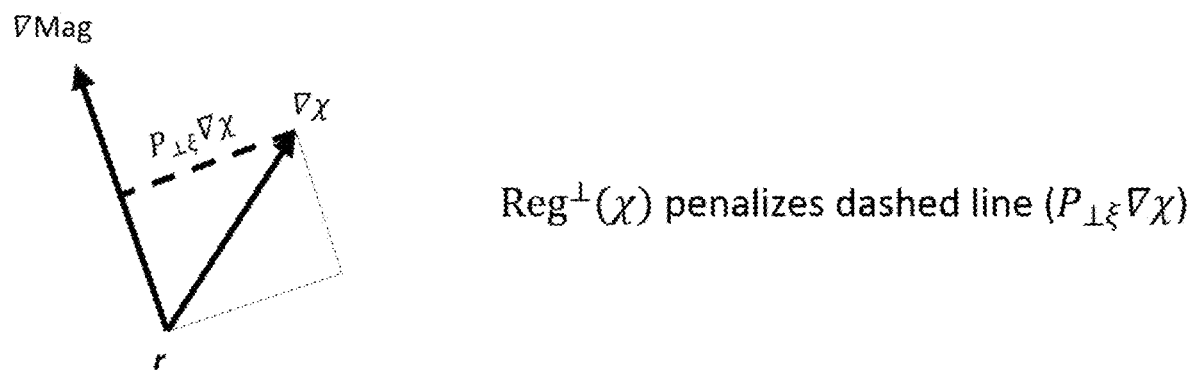
FIG. 9. The anisotropic weighting matrix $P_{\perp g}$ defined in the THEORY section penalizes the perpendicular component of the gradient of $\chi$ with respect to the gradient of the corresponding magnitude image (green). Therefore, it promotes the parallel orientation between the two vectors.

Note that V denotes the Boolean OR operation. The matrix $P_{\perp\xi}$ is the rank-2 orthogonal projector that eliminates the component in the direction of $\xi$. In other words, we modify the regularization term such that it penalizes the components of the susceptibility distribution gradient that are orthogonal to the magnitude image gradient, as illustrated in FIG. 9. Therefore, we promote the parallel orientation—not just the concurrent existence between the magnitude and susceptibility edges, which enhances coherence in morphology between the two images.

Not only is the data fidelity term convex, but also both regularization terms $Reg(\chi)$ and $R^\perp(\chi)$ are convex in $\chi$. Therefore, one can use some well-established algorithms for this convex optimization problem such as the Gauss-Newton conjugate gradient method, the split-Bregman method, and the primal-dual algorithm to efficiently minimize the energy [12]. In this paper, we use the Gauss-Newton conjugate gradient method with the Sobolev space assumption, which solves the Euler-Lagrange equations associated with the first variation of the energy functional in [12]. The first variation of $Reg(\chi)$ is derived as follows:

$$\frac{\partial Reg(\chi)}{\partial \chi} = -\frac{\partial}{\partial x}\left(\frac{(1-\xi_1^2(r))\partial_x \chi(r)}{|(1-\xi_1^2(r))\partial_x \chi(r)|}\right) - \quad [16]$$

$$\frac{\partial}{\partial y}\left(\frac{(1-\xi_2^2(r))\partial_y \chi(r)}{|(1-\xi_2^2(r))\partial_y \chi(r)|}\right) - \frac{\partial}{\partial z}\left(\frac{(1-\xi_3^2(r))\partial_z \chi(r)}{|(1-\xi_3^2(r))\partial_z \chi(r)|}\right),$$

where the gradient operator $\nabla$ should be understood in the distributional sense in BV. Note that the above first variation [16] is not well-defined in BV but is in the Sobolev space, which is the assumption behind the Gauss-Newton conjugate gradient method.

The first variation of $Reg^\perp(\chi)$ is derived as follows:

$$\frac{\partial Reg^\perp(\chi)}{\partial \chi} = \quad [17]$$

$$-\frac{\partial}{\partial x}\left(\frac{(1-\xi_1^2(r))\partial_x \chi(r) - \xi_1(r)\xi_2(r)\partial_y \chi(r) - \xi_1(r)\xi_3(r)\partial_z \chi(r)}{|(1-\xi_1^2(r))\partial_x \chi(r) - \xi_1(r)\xi_2(r)\partial_y \chi(r) - \xi_1(r)\xi_3(r)\partial_z \chi(r)|}\right) -$$

$$\frac{\partial}{\partial y}\left(\frac{-\xi_2(r)\xi_1(r)\partial_x \chi(r) + (1-\xi_2^2(r))\partial_y \chi(r) - \xi_2(r)\xi_3(r)\partial_z \chi(r)}{|-\xi_2(r)\xi_1(r)\partial_x \chi(r) + (1-\xi_2^2(r))\partial_y \chi(r) - \xi_2(r)\xi_3(r)\partial_z \chi(r)|}\right) -$$

$$\frac{\partial}{\partial z}\left(\frac{-\xi_3(r)\xi_1(r)\partial_x \chi(r) - \xi_3(r)\xi_2(r)\partial_y \chi(r) + (1-\xi_3^2(r))\partial_z \chi(r)}{|-\xi_3(r)\xi_1(r)\partial_x \chi(r) - \xi_3(r)\xi_2(r)\partial_y \chi(r) + (1-\xi_3^2(r))\partial_z \chi(r)|}\right).$$

Likewise, this first variation is defined in the Sobolev space.

2.3. Materials and Methods

Here we describe experimental details to evaluate the implementation of anisotropic weighting in TV regularization with respect to isotropic weighting.

Two in viva brain MRI data in 2 healthy subjects were used for experimental validation of the effects of anisotropic weighting using COSMOS or $\chi_{33}$ as reference. These data sets were obtained from the Cornell MRI research group (http://weill.cornell.edu/mri/pages/qsm.html) and from the QSM 2016 reconstruction challenge (http://www.neuroimaging.at/qsm2016/pages/qsm-challenge.php). For imaging parameters and phase preprocessing, we refer the reader to the websites and references therein.

Numerical conditioning was set to $\epsilon=10^{-6}$; the maximum number of inner iterations (nested CG loop) was set to 100; the maximum number of outer iterations was set to 100; the tolerance for the nested. CG loop was set to 0.01; and the relative update norm $\|\chi^{k+1}-\chi^k\|/\|\chi^k\|$, where $\chi^k$ is a solution at the kth outer iteration, was set to 0.01. Note that the stopping criteria are made tighter than default settings to make sure convergence—typically the maximum number of outer iterations is 10 and the relative update norm is 0.1. The algorithm was run in Matlab R2016a on an Intel Core i7 3.30 GHz CPU with 64 GB of memory.

In isotropic weighting, the edge indicators $\delta_x$, $\gamma_y$, and $\gamma_z$, are determined as the following procedure: 1) Compute $\zeta_x(r)=|\partial_x\text{Mag}(r)|$, $\zeta_y(r)=|\partial_y\text{Mag}(r)|$, and $\partial_z(r)=|\partial_z\text{Mag}(r)|$ for $r\in\Omega$; 2) define the edge indicators as characteristic functions of a parameter t as follows: $\delta_x(r)=1_{\{\zeta_x(r)>t\}}(r)$, $\delta_y(r)=1_{\{\zeta_y(r)>t\}}(r)$, and $\delta_z(r)=1_{\{\zeta_z(r)>t\}}(r)$; and 3) find t such that $$\frac{\int_\Omega \delta_x(r)+\delta_y(r)+\delta_z(r)dr}{|\Omega|} \approx 0.9.$$

Then, the resulting binary indicators $\delta_x(r)$, $\delta_y(r)$, and $\delta_z(r)$ are used for [13] and [16].

Figures 10A, 10B:
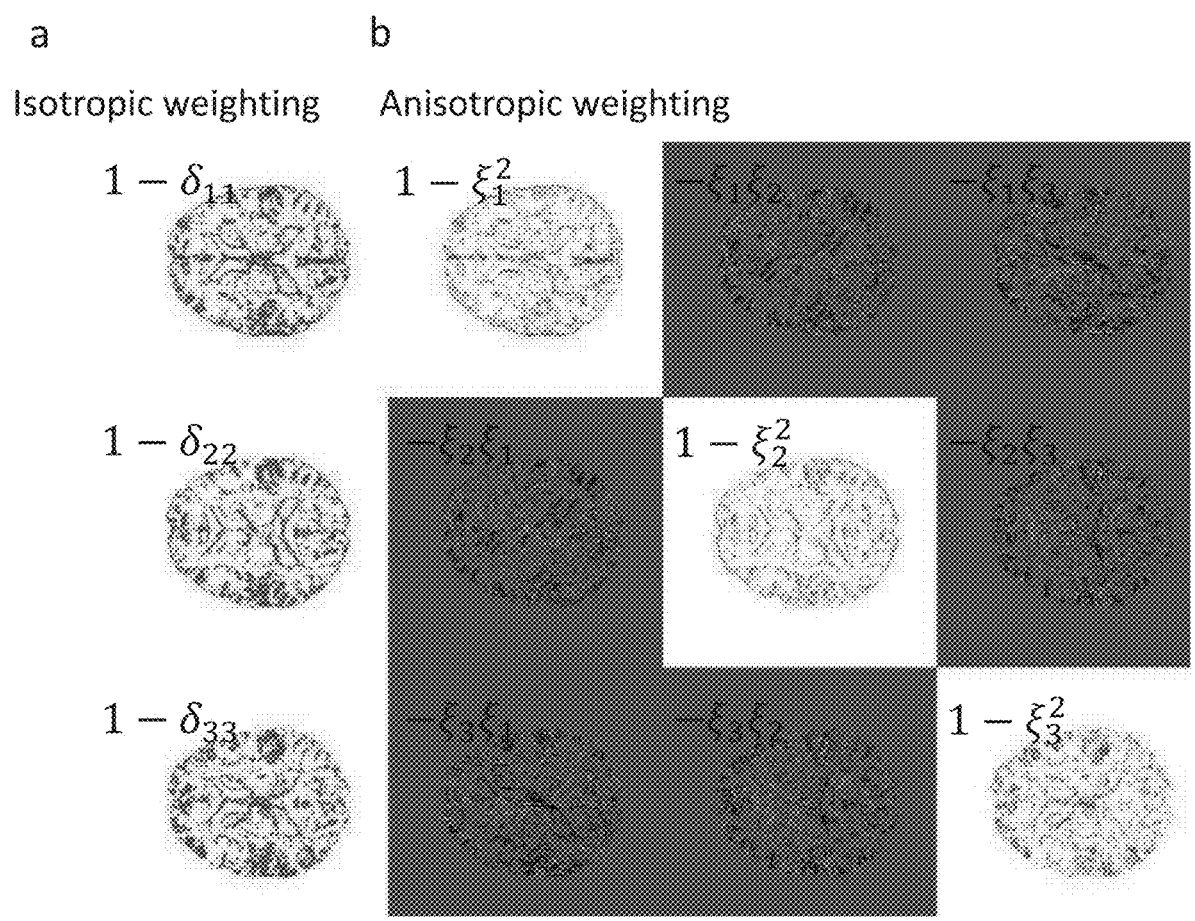
FIGS. 10a-10b (a) binary-valued isotropic weighting (first column from the left); and (b) anisotropic weighting (second to fourth columns from the left). For isotropic weighting, off-diagonal components are all zero. Values are displayed in the range of [−1, 1]. Therefore, the diagonal and off-diagonal components in (b) are in the range of [0, 1] and [−1, 1], respectively.

In anisotropic weighting, we need to determine $\xi(r)=(\xi_1(r), \xi_2(r), \xi_3(r))^T$ This boils down to computing $\delta: \Omega\to\mathbb{R}$ as defined in [15]. Once $\delta_x$, $\delta_y$, and $\delta_z$ are computed by the procedure described above in isotropic weighting, we determine $\delta$ as $\delta_x(r)\vee\delta_y(r)\vee\delta_z(r)$ for $r\in\Omega$. These two weighting methods were visualized in FIGS. 10a-10b using the Cornell MRI research group data.

As the values of $\lambda/2$, 1000 and 235 were empirically chosen using the discrepancy principle for the Cornell MRI research lab data and the QSM 2016 reconstruction challenge data, respectively. Then, in the range of 700 to 1350 (700, 750, . . . , 1350) for the Cornell MRI research group data and in the range of 164.5 to 305.5 (164.5, 176.25, . . . , 305.5) for the QSM 2016 reconstruction challenge data, the MEDI algorithm with anisotropic and isotropic weighting was performed.

The following evaluation metrics were used for QSM accuracy assessment: RMSE (root mean square error), HFEN (high frequency error norm), and SSIM (structure similarity index). We used MATLAB codes for RMSE and HFEN available at http://www.neuroimaging.at/qsm2016/pages/qsm-challenge.php, and for SSIM we used the MATLAB function (SSIM) in Image Processing Toolbox with default settings. In addition, we used what we call the degree of alignment to measure how well aligned two images are, which is defined as follows: Let u and v be scalar-valued images (e.g., functions in BV ($\Omega$; $\mathbb{R}$ )); and let $n_u$, $n_v$ denote vector fields of surface normals to u and v, respectively. Suppose that $\theta_{n_u,n_v}(r)$ is the angle between the two vector fields at $r\in\Omega$. Then, the degree of alignment (DoA) of the two vector fields is defined as $$DoA(u,v) := \frac{1}{|\Omega|}\int_\Omega |\cos\theta_{n_u,n_v}(r)|dr = \frac{1}{|\Omega|}\int_{r\in\Omega}\left|\left\langle\frac{\nabla u(r)}{\|\nabla u(r)\|_2}, \frac{\nabla v(r)}{\|\nabla v(r)\|_2}\right\rangle\right|dr,$$

where $|\cdot|$ denotes the Lebesgue measure in $\mathbb{R}$, i.e., volume. Note that the quantity DoA(u, v) is bounded below by 0 (when the two vector fields are perpendicular almost everywhere) and is bounded above by 1 (when the two vector fields are parallel—either 0 rad or $\pi$ rad). Therefore, the quantity DoA(u, v) measures how well aligned the two images u and v are in the range of [0,1] (higher indicates better alignment). To assess QSM accuracy based on mean voxel values in various brain regions, 19 circular regions of interest, each measuring 14.5 $mm^3$, were drawn on selected brain slices by a neuroradiologist with more than 20 years of experience, in the striatum (caudate nucleus, putamen, globus pallidus), thalamus, cortical gray matter, splenium of corpus callosum, frontal white matter, occipital white matter, and cerebrospinal fluid (CSF) in lateral ventricles. The mean voxel value for each ROI was calculated in MATLAB and recorded relative to the CSF mean value. For various values of regularization parameter, $\lambda$, the slope and coefficient of determination, $R^2$, were recorded for the linear regression between the MEDI derived ROI values and the COSMOS or $\chi_{33}$ derived ROI values. These fitting parameters were compared between isotropic or anisotropic weighting for MEDI 2.4. Results For the Cornell MRI research group data and for the values of $\lambda/2$ (700 to 1350), the CPU running times were approximately 38 min and 44 min for anisotropic and isotropic weighting, respectively. For the QSM 2016 reconstruction challenge data and for the values of $\lambda/2$ (164.5 to 305.5), the CPU running times were approximately 10 min for both anisotropic and isotropic weighting.

Figure 11A:
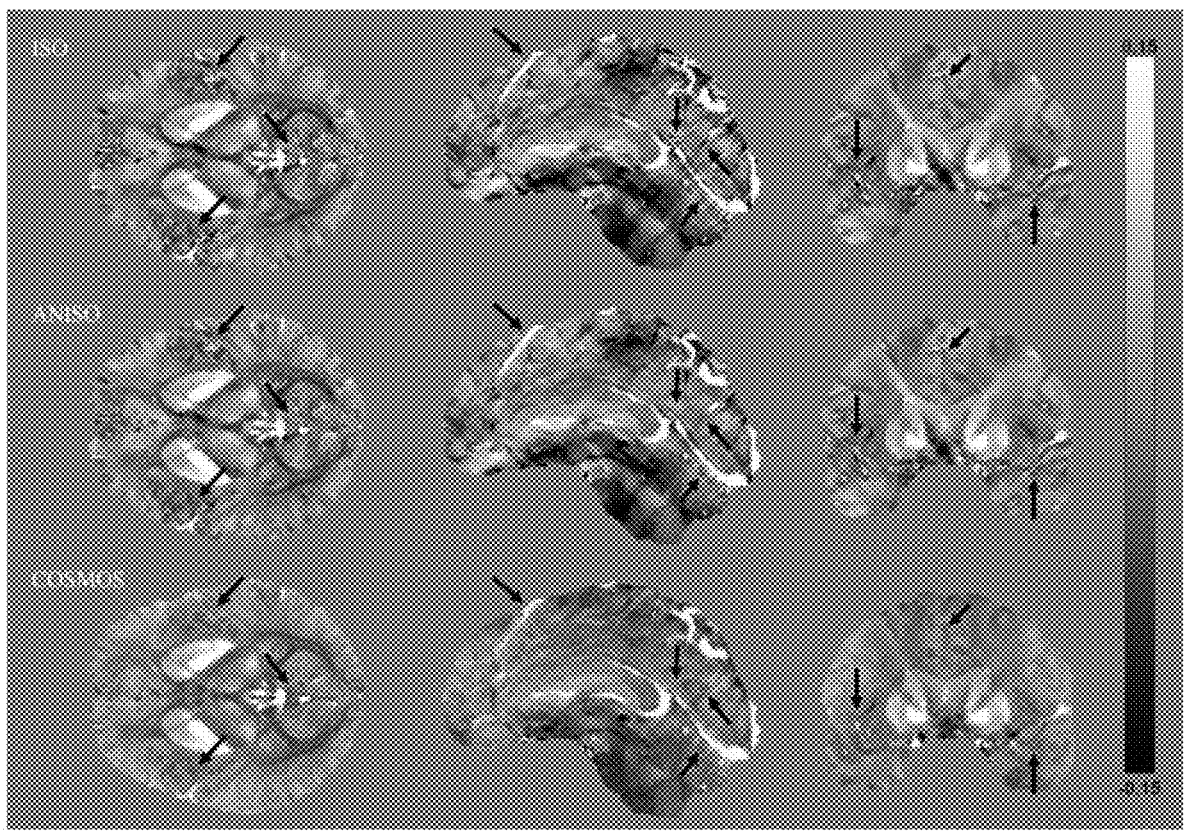
Figure 11B:
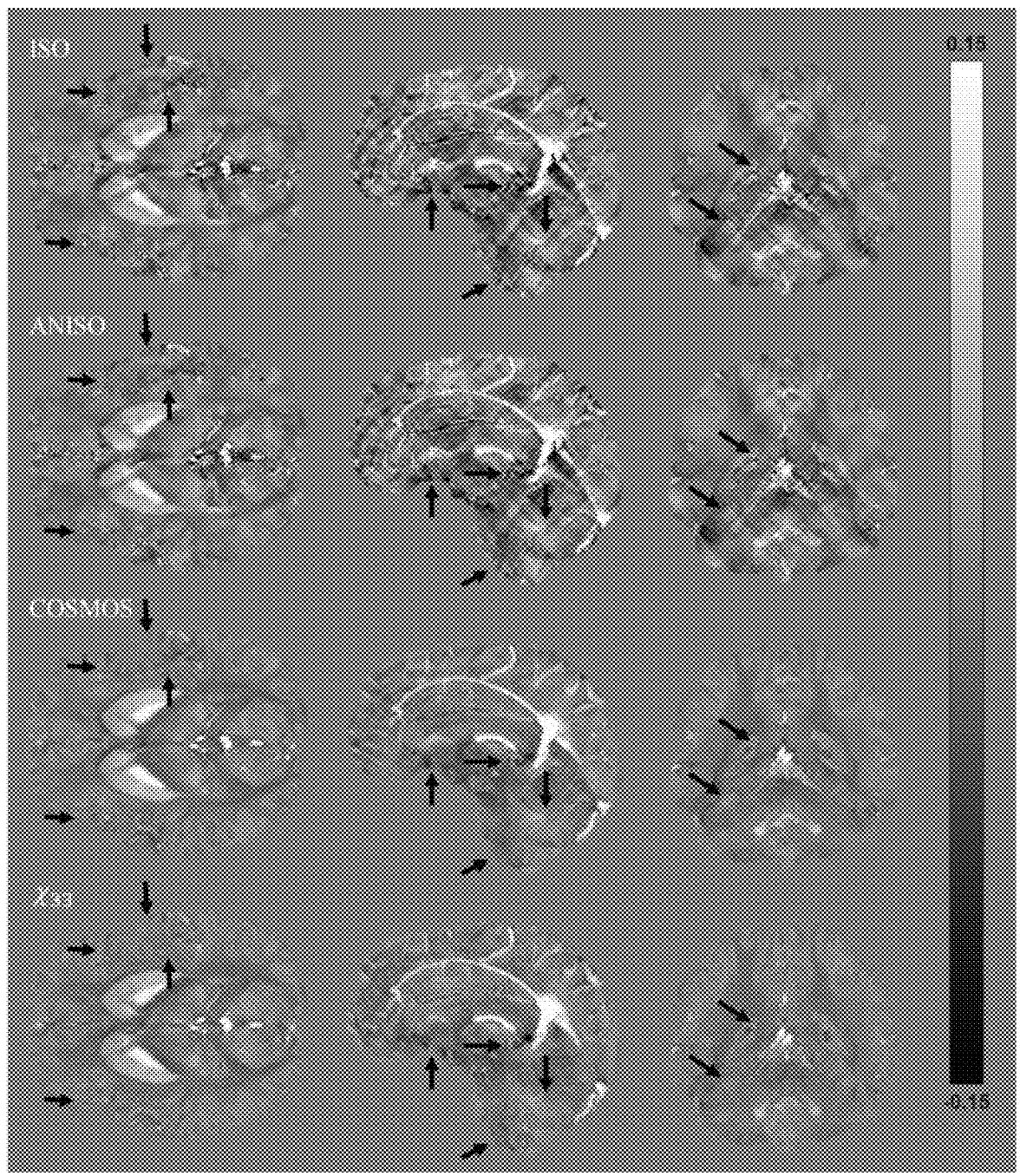

FIGS. 11a-11b shows computed susceptibility maps with anisotropic and isotropic weighting for the Cornell MRI research lab data ($\lambda/2=1000$) and the QSM 2016 reconstruction challenge data ($\lambda/2=235$) in axial, sagittal, and coronal views. Across the susceptibility maps, we see more streaking artifacts in isotropic weighting than anisotropic weighting. These artifacts are manifested as blocky spots in axial view (see first columns from the left in FIGS. 11(a) and (b)), streaks in sagittal and coronal views (see second and third columns from the left in FIGS. 11(a) and (b)). Arrows were also placed where these artifacts are conspicuous; note that streaks exhibit across the image in sagittal and coronal views. These artifacts were substantially suppressed in anisotropic weighting with respect to reference images (COSMOS or $\chi_{33}$).

Figure 12A:
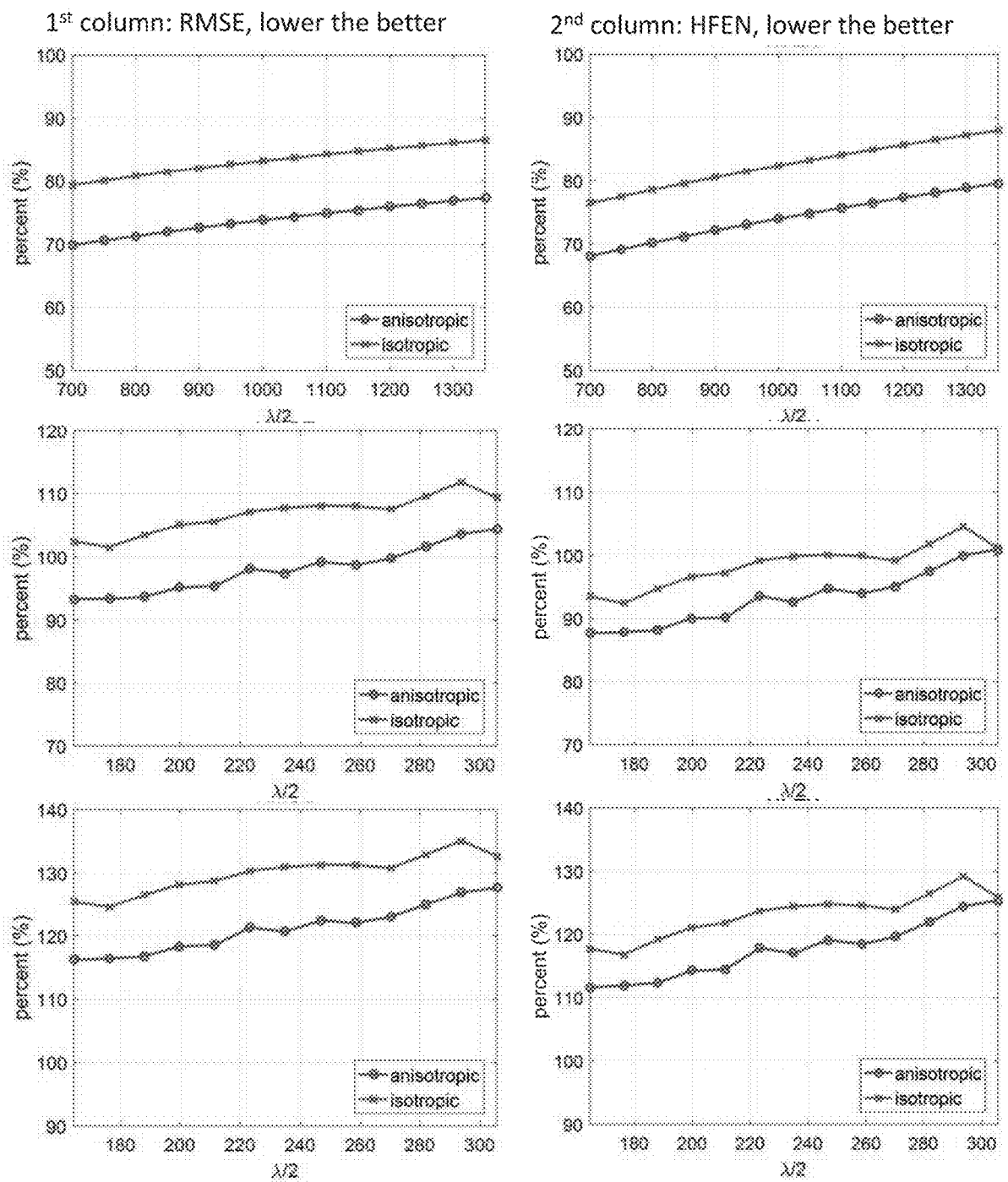
FIGS. 12a-12b. QSM accuracy assessment via global metrics. RMSE (first column in a), HFEN (second column in a), SSIM (third column in b), and DoA (fourth column in b) were plotted versus the regularization parameter (anisotropic and isotropic weighting). (first row from the top) Cornell MRI research lab data with respect to COSMOS. (second row from the top) QSM 2016 reconstruction challenge data with respect to COSMOS. (third row from the top) QSM 2016 reconstruction challenge data with respect to $\chi_{33}$ FIG. 13. QSM accuracy assessment via linear regression based on ROIs between methods and reference standards. Slopes and $R^2$ values were plotted versus regularization parameter (anisotropic and isotropic weighting). (first row from the top) Cornell MRI research lab data with respect to COSMOS. (second row from the top) QSM 2016 reconstruction challenge data with respect to COSMOS. (third row from the top) QSM 2016 reconstruction challenge data with respect to $\chi_{33}$.
Figure 12B:
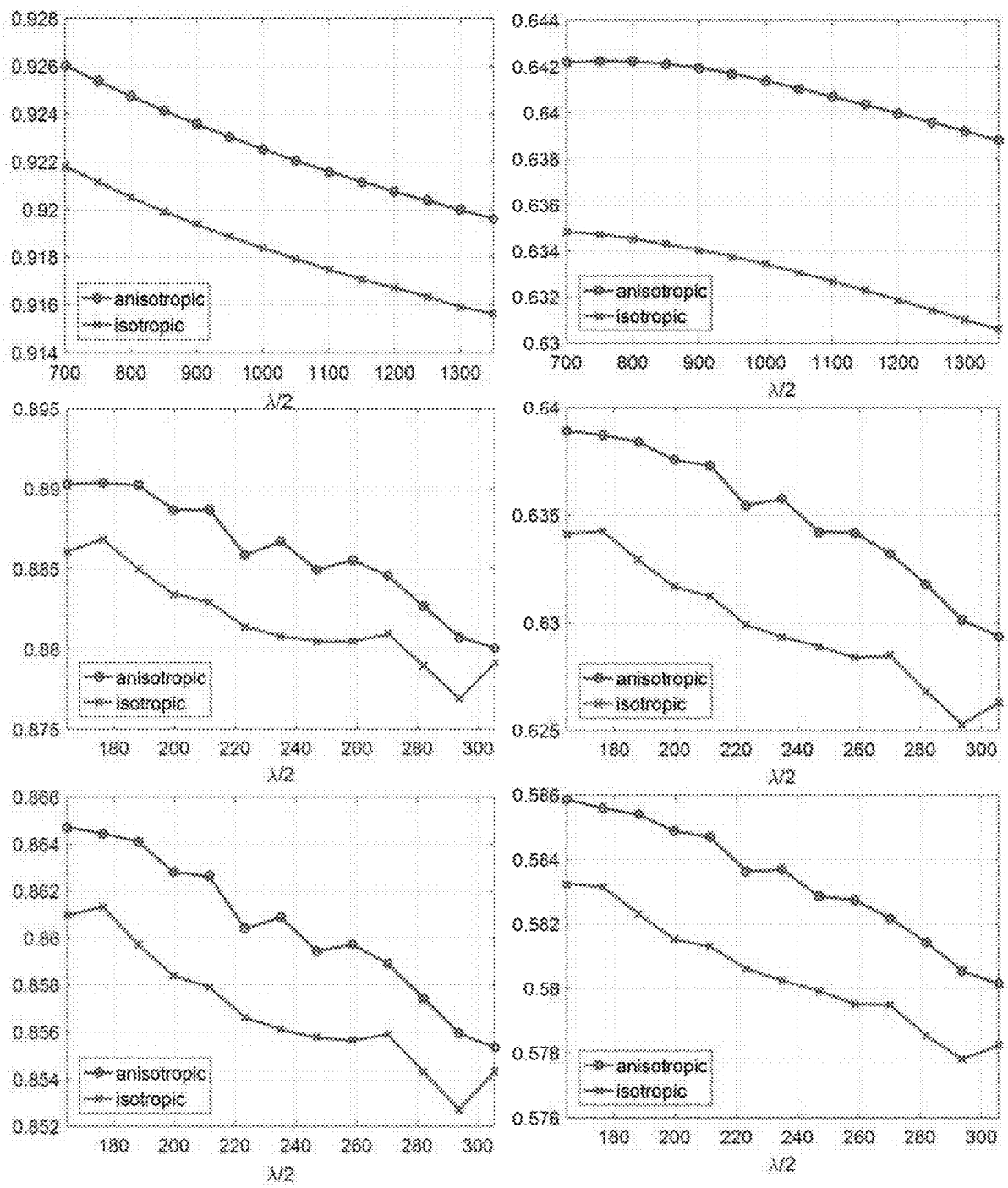

RMSE (lower is better), HFEN (lower is better), SSIM (higher is better), and the DoA (higher is better) were shown in FIGS. 12a-12b, where all the measures were plotted versus the regularization parameter $\lambda/2$. From top to bottom, each row corresponds to the Cornell MRI research group data with respect to COSMOS, the QSM 2016 reconstruction challenge data with respect to COSMOS and $\chi_{33}$. As can be clearly seen in FIGS. 12a-12b, improvements in QSM accuracy achieved by anisotropic weighting were consistent on both datasets within the range of regularization parameter. Across the range of regularization parameter, the absolute improvements were on average 9.4% in RMSE, 8.4% in HFEN, 0.4% in SSIM, and 0.8% in DoA for the Cornell URI research group data. For the QSM 2016 reconstruction challenge data, across the range of regularization parameter, the absolute improvements were 8.7% in RMSE, 5.2% in HFEN, 0.4% in SSIM, and 0.5% in DoA and 8.7% in RMSE, 5.5% in HFEN, 0.4% in SSIM, and 0.3% in DoA with respect to COSMOS and $X_{33}$, respectively.

Figure 13:
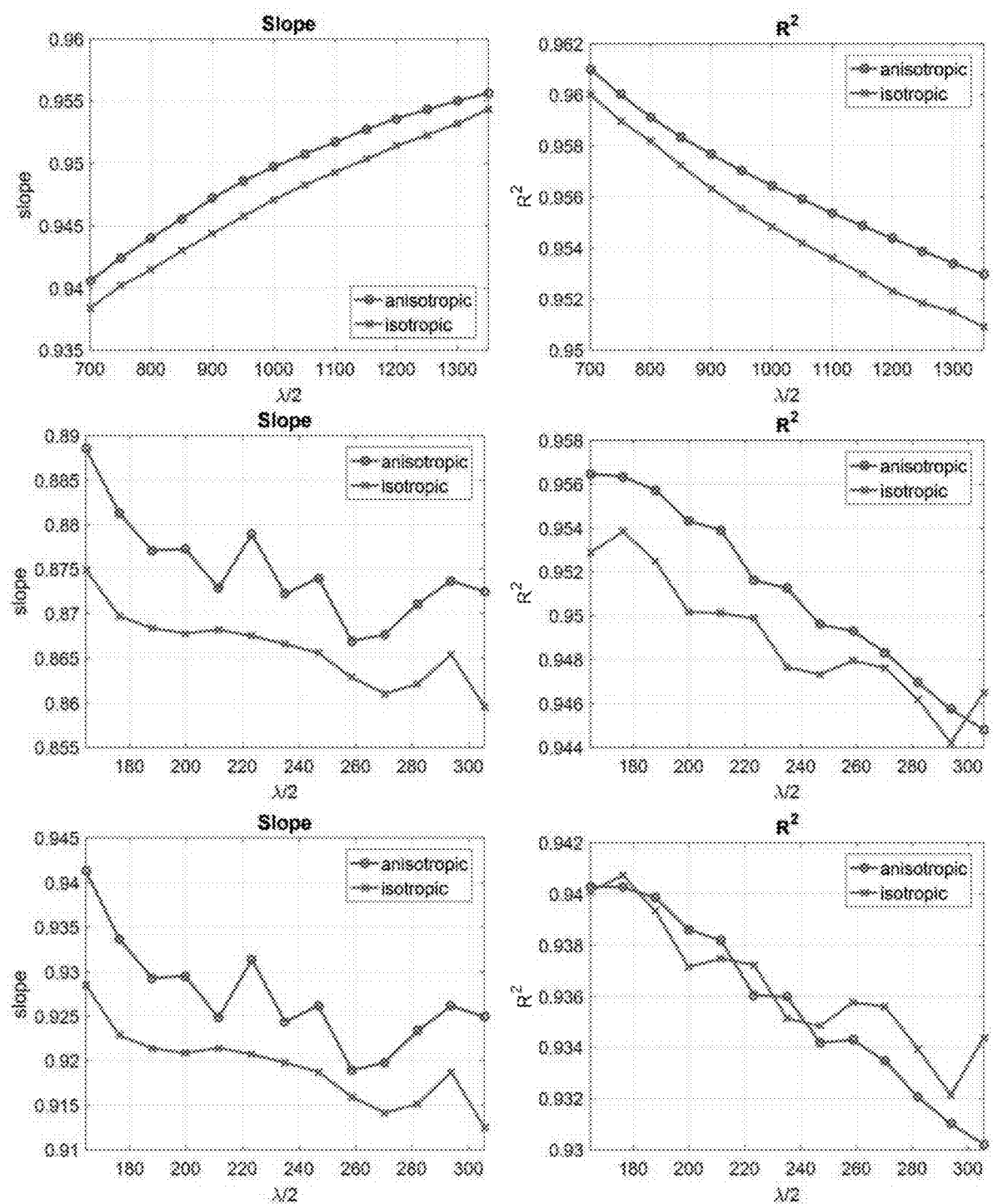

QSM accuracy was assessed in different methods (isotropic and anisotropic) via linear regression based on voxel values within ROIs between the methods and reference standards (COSMOS or $\chi_{33}$). FIG. 13 shows slope and $R^2$ versus the value of lambda for the Cornell MRI research group data (with respect to COSMOS first row from the top) and the QSM 2016 reconstruction challenge data (with respect to COSMOS and $\chi_{33}$, second and third rows from the top, respectively). Anisotropic weighting consistently achieved higher slope than isotropic weighting within the range of regularization parameter: On average, for the Cornell MRI research group data, the slopes were 0.949 and 0.947 for anisotropic and isotropic weighting, respectively. For the QSM 2016 reconstruction challenge data, the slopes with respect to $\chi_{33}$ were 0.927 and 0.919 for anisotropic and isotropic weighting, respectively. With respect to COSMOS, the slopes were 0.875 and 0.866 for anisotropic and isotropic weighting, respectively.

2.5. Conclusions

We have considered anisotropic weighting as a new structural prior in the QSM inverse problem. As opposed to isotropic weighting, anisotropic weighting imposes orientation consistency between a candidate susceptibility map and the magnitude image that is associated with the susceptibility map. In experiments, we have shown improvements in QSM accuracy in terms of both quantitative measures and image quality within a wide range of regularization parameter.

The notion of anisotropic weighting considered in this paper was widely studied in a seminal monograph on anisotropic diffusion in image processing and in the context of vector-valued image processing whose main focus is to retrieve common edges across the channels (e.g., RGB) and suppress random noise. Recently, a similar work has been studied in image processing in the name of directional total variation and another work has been published in the context of multicontrast MRI for fast imaging where structural information in $T_1$ weighted images were used for the reconstruction of $T_2$ weighted images with sparse samples. The proposed method is in line with these works; but is new in quantitative susceptibility mapping.

In FIGS. 11a-11b, we observe more visual artifacts in isotropic weighting than anisotropic weighting, which is clearly inconsistent with the reference images (COSMOS and $\chi_{33}$). An intuitive explanation for this is as follows: Consider two 2D vectors $\nabla \text{Mag}(r_0)=(1,1)^T$ and $\nabla \chi(r_0)=(\cos \theta(r_0), \sin \theta(r_0))^T$ at $r=r_0$, where $\theta(r_0)$ is the angle from the x-axis at $r=r_0$. Then, the following is penalized in anisotropic weighting:

$$\left\| \begin{pmatrix} 1/2 & -1/2 \\ -1/2 & 1/2 \end{pmatrix} \begin{pmatrix} \cos\theta(r_0) \\ \sin\theta(r_0) \end{pmatrix} \right\|_1 = \left| \frac{1}{2}\cos\theta(r_0) - \frac{1}{2}\sin\theta(r_0) \right| + \left| -\frac{1}{2}\cos\theta(r_0) + \frac{1}{2}\sin\theta(r_0) \right|.$$

Therefore, when $\theta(r_0)=\pi/4$ and $5\pi/4$, there is no penalty (maximally allowed); when $\theta(r_0)=3\pi/4$ and $7\pi/4$, penalty is maximized (maximally disallowed). In isotropic weighting, on the other hand, the following is regularized:

$$\left\| \begin{pmatrix} 1-\delta_x(r_0) & 0 \\ 0 & 1-\delta_y(r_0) \end{pmatrix} \begin{pmatrix} \cos\theta(r_0) \\ \sin\theta(r_0) \end{pmatrix} \right\|_1 = |(1-\delta_x(r_0))\cos\theta(r_0)| + |(1-\delta_y(r_0))\sin\theta(r_0)|,$$

where $\delta_x(r_0)$ and $\delta_y(r_0)$ are edge indicators for x and y directions, respectively. Therefore, we have $|\sin \theta(r_0)|$, $|\cos \theta(r_0)|$, and 0 penalties for the x, y, and both x and y directional edges, respectively. Clearly, this does not take into account orientation consistency for instance if both x and y directional edges are detected, every possible direction of $\nabla_\chi(r_0)$, i.e., $\theta(r_0)$ is allowed with no penalty. This additional "adaptive penalization" in anisotropic weighting appears to have suppressed such visual artifacts originated from orientation inconsistency.

The CPU time gaps between anisotropic and isotropic weighting for the Cornell MRI research group data and the QSM 2016 reconstruction challenge data were approximately 6 min and few seconds, respectively. Anisotropic weighting was faster on the Cornell MRI research group data and was as fast as isotropic weighting on the QSM 2016 reconstruction challenge data. Anisotropic weighting involves 3×3 full matrix multiplications as opposed to 3×3 diagonal matrix multiplications for isotropic weighting leading to few more seconds at each outer iteration of the Gauss-Newton conjugate gradient method. However, oftentimes anisotropic weighting converged faster with less number of outer iterations, which explains the fact that anisotropic weighting is as fast as isotropic weighting.

To devise a structural prior that takes into account the biophysical model behind QSM is the cornerstone of the success for regularization-based inversion methods. As seen throughout the paper, the anisotropic weighting approach outperforms isotropic weighting and its implementation is very simple. We believe that the proposed approach will be an important step towards an optimal field decomposition method; albeit unknown yet.

In summary, incorporating anisotropic weighting into the regularization term of MEDI improves QSM accuracy by taking into account orientation consistency which is missing in isotropic weighting.

3. Primal Dual Solver

In this section, we describe the primal dual solver for the QSM problem, which would improve both accuracy and speed for evaluating the derivative of the L1 norm term.

3.1. Introduction

Bayesian MAP estimation has been used increasingly in MRI to reconstruct images from incomplete noisy data with a likelihood to model noise and a prior probability to compensate for undersampling. Its application in image reconstruction often leads to minimization problems that can be commonly solved by using the Gauss-Newton conjugate gradient (GNCG) algorithm. This is the case for quantitative susceptibility mapping (QSM), where a structural prior is used to identify a solution with minimal streaking (morphology enabled dipole inversion or MEDI). The structural prior imposes the spatial consistency of edges (gradients) between a known tissue image and the targeted tissue susceptibility map.

The goal of this paper is to investigate the effects of the specific implementation of this gradient $L^1$-norm prior term on QSM quality. First, typical GNCG implementations employ numerical conditioning that slightly modify this prior term smoothing the $L^1$-norm, thus solving an approximated energy function. While the effects of this conditioning have been investigated in the context of image denoising, an analysis for QSM has not been performed yet. An alternative method, the primal-dual algorithm, will be used for comparison. The latter algorithm has been used to compute generalized total variation in Bayesian MRI and in QSM. Second, a central difference scheme has been used to implement the gradient operator in the prior term. This can lead to checkerboard artifacts. An alternative method, a forward difference scheme, will be used for comparison. Accordingly, this paper will evaluate the primal-dual formulation of QSM using the Chambolle-Pock algorithm with a forward gradient implementation and compare this with the GNCG method with a central gradient implementation.

3.2. Theory

Here, we outline a spatially continuous formulation for the QSM energy minimization problem to describe the dual definition of the anisotropic total variation, instead of the approximate derivative used in GNCG. Details on the primal-dual algorithm can be found in the MEDI toolbox (http://weill.cornell.edu/mri/pages/qsm.html).

A Spatially Continuous Formulation of MEDI

Currently, QSM has been formulated as a discrete energy minimization problem to estimate the underlying susceptibility distribution. Its continuum limit can be expressed by the following variational model:

$$\hat{u} \in \operatorname{argmin}\left\{u \in BV(\Omega; \mathbb{R}) : \int_\Omega |MDu|_1 + \frac{\lambda}{2}\int_\Omega |W(Tu-b)|^2\right\}. \quad [18]$$

Here, the susceptibility function $u: \Omega \to \mathbb{R}$ ($L^1$-integrable) is estimated from the measured local field $b: \Omega \subset \mathbb{R}^3) \to \mathbb{R}$ ($\Omega$ is a Lipschitz domain). The solution space $BV(\Omega; \mathbb{R})$ of bounded variation (BV) allows the existence of jumps (sharp edges). The objective consists of two energy terms, data fidelity and regularization, as in the discrete formulation. The data fidelity term involves a linear operator T defined by $Tu(r)=(d*u)(r)$, $r \in \Omega$, where d and * are the unit dipole kernel and the convolution operation, respectively. Let $L^1$ be the space of absolutely integrable ($L^1$-integrable) functions. The map $W: L^1 \to L^1$ compensates for the non-uniform phase noise (SNR weighting). The regularization term imposes spatial regularity using anisotropic weighted total variation (TV) with an edge map $M: [L^1(\Omega; \mathbb{R})]^3 \to [L^1(\Omega; \mathbb{R})]^3$ that is extracted from the corresponding magnitude image. The gradient operator D is understood in the sense of distribution. The tuning parameter $\lambda > 0$ balances data fidelity and regularization, which can be determined by using the discrepancy principle or the L-curve method, etc. Based on this spatially continuous formulation of MEDI, the existence of a minimizer can be established using the BV deblurring theory. The formulation leads us to functional minimization where the susceptibility u is a function of r. Then, the susceptibility denoted by $\chi$ commonly used in QSM literature is given by discretizing u. Our interest here is to compute such a minimizer, and we start with the GNCG algorithm.

Gauss Newton Conjugate Gradient (GNCG)

The GNCG method assumes that u is differentiable (technically u is assumed to be in the Sobolev space $W^{1,1}$), which allows us to derive the Euler-Lagrange equation associated with the energy functional as follows:

$$\sum_{\ell=1}^{3} \frac{\partial}{\partial r_\ell}\left(\frac{M^{r_\ell}(r) D^{r_\ell} u(r)}{|M^{r_\ell}(r) D^{r_\ell} u(r)|}\right) - \lambda(WT)*(W(Tu-b)) = 0, \forall r \in \operatorname{int} \Omega, \quad [19]$$

where $(WT)^*$ is the adjoint of WT. The Euler-Lagrange equation, however, exhibits degeneracy when $|M^{r_\ell}(r) D^{r_\ell} u(r)|=0$ so that numerical conditioning is required for computational purposes: $|M^{r_\ell}(r) D^{r_\ell} u(r)|$ is replaced with $\sqrt{|M^{r_\ell}(r) D^{r_\ell} u(r)|^2 + \epsilon}$ for $\ell=1, 2$, and 3 and a small $\epsilon > 0$. As a consequence, this conditioning deviates from the definition of TV for $L^1$-integrable functions where image edges are modeled as the set of discontinuities. Therefore, the algorithm solves a slightly different objective that involves the conditioning parameter $\epsilon$.

Primal-Dual Formulation

Similar to the distributional derivative for a function with discontinuities, we can derive a generalized definition of anisotropic weighted TV in the space $L^1$ of integrable functions $$\int_\Omega |MDu|_1 = \sup\{-\int_\Omega u \operatorname{div}(M^*\xi) dr | \xi \in C_c^1(\Omega, \mathbb{R}^3), \|\xi\|_\infty \ldots \leq 1, \forall r \in \Omega\} \quad [20]$$

where $C_c^1$ is the set of continuously differentiable functions with compact support, $\|\xi(r)\|_\infty = \max\{|\xi^x(r)|, |\xi^y(r)|, |\xi^z(r)|\}$ and $M^*$ is the adjoint of M. $\xi$ is the so-called dual variable with the constraint of pointwise maximum norm, the divergence of a vector is denoted by div, and the supremum of a set is denoted by sup. Note that the discontinuities are allowed in u in the above dual formulation. Since $\frac{1}{2}\|\cdot\|_2^2$ is self-conjugate and $(\alpha H)^* = \alpha H^*(\cdot/\alpha)$ for $H: L^2 \to (-\infty, +\infty]$ and $\alpha > 0$, the data term can be dualized as follows:

$$\frac{\lambda}{2}\|W(Tu-b)\|_2^2 = \sup\left\{v \in L^2 : \langle W(Tu-b), v \rangle_{L^2} - \frac{1}{2\lambda}\|v\|_2^2\right\}. \quad [21]$$

where $\langle \rangle_2$ is the inner product defined in the space of square integrable functions, i.e., $L^2(\Omega; \mathbb{R})$. Therefore, the minimization problem [18] can be rewritten using [20] and [21] resulting in the so-called primal-dual formulation:

$$\hat{u} \in \operatorname{argmin} \quad [22]$$
$$\left\{\sup\left\{(\xi, v) \in C_c^1 \times L^2 :: -\int_\Omega u \operatorname{div}(M^*\xi) dr + \langle W(Tu-b), v \rangle_{L^2} - \iota_P(\xi) - \frac{1}{2\lambda}\|v\|_2^2\right\}\right\},$$

where the indicator function $\iota_P(\xi)$ of a set $P \subset C_c^1$ is defined as $$\iota_P(\xi) = \begin{cases} 0 & \text{if } \xi \in P \\ +\infty & \text{otherwise} \end{cases},$$

with convex set $$P = \{\xi \in C_c^1(\Omega; \mathbb{R}^3) : \|\xi(r)\|_\infty \leq 1, \forall r \in \Omega\}. \quad [23]$$

This is a saddle-point problem with a convex constraint. Under the assumption that there exists a saddle-point satisfying solution [22], a provably convergent algorithm can be applied to compute such an optimal point. Among others, we make use of the fast primal-dual (PD) algorithm proposed by Chambolle and Pock. In the following, we have provided a discrete setting for [22] and implementation details on the PD algorithm to compute an optimal susceptibility map. Note that GNCG now can be viewed as the primal approach.

Discrete Setting

To compute an optimal solution of the saddle-point problem [22], first we provide a discrete setting. Let us consider a three-dimensional regular Cartesian grid of size $N_x \times N_y \times N_z$ as follows:

$$\{(ih_x, jh_y, kh_z) : 1 \leq i \leq N_x, 1 \leq j \leq N_y, 1 \leq i \leq N_z\},$$

where $h_x$, $h_y$, and $h_z$ denote the voxel size, and (i, j, k) the voxel location. Define a scalar product on $H = \mathbb{R}^{N_x} \times \mathbb{R}^{N_y} \times \mathbb{R}^{N_z}$ as $$\langle u, v \rangle_H = \sum_{i,j,k} u_{i,j,k} v_{i,j,k}, \; u, v \in H.$$

For $u \in H$, the discrete gradient $\nabla u$ is defined by $$(\nabla u)_{i,j,k} = ((\nabla u)^x_{i,j,k}, (\nabla u)^y_{i,j,k}, (\nabla u)^z_{i,j,k}) \text{ where}$$

$$(\nabla u)^x_{i,j,k} = \begin{cases} (u_{i+1,j,k} - u_{i,j,k})/h_x & \text{if } i < N_x, \\ 0 & \text{if } i = N_x; \end{cases}$$

$$(\nabla u)^y_{i,j,k} = \begin{cases} (u_{i,j+1,k} - u_{i,j,k})/h_y & \text{if } j < N_y, \\ 0 & \text{if } j = N_y; \end{cases}$$

$$(\nabla u)^z_{i,j,k} = \begin{cases} (u_{i,j,k+1} - u_{i,j,k})/h_z & \text{if } k < N_z, \\ 0 & \text{if } k = N_z. \end{cases}$$

The gradient vector $\nabla u$ is a vector in the finite dimensional real vector space $K = U \times H \times H$ where a scalar product is given as follows:

$$\langle \xi, \zeta \rangle_K = \sum_{i,j,k} \xi^x_{i,j,k} \zeta^x_{i,j,k} + \xi^y_{i,j,k} \zeta^y_{i,j,k} + \xi^z_{i,j,k} \zeta^z_{i,j,k}, \; \xi, \zeta \in K.$$

Notice that the forward difference scheme with the Neumann boundary condition is used for the discrete gradient. Now, we define a linear map $M: K \to K$ such that $$\xi_{i,j,k} \mapsto (M\xi)_{i,j,k} = (M_{i,j,k}^x \xi^x_{i,j,k}, M_{i,j,k}^y \xi^y_{i,j,k}, M_{i,j,k}^z \xi^z_{i,j,k})$$

for all i, j, and k. Then, the following discrete dual definition of [20] is straightforward $$\|M \nabla u\|_1 = \sup\{u, \nabla^* M^* \xi\}_H : \xi \in K, \|\xi_{i,j,k}\|_\infty \le 1, \forall i,j,k\},$$

where $\nabla^*: K \to H$ and $M^*: K \to K$ are the adjoints of $\nabla$ and M, respectively; i.e., $\langle M \nabla u, \xi \rangle_K = \langle u, \nabla^* M^* \xi \rangle_H$. The $\infty$-norm $\|\cdot\|_\infty$ is defined as $$\|\xi_{i,j,k}\|_\infty = \max\{|\xi^x_{i,j,k}|, |\xi^y_{i,j,k}|, |\xi^z_{i,j,k}|\}.$$

From the relationship $\langle u, \nabla^* M^* \xi \rangle_H = \langle M \nabla u, \xi \rangle_K$ and the discrete setting for $M \nabla u$, the following discretization of the adjoint operator $\nabla^* \xi$ is easy to derive:

$$(\nabla^* M^* \xi)_{i,j,k} = \begin{cases} ((M^*)^x_{i,j,k} \xi^x_{i,j,k} - (M^*)^x_{i-1,j,k} \xi^x_{i-1,j,k})/h_x & \text{if } 1 < i < N_x, \\ (M^*)^x_{i,j,k} \xi^x_{i,j,k}/h_x & \text{if } i = 1, \\ -(M^*)^x_{i-1,j,k} \xi^x_{i-1,j,k}/h_x & \text{if } i = N_x; \end{cases} +$$

$$\begin{cases} ((M^*)^y_{i,j,k} \xi^y_{i,j,k} - (M^*)^y_{i,j-1,k} \xi^y_{i,j-1,k})/h_y & \text{if } 1 < j < N_y, \\ (M^*)^y_{i,j,k} \xi^y_{i,j,k}/h_y & \text{if } j = 1, \\ -(M^*)^y_{i,j-1,k} \xi^y_{i,j-1,k}/h_y & \text{if } j = N_y; \end{cases} +$$

$$\begin{cases} ((M^*)^z_{i,j,k} \xi^z_{i,j,k} - (M^*)^z_{i,j,k-1} \xi^z_{i,j,k-1})/h_z & \text{if } 1 < k < N_z, \\ (M^*)^z_{i,j,k} \xi^z_{i,j,k}/h_z & \text{if } k = 1, \\ -(M^*)^z_{i,j,k-1} \xi^z_{i,j,k-1}/h_z & \text{if } k = N_z. \end{cases}$$

Note that the adjoint operator of the discrete gradient is the negative divergence, i.e., $\nabla^* M^* \xi = -\text{div}(M^* \xi)$, which is discretized by the backward difference scheme with the Dirichlet boundary condition.

Primal-Dual Algorithm

The function spaces $C_c^1$ and $L^2$ are replaced by K and H, respectively; and, the convex set [23] is discretized as follows:

$$P = \{\xi_{i,j,k} \in K : \|\xi_{i,j,k}\|_\infty \le 1, \forall i,j,k\}.$$

Then, a discrete formulation of [22] is now straightforward. This discrete primal-dual formulation can be efficiently solved by a provably convergent saddle-point solver. Here, we apply a first-order primal-dual algorithm whose convergence was proved by Chambolle and Pock with an overrelaxation step. The algorithm is basically read as alternating gradient descent with respect to the primal variable u followed by the proximal operator associated with $\langle W(Tu-b), v \rangle_H$ and gradient ascent with respect to the dual variables $\xi$ and v followed by the proximal operators associated with $\iota_P(\xi)$ and $$\frac{1}{2\lambda} \|v\|_2^2.$$

Let us define G as $\langle W(Tu-b), v \rangle_H$, then the proximal operator of the scaled function $\tau G$, $\tau > 0$ is given as $$u = \text{prox}_{\tau G}(\tilde{u}) \Leftrightarrow u = \tilde{u} - \tau T^* W^* v \Leftrightarrow u = \tilde{u} - \tau \mathcal{F}^{-1}(\overline{\mathcal{F}(d)} \odot \mathcal{F}(W^* v)),$$

where $\mathcal{F}(\bullet)$ and $\mathcal{F}^{-1}(\bullet)$ denote the fast Fourier transform (FFT) and inverse FFT, respectively. $\overline{\mathcal{F}(d)}$ is the complex conjugate of $\mathcal{F}(d)$ and the operation $\odot$ is the pointwise multiplication. Note that at each iteration, only one FFT and one inverse FFT are required to perform for this operator; $\overline{\mathcal{F}(d)}$ is computed in advance. On the other hand, the proximal operators of the scaled function $\sigma \iota_P(\xi)$ and $$\frac{\sigma}{2\lambda} \|v\|_2^2$$

are given as $$\xi = \text{prox}_{\sigma \iota_P}(\tilde{\xi}) \Leftrightarrow \xi_{i,j,k} = \frac{\tilde{\xi}_{i,j,k}}{\max(1, |\tilde{\xi}_{i,j,k}|)},$$

$$v = \text{prox}_{\frac{\sigma}{2\lambda} \|\cdot\|_2^2}(\tilde{v}) \Leftrightarrow v_{i,j,k} = \frac{\tilde{v}_{i,j,k}}{1 + \sigma/\lambda},$$

for all i, j, and k. Finally, we describe the primal-dual algorithm as follows:

$$\xi^{n+1} = \text{prox}_{\sigma \iota_P}(\xi^n + \sigma M \nabla \bar{u}^n),$$

$$v^{n+1} = \text{prox}_{\frac{\sigma}{2\lambda} \|\cdot\|_2^2}(v^n + \sigma W(T\bar{u}^n - b)),$$

$$u^{n+1} = \text{prox}_{\tau G}(u^n - \tau \nabla^* M \xi^{n+1}),$$

$$\bar{u}^{n+1} = 2u^{n+1} - u^n;$$

for n=0, ..., N−1. Again, to update v at each iteration one FFT and one inverse FFT are required. As initialization, we choose $(u^0, \xi^0) \in H \times K$ and set $\bar{u}^0 = u^0$. The primal and dual step sizes $\tau$ and $\sigma$ are chosen such that $\tau \sigma \le 1/\|M\nabla\|^2$ to ensure the convergence of the algorithm. Since $0 \le M_{i,j,k}^x \le 1$, $0 \le M_{i,j,k}^y \le 1$, and $0 \le M_{i,j,k}^z \le 1$, one has:

$$\|M\nabla\| = \sqrt{\frac{4}{(h_x)^2} + \frac{4}{(h_y)^2} + \frac{4}{(h_z)^2}}.$$

3.3. Materials and Methods

Here we describe experimental details to implement and evaluate the prima dual QSM with the forward gradient.

Dataset Descriptions

A simulated brain, a gadolinium (Gd) phantom, in vivo brain MM data in 4 healthy subjects, and ex, vivo brain blocks were used for experimental validation of the implementations using as reference the ground truth when available (simulation and Gd concentration) and COSMOS for the healthy subjects and brain blocks. The simulated brain and one set of the in vivo brain MRI data were downloaded from http://weill.cornell.edu/mri/pages/qsm.html. The rest of the in vivo data were extracted from. For phase preprocessing, a temporal unwrapping of the phase was performed in each voxel followed by a weighted least-squares fit of the temporally unwrapped phases in each voxel over TE. Then, a magnitude map guided spatial unwrapping algorithm was applied. The local field is then extracted by the projection onto dipole fields (PDF) algorithm. Note that the white matter of the simulated brain is piecewise smooth, and the rest of the brain (gray matter, etc.) is piecewise constant.

Excised brain blocks from three postmortem control brains and three postmortem Parkinsonian brains (Yale-New Haven hospital, New Haven, Conn.) were fixed and embedded in 1% agarose gel. The brain blocks were scanned using a 3T clinical MRI system (GE Healthcare, Milwaukee, Wis.) using a standard 8 channel head coil. Multiple-echo 3D gradient echo (GRE) data were acquired using the following parameters: 0.4 mm isotropic resolution, TE=4.3 ms, $\Delta$TE=4.8 ms, #TE=11, TR=74.2, BW=62.5 kHz, FA=20°. Three in-plane orientations ($\Delta\phi$=60°) were acquired. For phase processing, we used a temporal fitting method and a spatial phase unwrapping algorithm.

Central and Forward Difference Schemes

Let $h_x$, $h_y$, and $h_z$ denote the discretization widths, or voxel size, and (i,j,k) denote the indices of the discrete locations ($ih_x$, $jh_y$, $kh_z$) in the (volumetric) image domain; see the above for implementation details. Then, a discrete version of the anisotropic TV of u based on the central difference scheme for the gradient operator is defined by $$J_c(u) := \sum_{i,j,k} \left|\frac{u_{i+1,j,k} - u_{i-1,j,k}}{2h_x}\right| + \left|\frac{u_{i,j+1,k} - u_{i,j-1,k}}{2h_y}\right| + \left|\frac{u_{i,j,k+1} - u_{i,j,k-1}}{2h_z}\right|,$$

and another discrete version of the anisotropic TV of u based on the forward difference scheme for the gradient operator is defined by $$J_f(u) := \sum_{i,j,k} \left|\frac{u_{i,j,k} - u_{i-1,j,k}}{h_x}\right| + \left|\frac{u_{i,j,k} - u_{i,j-1,k}}{h_y}\right| + \left|\frac{u_{i,j,k} - u_{i,j,k-1}}{h_z}\right|.$$

Then, a discrete version of the anisotropic weighted TV is straightforward GNCG is implemented using the central difference scheme (GNCG-C) and the forward difference scheme (GNCG-F). PD is implemented using the forward difference scheme.

Parameter Settings for GNCG and PD

For GNCG, numerical conditioning was set to $\epsilon=10^{-6}$, the maximum number of inner iterations (nested CG loop) was 100, the maximum number of outer iterations was 20, and the tolerance for the nested CG loop and for the relative update norm $\|u^{k-1} - u^k\|/\|u^k\|$, with $u^k$ the solution at the kth outer iteration, were both set to 1%. For the PD algorithm, the relative update norm was set to 0.0001% and we set $\tau = 1/(\sigma\|M\nabla\|^2)$ to ensure convergence, where $\sigma = \|M\nabla\|^2$ for ex vivo brain slices and $\sigma = \|M\nabla\|^4$ for the rest of the dataset. These algorithms were implemented in Matlab R2015b on an Intel Core i7 3.30 GHz CPU with 64 GB of memory. Additionally, PD was implemented in MATLAB (unoptimized) that supports GPU computing and was run on NVIDIA GPUs (NVIDIA GeForce GTX 750 Ti and TITAN X).

Convergence Behavior

GNCG-C, GNCG-F, and PD were run with various parameter settings ($\epsilon$ for GNCG and $\tau$ and $\sigma$ for PD) on a simulated brain. Stopping criteria for these algorithms were set to be tighter than previously described to allow for investigation of the convergence behavior of each algorithm. To this end, we computed the relative norm defined by $\|u^k - u^*\|_2/\|u^*\|_2$, where $u^*$ is the ground truth, at each iteration k during optimization Quantitative Analysis The COSMOS image for each in vivo and ex vivo data set was loaded into the ITK-SNAP image processing program and regions of interest (ROIs) were drawn. ROIs for the in vivo data included the cortex, deep gray matter structures (red nucleus, substantia nigra, caudate nucleus, putamen, globus pallidus) and white matter regions (splenium of corpus callosum, frontal white matter, occipital white matter). ROIs for ex vivo data included the cortex, putamen, globus pallidus, red nucleus, substantia nigra and subthalamic nucleus.

Linear regression was performed by fitting the regression line, $X = k_1 X_{COSMOS} + b$, where X was the set of ROI mean values for all subjects for either GNCG-F or PD and) $X_{COSMOS}$ was the set of corresponding COSMOS values. The slope $k_1$, intercept b, and coefficient of determination $R^2$ were recorded for each regression. To further assess agreement between COSMOS and the two reconstruction methods, Bland-Altman plots were drawn to determine the mean difference (bias) and 95% limits of agreements.

3.4. Results

Our results are organized according to convergence analysis, gadolinium phantom, ex vivo brain slabs, and in vivo imaging.

Convergence Behavior

Figure 14:
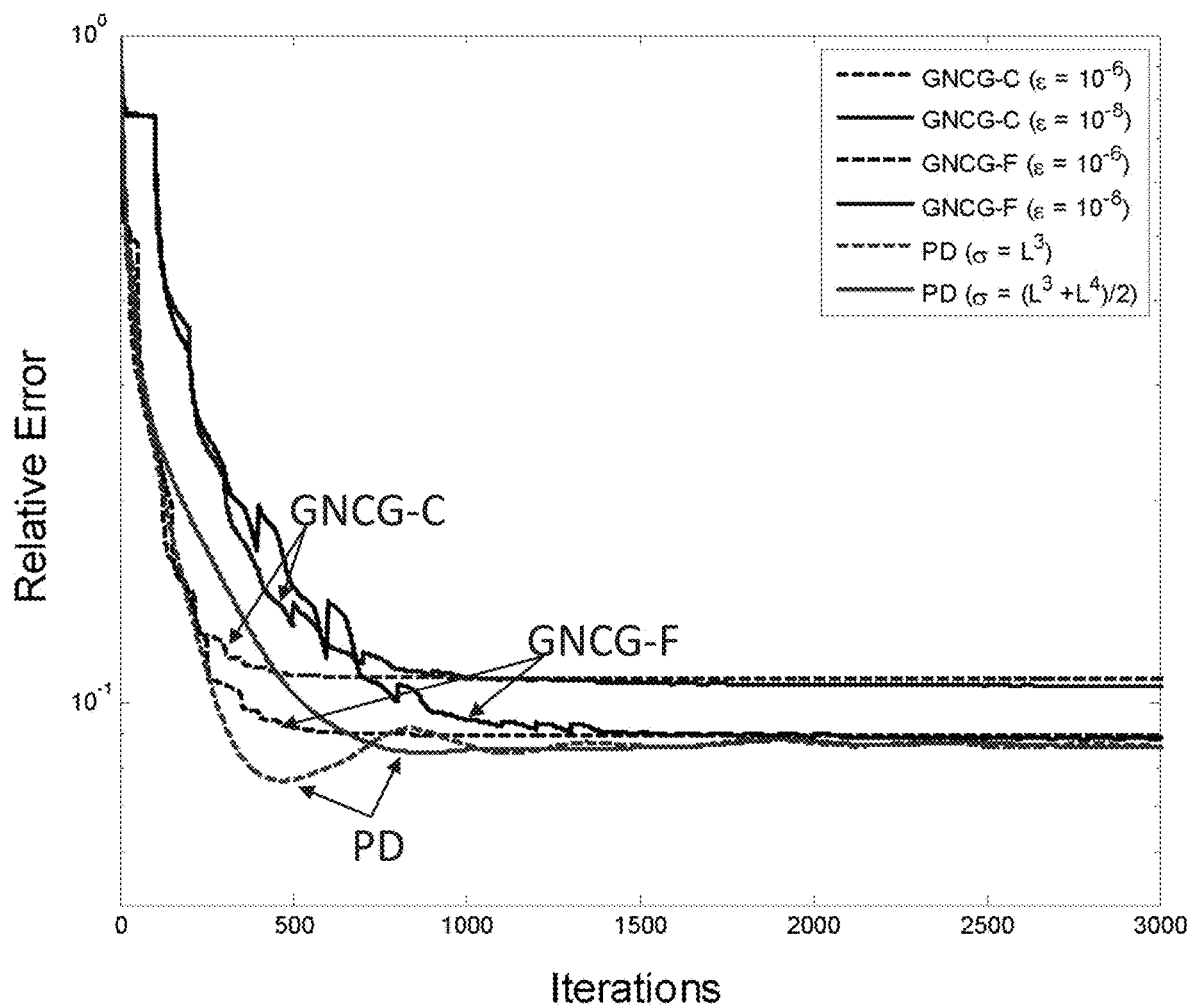
FIG. 14. Convergence behavior of Gauss-Newton conjugate gradient (GNCG) with the central difference scheme (GNCG-C), GNCG with the forward difference (GNCG-F), and the primal-dual algorithm (PD) with respect to the ground truth. Although PD is as fast as GNCG-F with $\epsilon=10^{-6}$, GNCG does not achieve the accuracy that PD does (see the gap between the solid and dashed lines)

FIG. 14 shows that in terms of relative error in the y-axis, PD converged much faster than GNCG-F and GNCG-C with numerical conditioning of $10^{-8}$ (high accuracy) and as fast as GNCG-F with $10^{-6}$ which is less accurate. At 3000 iterations, the relative errors were 8.93% and 8.85% for GNCG-F ($\epsilon=10^{-6}$) and GNCG-F ($\epsilon=10^{-8}$), respectively. However, GNCG-F ($\epsilon=10^{-8}$) did not achieve the accuracy that PD does: At 3000 iterations, the relative errors were 8.62% and 8.62% for PD ($L^3$) and PD (($L^3 + L^4$)/2). As claimed, the PD algorithm also computed the most accurate solution at 1000 iterations, the relative errors were 10.92%, 10.96%, 8.96%, 9.45%, 8.67%, and 8.51% for GNCG-C ($\varepsilon=10^{-6}$), GNCG-C ($\varepsilon=10^{-8}$), GNCG-F ($\varepsilon=10^{-6}$), GNCG-F ($\varepsilon=10^{-8}$), PD ($L^3$), and PD (($L^3+L^4$)/2), respectively, where $L = \|M\nabla\|$.

The number of flops required for GNCG and PD algorithms per iteration is almost the same. Here, iteration refers to one cycle of the nested CG loop for GNCG (#operations=2 FFTs+2 iFFTs+3 dot products+2 SAXPYs+2 GAXPYs) and one cycle of the algorithm for PD (#operations=2 FFTs+2 iFFTs+4 SAXPYs+2 GAXPYs). Note that for GNCG additional operations (1 SAXPY and 1 GAXPY) are added from the outer loop once the nested CG loop is terminated. For GNCG, the maximum number of inner iterations per outer loop was 100, with actual number of inner iterations varying from outer loop to outer loop and from dataset to dataset (50~100).

The CPU running times of each algorithm per iteration were approximately 0.79 sec, 0.80 sec, 0.75 sec, 0.75 sec, 0.75 sec, and 0.75 sec for GNCG-C ($\epsilon=10^{-6}$), GNCG-C ($\epsilon=10^{-8}$), GNCG-F ($\epsilon=10^{-6}$), GNCG-F ($\epsilon=10^{-8}$), PD ($L^3$), and PD (($L^3+L^4$)/2), respectively.

Figure 15:
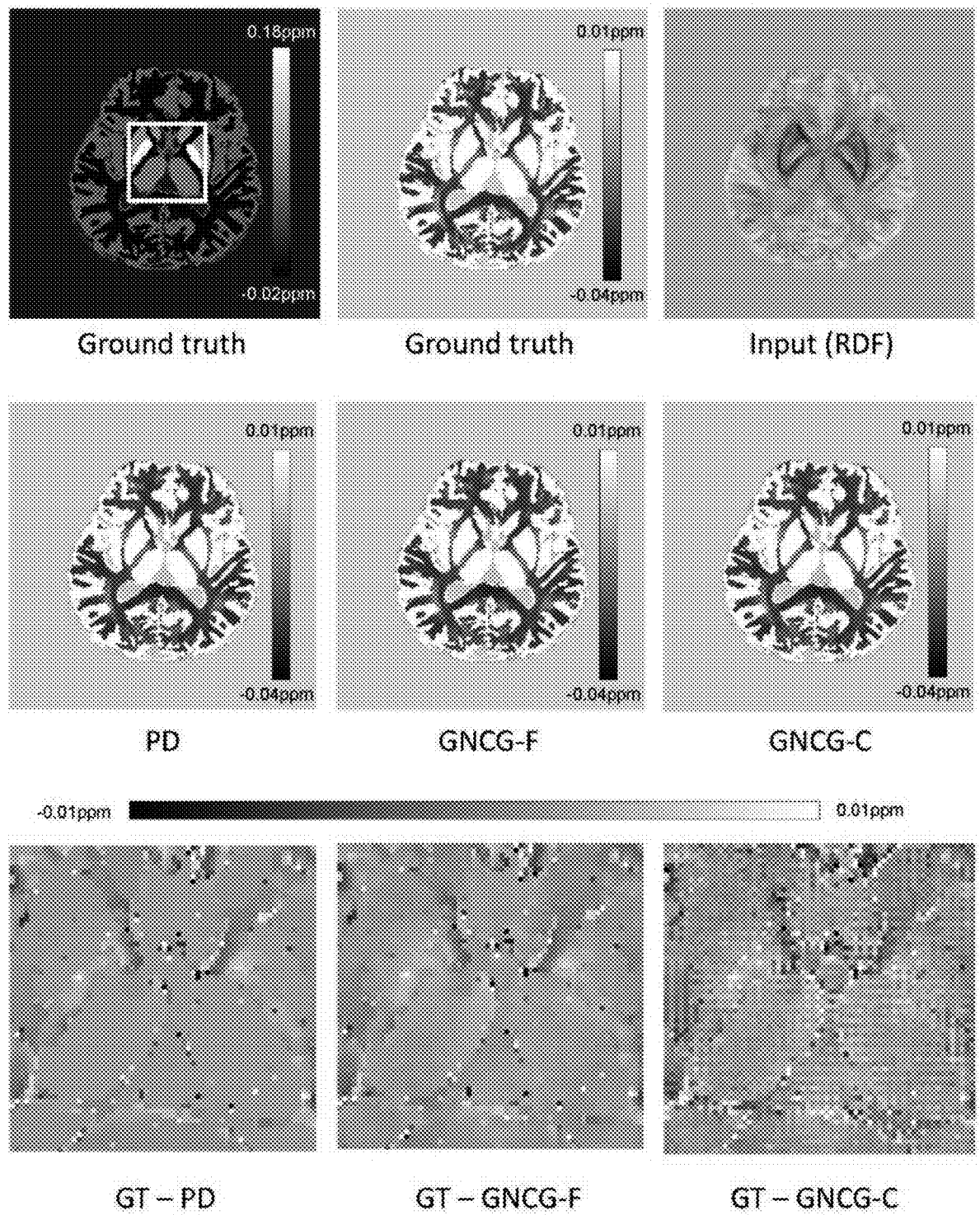
FIG. 15. Ground truth (GT) with different window levels and input relative difference field (RDF) are in the top row. GT consists of piecewise smooth regions (white matter) and piecewise constant regions (rest). Computed solutions from PD, GNCG-F, and GNCG-C are shown in the second row. Difference images between GT and computed solutions from different algorithms are displayed in the bottom row (close-up images corresponding to the bounding box in the GT image).

FIG. 15 shows that the checkerboard artifacts present in GNCG-C were removed in GNCG-F, and the error in GNCG-F was further reduced in PD Gadolinium Phantom The accuracy of GNCG-F was: for $\lambda/2=150$, linear regression slope=1.06, $R^2=0.79$; for $\lambda/2=300$, slope=1.06, $R^2=0.92$. The accuracy of PD was: for $\lambda/2=150$, slope=1.04, $R^2=0.87$; for $\lambda/2=300$, slope=1.04, $R^2=0.81$. The CPU running times (size of the Gd phantom=130×130×116) of each algorithm per iteration were approximately 0.36 sec for both GNCG-F and PD, and the GPU (GTX 750 Ti) running times of PD per iteration were approximately 0.03 sec. The total number of iterations for GNCG-F was 958 (with 10 outer iterations). The total number of iterations for PD was 800.

Ex Vivo Brain Blocks

Figure 16:
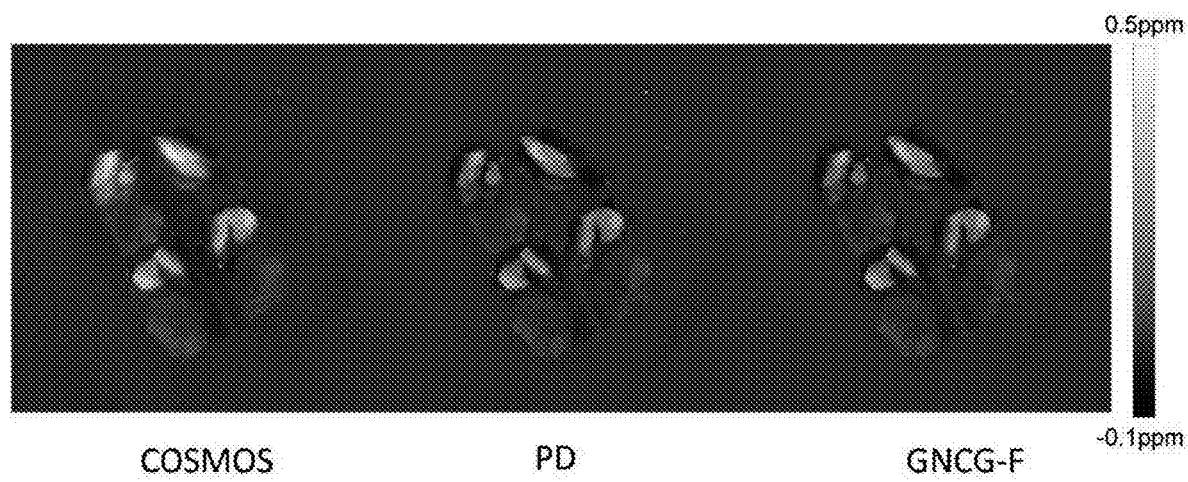
FIG. 16. Computed susceptibility map from GNCG-F and PD on ex vivo data compared to COSMOS.
Figure 17:
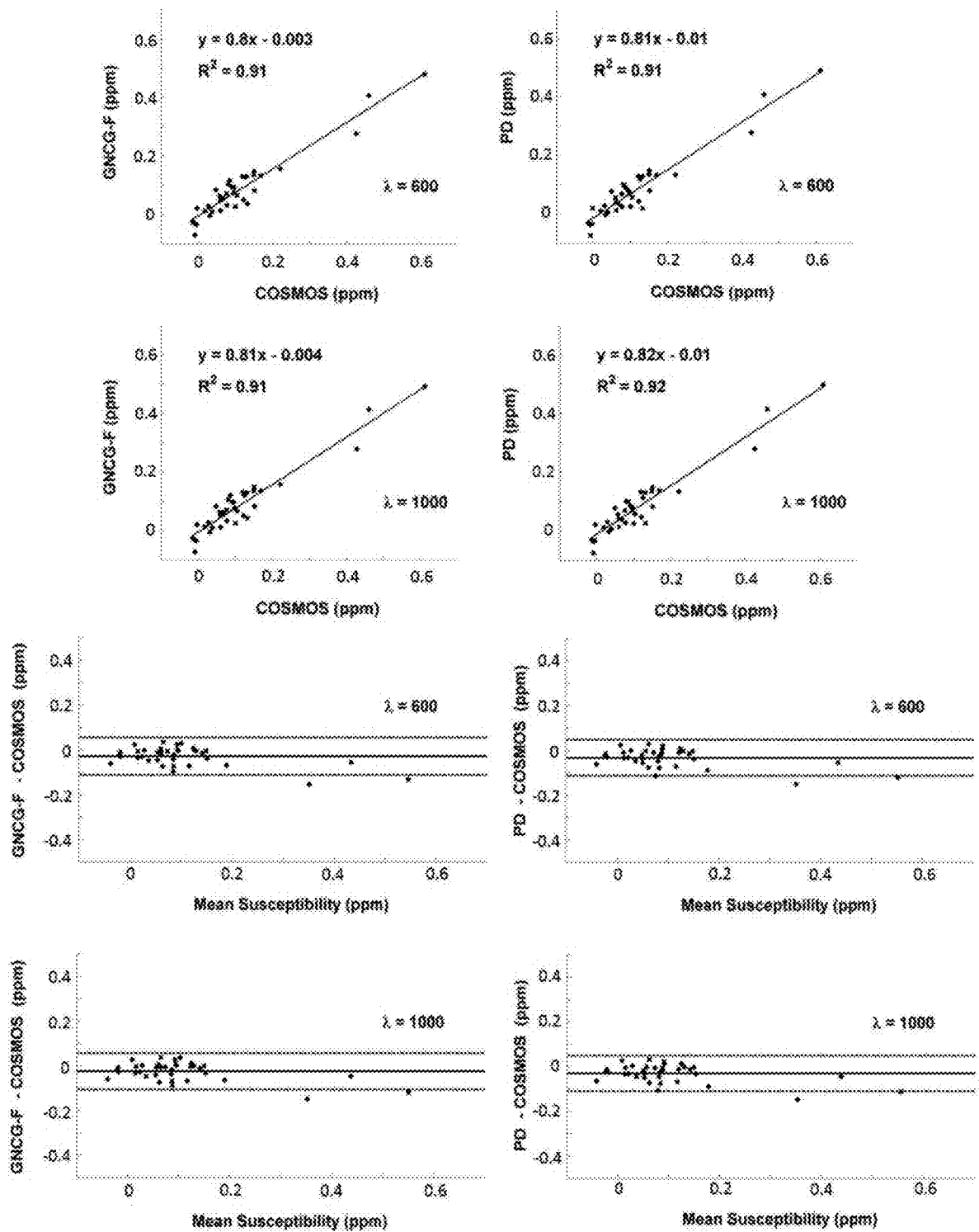
FIG. 17 Accuracy assessment via linear regression and Bland-Altman plots between different algorithms and COSMOS. The plots were generated from ex vivo brain blocks.

FIGS. 16 and 17 show the solutions obtained by the GNCG-F and PD algorithms and results of quantitative analysis for ex vivo brain tissues. For $\lambda/2=600$, the slope was 0.79 ($R^2=0.91$) and 0.81 ($R^2=0.91$) for GNCG-F and PD, respectively. For $\lambda/2=1000$, the slope was 0.81 ($R^2=0.91$) and 0.82 ($R^2=0.91$) for GNCG-F and PD, respectively. For one of the brain blocks of size 512×512×136, the CPU running times of each algorithm per iteration were approximately 4.15 sec and 4.05 sec for GNCG-F and PD, respectively. The GPU (TITAN-X) running times of PD per iteration were approximately 0.22 sec. The total number of iterations for GNCG-F was 2000 (with 20 outer iterations). The total number of iterations for PD was 2100.

In vivo Brain MRI

Figure 18:
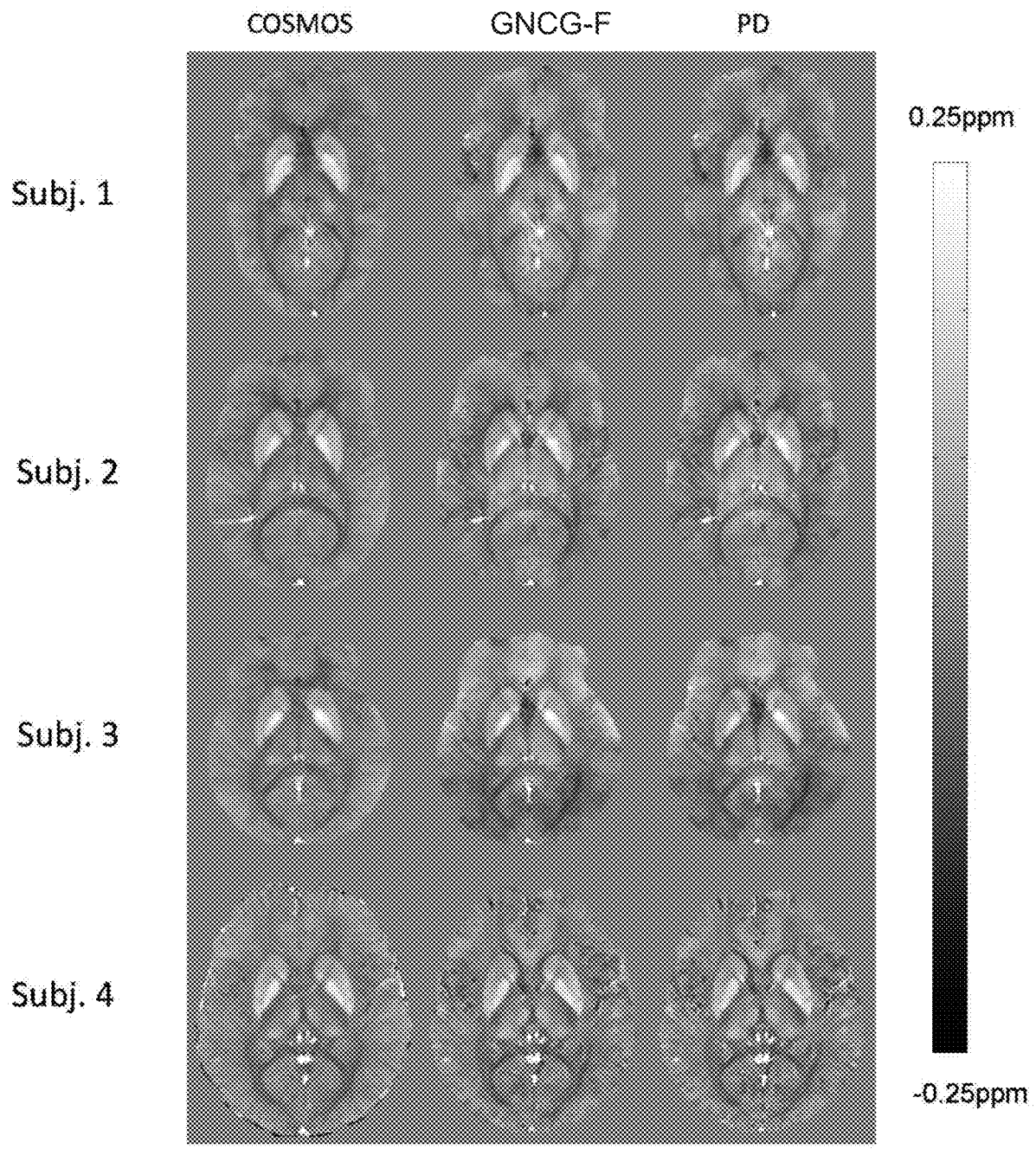
FIG. 18. Computed susceptibility map from GNCG-F and PD on in vivo brain data compared to COSMOS.
Figure 19:
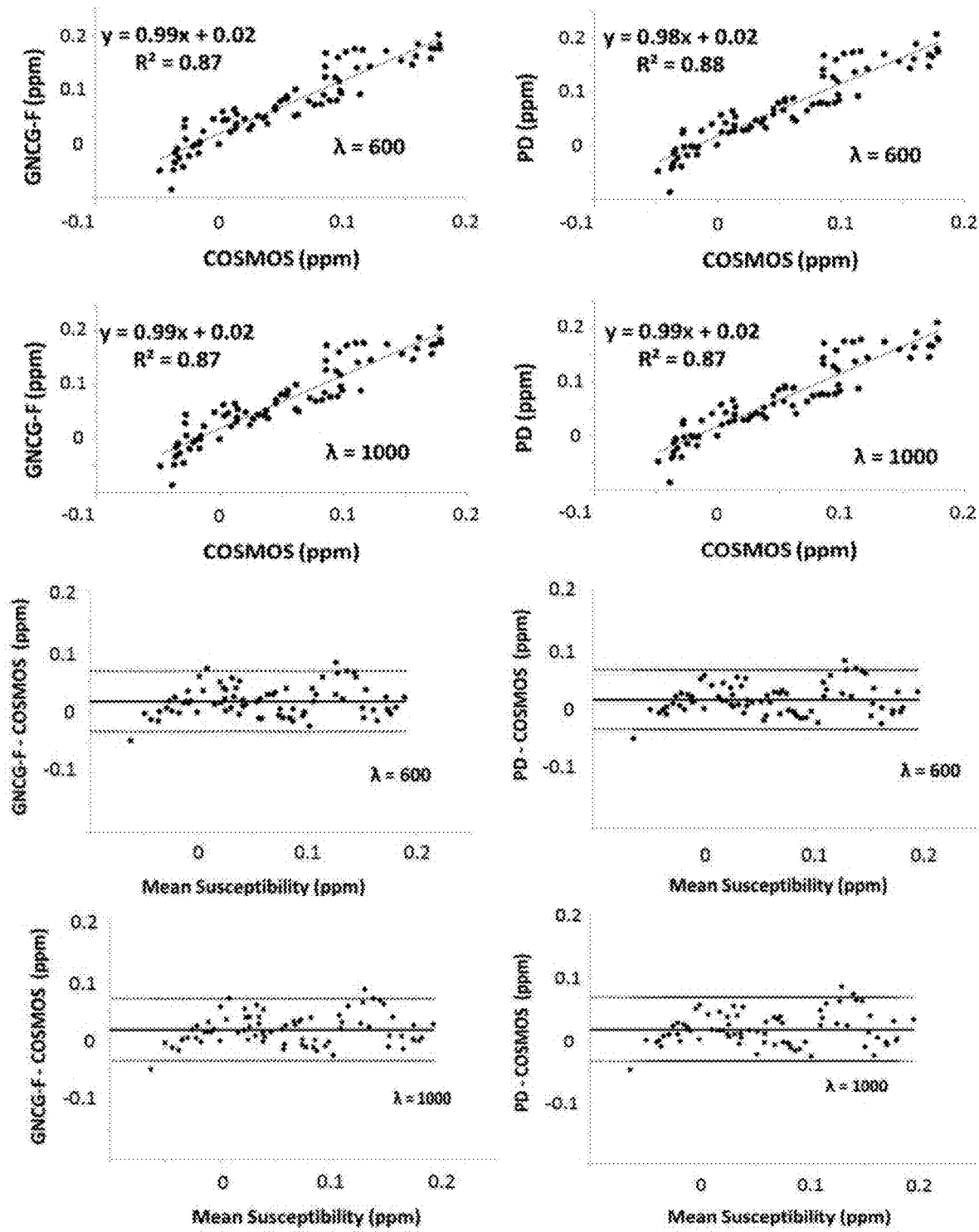
FIG. 19. Accuracy assessment via linear regression and Bland-Altman plots between different algorithms and COSMOS. The plots were generated from in vivo brain dataset.

FIGS. 18 and 19 show the solutions for GNCG-F and PD algorithms and the results of the quantitative analysis for in vivo brain MRI data. When $\lambda/2=600$, the slope was 0.99 ($R^2=0.87$) and 0.99 ($R^2=0.87$) for GNCG-F and PD, respectively. When $\lambda/2=1000$, the slope was 0.99 ($R^2$ 0.87) and 0.98 ($R^2=0.88$) for GNCG-F and PD, respectively. For the subject I in FIG. 18 of size 230×230×46, the CPU running times of each algorithm per iteration were approximately 0.29 sec for both GNCG-F and PD. The GPU (GTX 750 Ti) running times of PD per iteration were approximately 0.05 sec. The total number of iterations for GNCG-F was 1304 (with 14 outer iterations). The total number of iterations for PD was 1000.

3.5. Conclusion

In this paper, we show the influence on the convergence rate and accuracy of various implementations of the regularization term in QSM. The numerical conditioning of this term necessary for the use of the GNCG solver leads to slower convergence as compared to the continuous formulation of QSM as a saddle-point problem using the primal-dual (PD) algorithm. The use of a central difference approximation for the gradient in the regularization term can lead to checkerboard artifacts that are greatly reduced when using a forward difference approximation.

The Chambolle-Pock (primal-dual) algorithm has been applied to total generalized variation (TGV) in the context of QSM, and the split-Bregman method was alternatively used for fast QSM. Our contributions here include the following aspects: First, unlike simplified data fidelity terms (least squares) used in, we consider the MEDI problem where SNR weighting is involved (weighted least squares), which is necessary to reduce noise error in QSM but significantly increases computational cost because of the addition of two 3D Fourier transforms per CG iteration and PD iteration. Second, we employ the weighted anisotropic TV, rather than TGV, to enforce structural consistency between known tissue structure and targeted susceptibility map (morphology enable dipole inversion, MEDI). This physical MEDI has been quantitatively compared with other existing methods on clinical data to be advantageous over generic sparsity defined by unweighted TV or TGV. Third, we provide the perspective of variational methods for QSM.

Note that the QSM problem in [18] is different from the image deblurring problem considered in in the following aspects: First, as opposed to a conventional blur operator in image deblurring, the forward operator in QSM, namely the dipole kernel (with SNR weighting), does not decay to zero away from the origin in k-space but vanishes on the conic surface spanned by the magic angle ($\approx 54.7°$) from the main magnetic field. This fundamental difference in the forward operators leads to somewhat peculiar spectral properties in QSM, which was investigated in terms of the discrete Picard condition. Second, the role of TV regularization is different. Streaking artifacts can be avoided by extracting the dipole-compatible part of the field only. Although such a decomposition method is not known, the anisotropic weighted TV in [20] turns out to be able to effectively penalize streaking artifacts while preserving the underlying tissue structure. The TV regularization term in image deblurring, on the other hand, plays a role in edge-preserving smoothing while reducing additive white Gaussian noise.

Figures 20A, 20B:
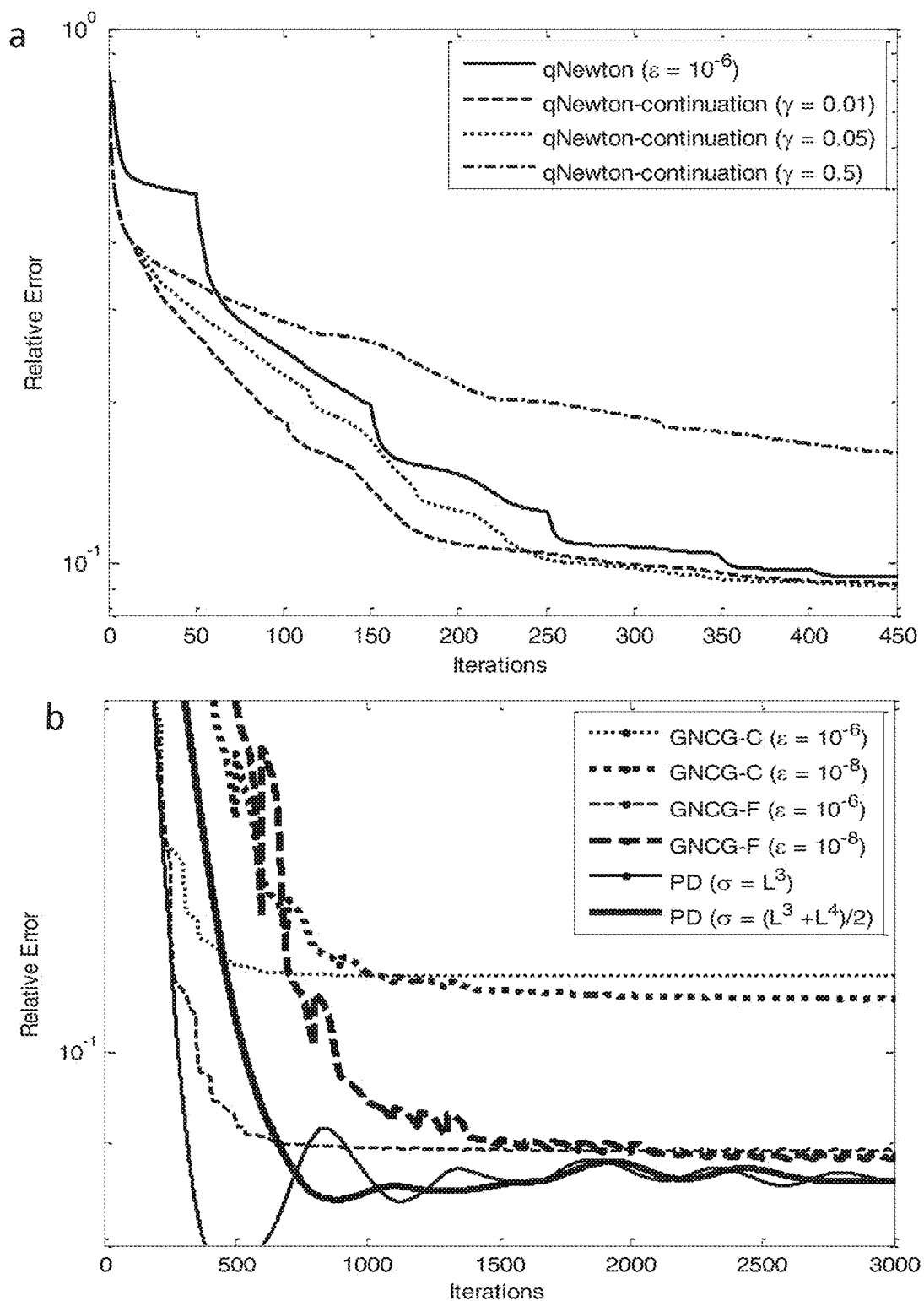
FIGS. 20a-20b. (a) The gNewton continuation method helps speed up the algorithm if the decreasing factor $\gamma$ is properly chosen. Notice that the algorithm converges rather slowly when $\gamma \geq 0.3$ as can be seen from the curves above the black one. (b) We observe that all the dashed curves eventually achieve lower relative error than the black one. The reason is that the finial value of $\epsilon$ for each continuation method (with different $\gamma$) become slightly less than $10^{-6}$ ($1.0 \times 10^{-7}$, $6.25 \times 10^{-7}$, $1.0 \times 10^{-7}$, $5.90 \times 10^{-7}$, $7.63 \times 10^{-7}$, $9.13 \times 10^{-7}$, from top to bottom in the legend). At the 3500th iteration, we computed relative error in the same order: 8.93%, 8.78%, 8.83%, 8.77%, 8.84%, 8.85%, and 8.88%. Note that these numbers are all larger than what the PD algorithm produces: 8.64% and 8.66%. Although PD exhibits fast convergence, it exhibits overshoot after 500 iterations. This behavior can be controlled by adjusting the step sizes as can be seen in FIG. 14.

Our work here illustrates the conditioning dependent convergence and accuracy in the standard GNCG, which are interior to PD (FIG. 14). The accuracy of such a sequence in GNCG can be improved by decreasing $\epsilon$ from $10_{-6}$ to $10^{-8}$, but at the cost of significantly slowing down the convergence rate of the algorithm. This is because a linear system solved by the nested CG loop becomes ill-conditioned. More precisely, the rate of convergence of the CG iteration is determined by the location of the eigenvalues (spectrum) of a linear system, and the value of the conditioning parameter $\epsilon$ affects the location of the spectrum. From a computational perspective, therefore, the algorithm would become impractical if $\epsilon$ is set to a very small number $\sim 10^{-10}$ to achieve better accuracy. This makes GNCG less preferable than PD when it comes to nonsmooth convex optimization. One way to deal with this is to make use of the so-called quasi-Newton (qNewton) continuation method. That is, at each outer iteration we reset $\epsilon$ by the rule $\epsilon = \gamma \cdot \epsilon$ where $\gamma$ is a decreasing factor. We initialize $\epsilon = 0.1$ and set $\gamma$ to values ranging from 0 to 1. FIGS. 20a-20b shows relative errors when $\gamma$ is 0.01, 0.05, 0.1, 0.3, 0.5, and 0.8.

The faster convergence of PD over GNCG (FIG. 14) may be explained by the number of floating-point operations (FLOPS) required at each iteration to achieve a given tolerance level, e.g. relative error or residual. We count the number of FLOPS required for PD and GNCG at each iteration, where $N=N_x N_y N_z$ is the total number of voxels. To elaborate, the GAXPY operation (matrix-vector multiplication) itself is in general a computational bottleneck costing $O(N^2)$, of which PD has only ¾ compared to GNCG.

However, the number of FLOPS that is actually required for the GAXPY operations used in both PD and GNCG are as few as O(N), because the matrices that are involved are very sparse. These matrices are either diagonal or gradient matrix derived from the forward/central difference scheme (except for the first and last rows each row has two nonzero components). Then, the number of FFT and inverse FFT operations dominates the execution time of GNCG and PD, which are parallelizable. Therefore, both algorithms cost O(N log N), allowing speedup using GPUs. In practice, there is much more to the cost of GNCG and PD than operations counts such as memory hierarchy and communication between data etc, Yet, with other factors that determine the accuracy of GNCG and PD (numerical conditioning and stopping rules), this computational aspect, i.e., #FLOPS, provides us the following rule of thumb: With a mild stopping criterion, the GNCG algorithm appears to be faster than PD because 1) the nested CG iteration of GNCG runs at most 100 iterations (only for the first few outer loops) and 2) the algorithm usually terminates within 10 outer iterations. However, when high accuracy is required, GNCG is not preferable compared to PD because the nested CG loop requires more iterations to attain a tighter tolerance as well as more outer iterations. Lastly, we observe that the convergence behavior of PD varies to some extent depending on the value of step size $\sigma$—accordingly $\tau=1/(\sigma\|M\nabla\|^2)$. Although the current parameter setting guarantees the global convergence of PD, there is room for speedup via adaptive scheduling for the step sizes. Note that differences in convergence rate directly translate into total computation time, since the CPU running time per iteration is nearly the same between GNCG and PD.

The suppression of checkerboard artifacts by the forward difference approximation for the gradient operation can be seen in the difference between GNCG-C and GNCG-F in FIG. 15. This may be understood intuitively as follows: Consider a 2D checkerboard pattern (binary matrix) of size 5×5 where $u_{1,1}=1$, $u_{1,2}=0$, $u_{1,3}=1$, $u_{1,4}=0$, $u_{1,5}=1$, $u_{2,1}=0$, $u_{2,2}=1$, $u_{2,3}=0$, $u_{2,4}=1$, $u_{2,5}=0$, $u_{3,1}=1$, $u_{3,2}=0$, $u_{3,3}=1$, $u_{3,4}=0$, $u_{3,5}=1$, $u_{4,1}=0$, $u_{4,2}=1$, $u_{4,3}=0$, $u_{4,4}=1$, $u_{4,5}=0$, $u_{5,1}=1$, $u_{5,2}=0$, $u_{5,3}=1$, $u_{5,4}=0$, $u_{5,5}=1$. Setting $h_x=h_y=1$, we compute the anisotropic TV of this matrix using the central difference approximation defined by $$J_c(u) := \sum_{2\le i,j\le 4} |(u_{i+1,j}-u_{i-1,j})/2| + |(u_{i,j+1}-u_{i,j-1})/2|,$$

and the forward difference approximation defined by $$J_f(u) := \sum_{2\le i,j\le 4} |u_{i,j}-u_{i-1,j}| + |u_{i,j}-u_{i,j-1}|.$$

For the nested 3×3 square of the matrix, we have $J_c=0$ and $J_f=12$. Indeed, there is no penalization by the central difference scheme, whereas there clearly exist constant fluctuations in u along the both x and y axes, which are captured by the forward difference scheme.

The error in GNCG may be understood by Huber norm analysis. Under the Sobolev assumption, the notion of numerical conditioning in the Euler-Lagrange equation of MEDI has a close relationship with the Huber-norm defined by $$|MDu|_\alpha = \begin{cases} \dfrac{|MDu|_2^2}{2\alpha} & \text{if } |MDu|_1 \le \alpha, \\ |MDu|_1 - \dfrac{\alpha}{2} & \text{if } |MDu|_1 > \alpha; \end{cases}$$

where $\alpha>0$ is a parameter that determines a trade-off between quadratic regularization for small ranges of a and anisotropic TV regularization for larger ranges of $\alpha$. Replacing the integrand in the regularization term in [18] with the Huber-norm, we can derive its Euler-Lagrange equation when $|MDu|_1 \le \alpha$ as follows:

$$\frac{1}{2\alpha}\sum_{\ell=1}^{3} \frac{\partial}{\partial r_\ell}(M^{r_\ell}(r)D^{r_\ell}u(r)) - \lambda(WT)*(W(Tu-b)) = 0, \forall r \in \text{int}\,\Omega.$$

A time-marching method can be applied to solve this equation; the overall task involves solving a diffusion equation whose diffusivity constant is given as $\frac{1}{2}\alpha$. Indeed, such diffusion processes take place in the regions where $|MDu|_1\le\alpha$. Now, consider the Euler-Lagrange equation [19] with the conditioning parameter $\epsilon$ in its denominator, i.e., $\sqrt{|M^\eta(r)D^\eta u(r)|^2+\epsilon}$ as described in the THEORY section. Applying a time-marching method to solve this equation, we notice that if $|M^\eta(r)D^\eta u(r)|\ll 1$, then $\sqrt{|M^\eta(r)D^\eta u(r)|^2+\epsilon}\approx 2\alpha$ for some $\epsilon$ and $\alpha$. Hence, the smooth regions shown in FIG. 15 GT—GNCG-F (difference image between ground truth and GNCG-F) are likely the result of the diffusion processes that originated from the Huber-norm. Since a dual formulation of the Huber-norm allows us to derive a closed-from expression of its proximal operator, the PD algorithm can be straightforwardly applied.

QSM accuracy may be further improved by recent technical advances in nonsmooth convex optimization. Energy minimization methods based on sparsity-inducing norms such as TV-seminorm have been a viable solution in a broad range of ill-posed imaging problems. It is, however, preferable to work with an energy function that faithfully captures the underlying physical nature of the imaging data. Otherwise, computing an optimal solution for a modified energy function may lead to an undesirable solution, as seen, for example, in the role of proper noise modeling for the data fidelity or prior term. The discrepancies between MEDI and COSMOS observed in ex vivo and in vivo data analyses may also be explained by model error in ignoring white matter susceptibility anisotropy and by mis-registration error.

In summary, we have shown the influence of specific implementation of the regularization term in QSM as it relates to convergence rate and accuracy. The slower convergence rate and accuracy associated with the numerical conditioning required for standard GNCG is substantially improved using a primal-dual algorithm that no longer requires the modification of the energy function in QSM. In addition, we have shown that the forward difference scheme for implementing the gradient operator suppresses the checkerboard artifacts caused by the central difference scheme. Over various types of data from phantom to in vivo human brain, the primal-dual formulation with forward gradient has shown improved convergence and accuracy over the current GNCG.

4. Shadow Artifacts Reduction: Zero Reference for QSM and Measurements of MS Lesion Susceptibility In this section, we describe a QSM improvement that provides a uniform cerebrospinal fluid (CSF) in ventricles for automatic zero reference, as well as general shadow artifacts reduction.

4.1. Introduction

Current quantitative susceptibility mapping (QSM) methods quantify magnetic susceptibility with respect to a certain level, known as the zero susceptibility reference. For brain parenchymal QSM, CSF is widely used as the zero reference because of its chemical resemblance to pure water. However, in current QSM, there is often a non-uniformity in the CSF, which increases the uncertainty of the reference susceptibility. Literature suggests that CSF flow and white matter anisotropy might contribute to this variation in CSF susceptibility.

Considering that streaking artifacts belonging to the null space of the field-to-source inverse problem can be penalized using a tissue structure prior in current Bayesian QSM (morphology enabled dipole inversion, MEDI), we regard CSF susceptibility inhomogeneity also as belonging to the null space, and we propose to use a prior that enforces the susceptibility homogeneity inside the CSF. In this paper, we present preliminary data demonstrating that minimal susceptibility variation in CSF can be achieved for a consistent and automated zero reference of QSM, which is referred to as QSM0. Furthermore, QSM0 brings about additional image quality improvement.

4.2. Theory

The cost function in the optimization problem for QSM in previous literature (MEDI) consists of a data fidelity term corresponding to the Gaussian noise in the complex MRI data, and a regularization term reflecting the structure prior information regarding the magnetic susceptibility distribution, which is the sparse discrepancy between known tissue edges and edges in the susceptibility map:

$$\chi^* = \arg\min_\chi \tfrac{1}{2}\|w(e^{-ib} - e^{-i(d^*\chi)})\|_2^2 + \lambda_1 \|M_G \nabla \chi\|_1 \quad [24]$$

with $\chi$ the susceptibility map, * the convolution with the dipole kernel d, w the noise weighting, b the magnetic field experienced by tissue with Lorentz correction or the local field or simply the magnetic field, $\nabla$ the gradient operator and $M_G$ the binary edge mask derived from the magnitude image. The proposed QSM0 introduces an additional regularization term into the cost function to enforce a known uniform susceptibility in a region of interested tissue, solving the following optimization problem:

$$\chi^* = \arg\min_\chi \tfrac{1}{2}\|w(e^{-ib} - e^{-i(d^*\chi)})\|_2^2 + \lambda_1 \|M_G \nabla \chi\|_1 + \lambda_2 \|M_{CSF}(\chi - \overline{\chi_{CSF}})\|_2^2 \quad [25]$$

Here the additional term to MEDI (Eq. 24) is an L2-regularization, where CSF is the interested tissue with a known uniform susceptibility, and $M_{CSF}$ is the region of interest (ROI) of lateral ventricular CSF with a mean susceptibility $\overline{\chi_{CSF}}$. This additional term penalizes susceptibility variation within the ventricular CSF, corresponding to the assumption of approximately homogeneous CSF susceptibility. Therefore, this second regularization term in Eq.25 enforce the known uniform susceptibility value in the region of interested tissue. For imaging situations with sufficient SNR, the first term in the right side of Eqs. 24 and 25 may be approximated as $\tfrac{1}{2}\|w/(b - d^*\chi)\|_2^2$.

We propose an automated procedure to determine the lateral ventricle mask $M_{CSF}$ using the brain ROI mask M and $R_2^*$ map CSF with its chemical composition mostly made of water is known to have a characteristic feature of very low R1, R2 and R2* values. Accordingly, CSF can be segmented out from anatomic images, such as the magnitude images from gradient echo MRI used in QSM or R2* map generated these magnitude images, based on a characteristic feature of CSF on anatomic images, such as uniform low R2* value, which allows thresholding. Multiple regions are collected by applying connectivity. A specific implementation includes the following steps:

(a) Threshold $R_2^*$: $M_2^* \triangleq R_2^* < R$, while CSF presumably has a smaller $R_2^*$ than the threshold R.

(b) Define brain centroid:

$$c = \frac{1}{N}\sum_{r \subseteq M} r,$$

where N is number of voxel in M.

(c) Define central brain region: $M_c \triangleq \{r \mid \|r - c\|_2 < 3 \text{ cm}\}$.

(d) Analyze connectivity in $M_c \cap M_{R_2}^*$: divide $M_c \cap M_{R_2}^*$ into connected components $M_{ci}$ (6-neighbour) and merge the largest 3 components: $M_{cCSF} \triangleq \{M_{c1} \cup M_{c2} \cup Mc3\}$.

(e) Analyze connectivity in $M_{R_2}^*$: divide $M_{R_2}^*$ into connected components $M_i$ (6-neighbour) and merge all components overlapping with $M_{cCSF}$: $M_{CSF} \triangleq \{\cup M_i | M_i \cap M_{cCSF} \neq \emptyset\}$.

The proposed algorithm introduces two new parameters: $\lambda_2$ and R, which will be determined in a numerical simulation discussed later.

The problem (Eq. 25) is solved using Gauss Newton Conjugate Gradient. As a final step, $\overline{\chi_{CSF}}$ is subtracted from the entire map for zero reference.

4.3. Methods and Materials

Numerical Simulation

We constructed a numerical brain phantom to simulate the CSF inhomogeneity related to anisotropic susceptibilities. Matrix size was 256×256×126, and voxel size was 1×1×1.5 mm. The susceptibility tensor was originally constructed from 12-orientation human brain scans using susceptibility tensor imaging (STI). Lateral ventricles were manually drawn (Y.Y., 4 years of experience), and regarded as the region of CSF. Under the assumption that CSF is homogeneous hence not a source for susceptibility anisotropy, susceptibility was set to 0 for CSF in each element of the susceptibility tensor. Then the synthetic local tissue field was generated with $B_0 = [0, 0, 1]$ in two ways: first, tissue field $f_{aniso}$ was generated with $\chi_{13}, \chi_{23}, \chi_{33}$ using the anisotropic forward model:

$$F_{aniso}(k) = \left(\frac{1}{3} - \frac{k_z^2}{k^2}\right) X_{33}(k) - \frac{k_x k_z}{k^2} X_{13}(k) - \frac{k_y k_z}{k^2} X_{23}(k) \quad [26]$$

where F and X are the Fourier transform of $f$ and $\chi$ respectively. Second, tissue field $f_{iso}$ was generated solely with $\chi_{33}$ using the isotropic forward model, $$F_{iso}(k) = \left(\frac{1}{3} - \frac{k_z^2}{k^2}\right) X_{33}(k).$$

Finally, Gaussian noise (SNR=100) was added to both fields. MEDI and QSM0 were applied on both fields. The root mean square error (RMSE) between the reconstructed QSM and $\chi_{33}$, Err=$\|\chi - \chi_{33}\|_2$, was calculated for each method. $\lambda_1$ was determined by minimizing Err, and used for both MEDI (Eq. 24) and QSM0 (Eq. 25). $\lambda_2$ and R in QSM0 were also determined from minimizing Err.

In vivo Experiment: Multiple Sclerosis

The brains of 8 patients with Multiple Sclerosis (MS) were imaged using multi-echo GRE at 3T (GE, Milwaukee, Wis.). All studies in this work were approved by our Institutional Review Board. Imaging sequences were: T2w fast spin echo (Flip angle=90, FOV=24 cm, TE=86 ms, TR=5250 ms, slice thickness=3 mm, acquisition matrix=416×256×68) and 3D T2*w spoiled multi-echo GRE (Flip angle=20, FOV=24 cm, TE1=4.3 ms, TR=57 ms, #TE=11, ΔTE=4.8 ms, acquisition matrix=512×512×68, voxel size=0.47×0.47×2 mm$^3$, BW=±62.5 kHz, flow compensation with monopolar readout, parallel imaging factor R=2 and a total scan time of 10 min). Nonlinear field map estimation followed by graph-cut-based phase unwrapping was applied to estimate the total field, then projection onto dipole fields (PDF) was used for background field removal in order to obtain the local field. Next, MEDI and QSM0 were performed on the same local field. The standard deviation of susceptibility in ventricular CSF was measured for both methods. For lesion susceptibility measurement, one neuroradiologist (Y.Z., 4 years of experience) drew the ROIs of each lesion on the T2w images, which were already registered onto magnitude images of the T2*w scan. Reference regions for lesion susceptibility were determined by drawing an ROI in the normal appearing white matter (NAWM) on the contralateral side of the identified lesion. The difference of mean susceptibilities between the lesion and NAWM were measured and analyzed using linear correlation and Bland-Altman plots to quantify the agreement between MEDI and QSM0. Analyses were also performed on ROIs for the in vivo data included the cortex, deep gray matter structures (red nucleus, substantia nigra, caudate nucleus, putamen, globus pallidus) and white matter regions (splenium of corpus callosum, frontal white matter, occipital white matter).

For automated measurement of MS lesion susceptibility value, the bright lesion signal on T2 weighted (T2w) images can be used to segment lesion. White matter can be automatically segmented on T1 weighted images. A seed point can be placed automatically accordingly the lesion center of mass on T2w. An iterative region growing and thresholding (IRGT) algorithm can be used to segment the lesion volume, which is at the iteration step when the IRGT volume stops growing as the growth has traced the whole lesion and then starts to jump to a large value as the growth leaks to a surrounding structure.

Clinical Study

We examined MR images of MS patients from August 2011 to January 2015 with at least two successive MRI sessions that included T2-weighted (T2w), Gd-enhanced T1-weighted (T1w+Gd) and GRE imaging. QSM was constructed in an automated manner from GRE data by deconvolving phase with the dipole kernel that connects tissue susceptibility with the magnetic field estimated from MRI phase. We compared the lesions on two successive MRIs and identified patients with at least one new T2w lesion, i.e., a lesion that was not present in prior brain MRI (in a follow-up MRI that was <1 year from the baseline MRI). All the new lesions were then grouped into enhancing and non-enhancing on T1w±Gd images.

All examinations were performed on a 3.0-T MR scanner (Signa HDxt; GE Healthcare, Milwaukee, Wis.), with an eight-channel head coil. The sequences for each patient were: (a) T2w fast spin echo, (b) pre- and (c) post-gadolinium 3D inversion recovery-prepared T1w fast spoiled gradient echo, (d) three-dimensional T2*w spoiled multi-echo GRE sequence. Imaging parameters for multi-echo GRE sequence were as follows: repetition time, 57 msec; number of echoes, 11; first echo time, 4.3 msec; echo time spacing, 4.8 msec; flip angle, 20°; bandwidth, 244 kHz; field of view, 24 cm; matrix, 416×320, section thickness, 2 mm. The GRE sequence was performed before Gd injection. The total imaging time was 16 minutes 30 seconds.

QSM was constructed from GRE data using the morphology-enabled dipole inversion (MEDI). The images obtained by the other modalities were registered to QSM by using FSL software (FLIRT Linear Registration Tool, FMRIM Software Library, Oxford, England).

After localizing all new T2w lesions by comparing them with their previous MRIs, three neuroradiologists (J. C., A. G. and G. C., with 18, 9 and 8 years of experience, respectively) used the T1w–Gd images to classify those lesions as enhancing or non-enhancing. They also classified all lesions on QSM as hyperintense and isointense relative to the adjacent white matter. All differences in lesion classification were resolved by the majority.

One neuroradiologist (Y. Z., 4 years of experience) drew the areas of each localized lesion on the T2w images while blinded to the Gd enhancement classification. White matter regions without abnormal signal on T1w and T2w images were identified as normal appearing white matter (NAWM). For a zero reference, a region-of-interest (ROI) was chosen on the NAWM at the contralateral mirror site of an identified lesion with a similar shape and size on T2w images. Then, the ROIs of lesions and NAWM references were overlaid on the QSM images using a semi-automatic software to assess values of lesion susceptibility. Veins or artifacts inside the ROIs were excluded by inspection.

Using relative susceptibilities as a means for distinguishing enhancing from non-enhancing lesions, receiver operating characteristics (ROC) were assessed to determine sensitivity, specificity, and the optimal cutoff susceptibility value (in parts per billion (ppb)) Bootstrapped estimates of the AUC and 95% confidence intervals were produced to evaluate variance. The jackknife cross validation technique was used to evaluate predictive performance of the model. A generalized estimating equation (GEE) was used to predict QSM values from three lesion types: nodular, shell, and non-enhancing. This model assumes a Gaussian distribution and an exchangeable correlation structure to account for the multiple lesions per patient. The GEE analysis was also used to predict QSM values from enhancing and non-enhancing lesions, accounting for repeated measurements per patient. All statistical analyses were performed using SPSS for Windows (version 16.0; SPSS, Chicago). P<0.05 was considered statistically significant. The accuracy for identifying patients with enhancing lesions was also calculated.

4.4. Results

Numerical Simulation

Figures 21A, 21B, 21C, 21D, 21E, 21F, 21G, 21H, 21I:
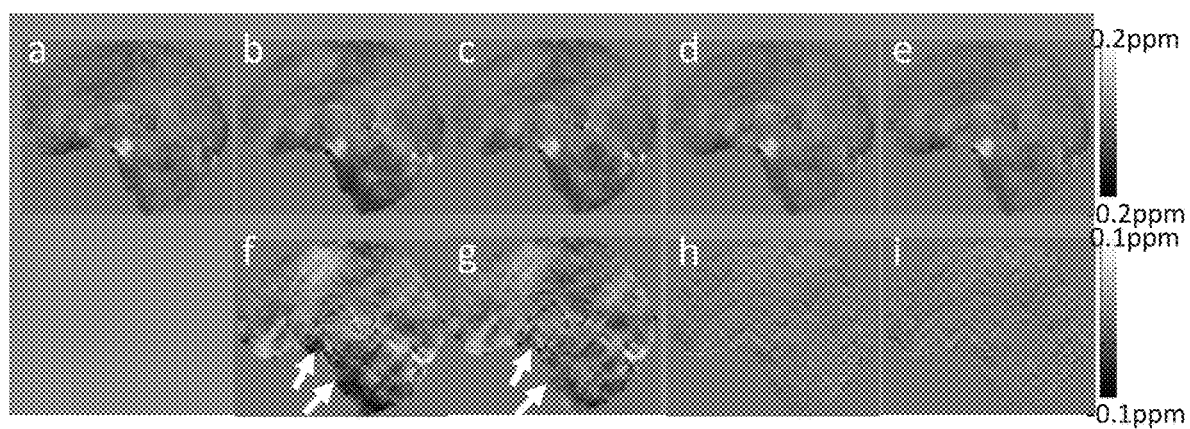
FIGS. 21a-21i. Simulation result: First row: the reference map $\chi_{33}$ (a), the QSM reconstructed using MEDI (b) and QSM0 (c) from $f_{aniso}$, and the QSM reconstructed using MEDI (d) and QSM0 (e) from $f_{iso}$. Second row: error map (f-i) between each QSM (b-e) and $\chi_{33}$. With the field generated by the anisotropic model, QSM0 reduced hypointense shadow artifacts (indicated by arrows) close to the substantia nigra and subthalamic nucleus.

FIGS. 21a-21i shows the QSM and corresponding error map with respect to $\chi_{33}$ in the numerical simulation. Given $f_{iso}$ as the input, both MEDI and QSM0 achieved relatively small RMSEs (25.4% and 25.8% respectively) as compared to $X_{33}$. When susceptibility anisotropy was simulated ($f_{aniso}$), QSM0 produced a lower RMSE (73.7%) than that of MEDI (77.3%); The RMSE within a 10 mm proximity of ventricular CSF was 65.1% for QSM0 and 74.3% for MEDI, corresponding to the reduction of the hypointense shadow artifact present near the subthalamic nucleus (FIGS. 21f and 21g). $\lambda_1$=0.001, $\mu_2$=0.1 and R=5 s$^{-1}$ were chosen. The standard deviations of susceptibility within the segmented ventricular region were 36.5 ppb for MEDI and 11.8 ppb for QSM0.

Figures 22A, 22B, 22C:
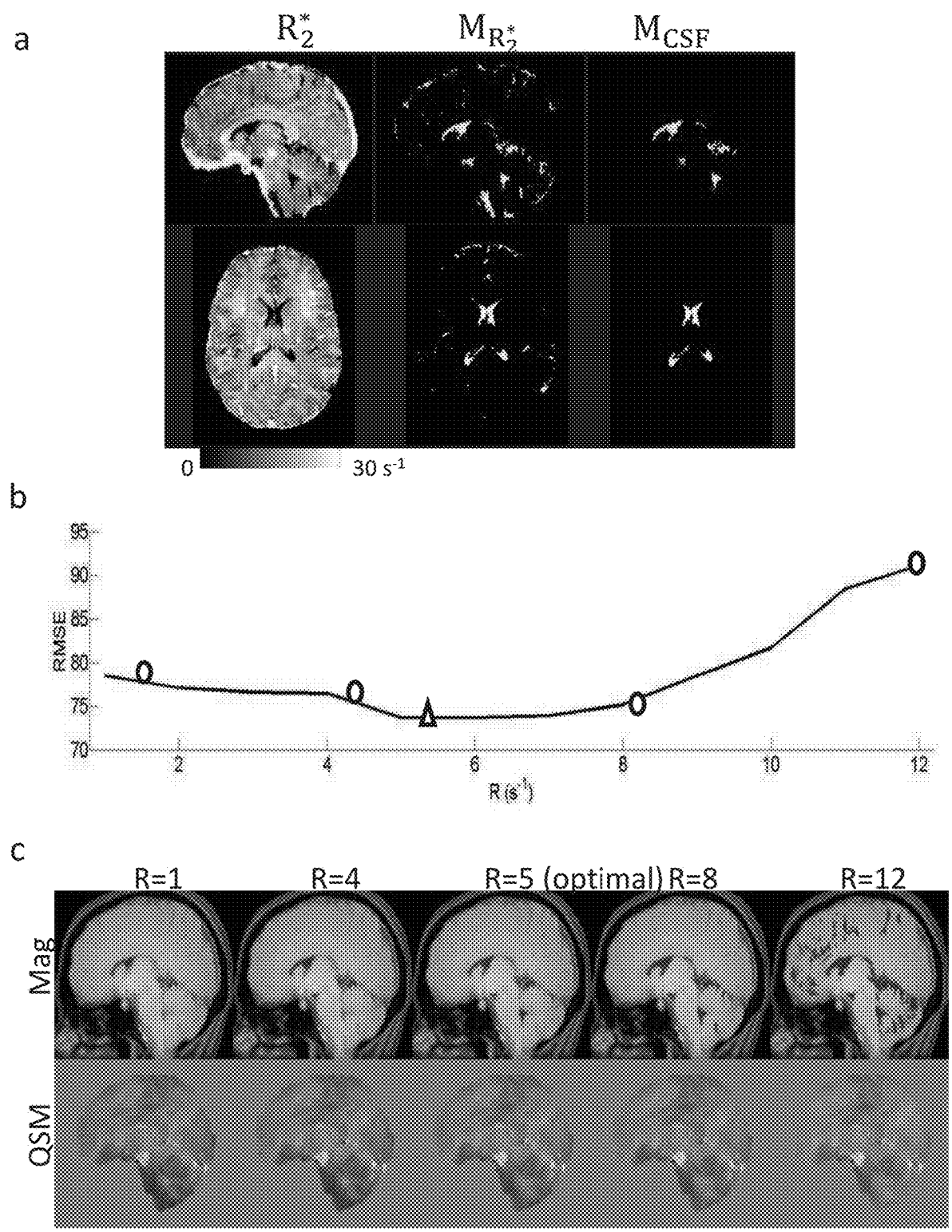
FIGS. 22a-22c. (a) Ventricle segmentation: illustration of automated ventricular CSF segmentation. A raw binary mask $M_{R_2}^*$, (second column) is generated by thresholding $R_2^*$ map (first column) and then is used to extract ventricular CSF (third column) with connectivity analysis. (b) plot of RMSE and (c) magnitude and QSM images with different threshold R. Segmented CSF ROI was overlaid with magnitude image. The RMSE was minimized with R=5.

FIG. 22a illustrates the process of the automated CSF segmentation using R=5 s$^{-1}$. FIGS. 22b and 22c show the RMSE, ROI mask and QSM with different choice of R. Optimal R was found at 5 with a minimal RMSE of 73.7%. When R was too large (R=12), structures outside ventricles were included in the segmentation, while an R too small (R=1) failed to completely depict the ventricles, especially the 4th ventricle anterior to the cerebellum. As R increased from 5 to 8, the RMSE was kept below 75% and no significant change was observed in QSM quality.

In vivo Experiment: Multiple Sclerosis

Figure 23:
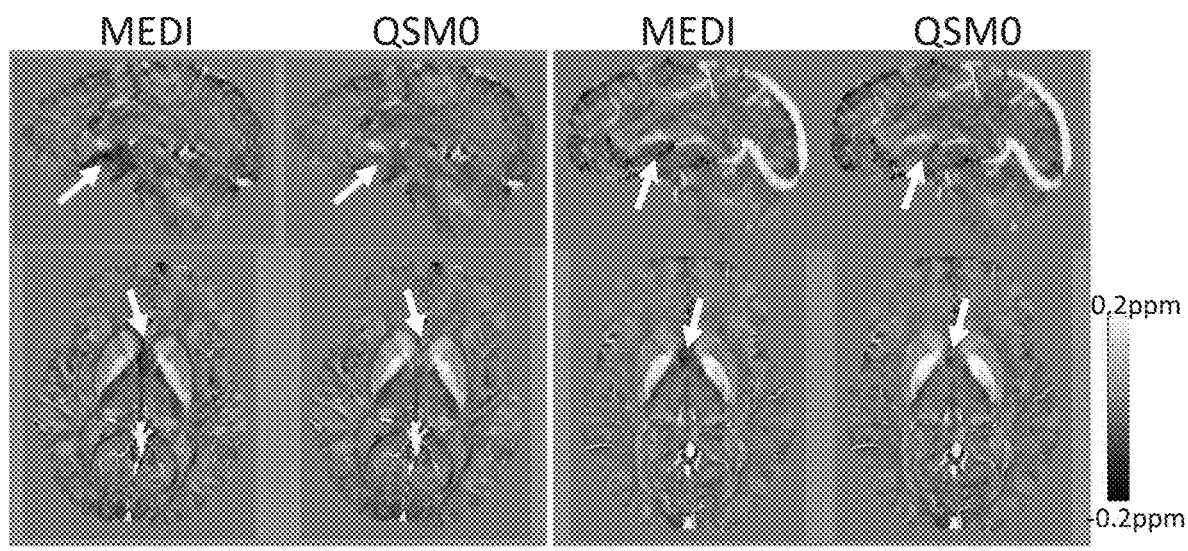
FIG. 23. In vivo brain QSM of two MS patients using MEDI and QSM0. Hypo-intensity is suppressed using QSM0 (indicated by arrows).
Figure 24:
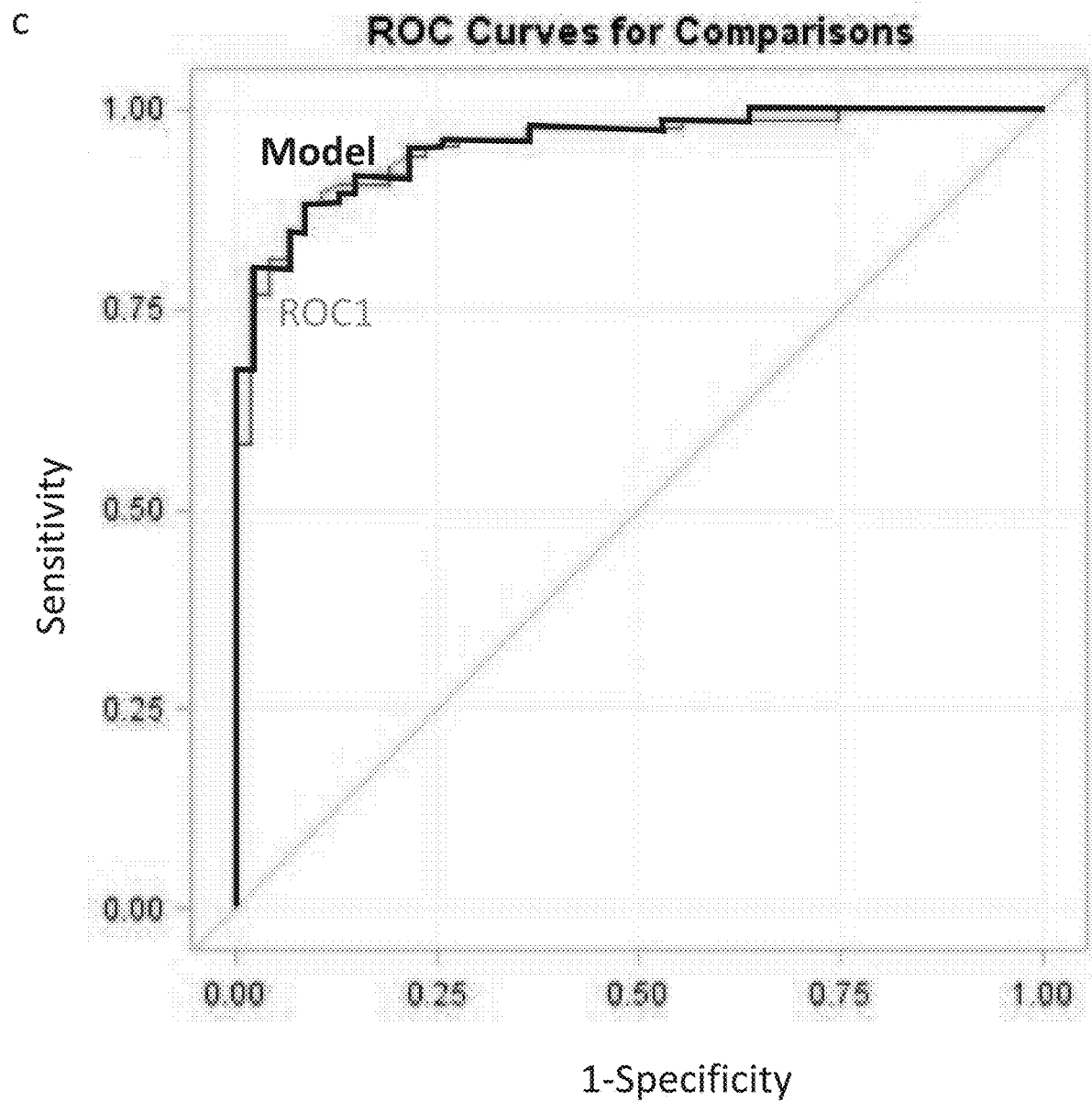
FIGS. 24a-24c. (a) Scatter (left) and Bland-Altman (right) plots of QSM measurements of all 23 lesions relative to NAWM. (b) MR images of enhancing and non-enhancing new MS lesions. A) T1w+Gd, B) T2w and C) QSM in a 44-year-old woman with relapsing-remitting MS. Two enhancing lesions (A, B, arrows) are found in T1w+Gd. One is shell enhancing (A, white arrow) and another is nodular enhancing (A, black arrow). The shell enhancing lesion appears slightly QSM hyperintense (C, white box) and the nodular one appears QSM isointense (C, black box). D) T1w+Gd, E) T2w and F) QSM in a 35-year-old woman with relapsing-remitting MS. Two new non-enhancing lesions (D, E, arrows) are found in T1w+Gd and T2w images compared to the prior MRI six months ago. Two lesions both appear QSM hyperintense with bright rims (F, arrows). (c) Receiver operator characteristic curves for susceptibility relative to NAWM to predict lesion enhancing status. AUC=0.9594 from bootstrapped Model and 0.9530 from jackknife cross validated ROC1.

FIG. 23 shows reconstructed brain QSM using MEDI and QSM0 for two MS patients $\lambda_1$=0.001, $\lambda_2$=0.1 and R=5 s$^{-1}$ were used. Hypointense shadow artifacts were suppressed at brain nuclei, indicated by arrows in FIG. 23. Standard deviation within ventricular CSF was 5-fold lower in QSM0 as compared to MEDI. In measurements of susceptibility, QSM0 showed a strong correlation with MEDI (k=1.11, R=0.93) for all 23 lesions from 8 patients (FIG. 24a). Bland-Altman analysis indicated that QSM0 has a small 1.3 ppb bias and a narrow [−8.7, 11] ppb limits of agreement with MEDI.

Clinical Study

From the eligible 482 MS patients, we identified 54 patients with at least one new T2w lesion; there was a total of 133 new T2w lesions. (One patient was excluded because of motion artifacts on GRE images.) The mean age of the 54 remaining patients (12 men and 40 women) was 34.7 years±8.1 (range 20-52 years). The disease duration for these patients ranged from 0 to 18 years (5.71 years±4.51) and the expanded disability status scale scores (EDSS) ranged from 0 to 6. Table 1 shows the demographics of these patients.

On T1w+Gd, 86 (64.7%) of the 133 lesions from 33 patients were identified as enhancing, and 47 (35.3%) non-enhancing from 25 patients, with complete agreement among the three readers. For enhancing lesions, 69 (802%) out of 86 were found to be isointense on QSM and 17 (19.8%) slightly hyperintense in contrast to adjacent white matter. According to their enhancement on T1w+Gd, the enhancing lesions were divided into 69 nodular and 17 shell. 13 of the 17 hyperintense enhancing lesions were shell enhancing. All 47 non-enhancing lesions were hyperintense on QSM but 4 (8.5%) of them were only slightly hyperintense. Example images are illustrated in FIG. 24k The lesions' mean susceptibility relative to NAWM was 20.26±7.55 ppb (mean±SD) for non-enhancing lesions and 2.49±6.39 ppb for enhancing lesions (both nodular and shell). In the GEE analysis of lesion susceptibility values between the three lesion types, both nodular enhancing (beta=−19.6, 95% CI=−23.5 to −15.8, p=<0.0001) and shell enhancing lesions (beta=−13.5, 95% CI=−19.0 to −8.0, p=<0.0001) had significantly lower susceptibility values as compared to those of non-enhancing lesions. In the GEE analysis of susceptibility values between enhancing and non-enhancing lesions, enhancing lesions had significantly lower susceptibility values as compared to those of non-enhancing lesions (beta=−17.2, 95% CI=−20.2 to −11.2, p=<0.0001). The exchangeable correlation coefficient was 0.12 for the lesion susceptibility model.

The ROC curve constructed from mean relative susceptibility values of lesions is shown in FIG. 24c. The cross-validated area under the curve (AUC) was 0.9530 (95% CI: 0.9201 to 0.9859) and the bootstrapped AUC was 0.9594 (95% CI: 0.9305-0.9884) for identifying enhancing lesions from QSM measured susceptibility values. A relative susceptibility cutoff of 11.2 ppb to distinguish enhancing from non-enhancing lesions had a sensitivity and specificity of 88.4% and 91.5%, respectively.

4.5. Conclusions

QSM0 method is proposed using automated ventricle segmentation and adding $L_2$-regularization of ventricular CSF susceptibility variation to current single orientation MEDI QSM. Our data demonstrate that the QSM0 method reduces artifacts, including CSF susceptibility inhomogeneity and hypointense shadow, which may be induced by susceptibility anisotropy in MEDI. Meanwhile, QSM0 does not affect MEDI tissue contrasts such as MS lesions relative to NAWM. Therefore, QSM0 enables a consistent CSF zero reference.

The zero reference is needed in QSM for absolute susceptibility values, because the measured tissue field is invariant with any uniform shift in the susceptibility distribution. Because CSF is chemically similar to pure water, it is a common choice for the zero reference, using a manually drawn ROI in the atrium of the lateral ventricles. However, the size of the ventricles strongly varies across subjects, and CSF often appears non-uniform in QSM. Consequently, the measured CSF value is sensitive to the ROI choice, bringing an inter-subject uncertainty in the zero reference. The described QSM0 method addresses this challenge in two aspects: First, it eliminates the need for manually choosing CSF ROI, since the ventricles are automatically segmented and used as zero reference regions; Second, it enforces CSF homogeneity during reconstruction, thereby decreasing the sensitivity to the ROI, as is evidenced by the smaller standard deviations within CSF.

The insight for the described CSF-specific regularization comes from studying the origin of the CSF susceptibility inhomogeneity in current QSM, which may be induced by the flow through lateral ventricles and anisotropy of the surrounding white matter tracts: In this work, the white matter anisotropy as the cause of CSF inhomogeneity is investigated in a numerical phantom by simulating tissue fields with and without anisotropy effects. The field from an anisotropic component ($\chi_{13}$ and $\chi_{23}$) generates spatially smooth shadow artifacts in QSM, as shown in FIGS. 21f and 21g. With the CSF homogeneity enforced in QSM0, shadow artifacts are suppressed markedly at the deep brain nuclei in simulation (FIG. 21g). This simulation agrees well with in vivo experiments (FIG. 23). In this way, the $L_2$-regularization in QSM0 reduces not only susceptibility variation within the CSF but also shadow artifacts outside the CSF.

The $L_2$-regularization of CSF susceptibility variation is conceptually similar to the use of a weighted Total Variation as a tissue structure prior that helps reduce streaking artifact. The null space of the dipole kernel allows streaking artifacts that are wave propagations associated with granular noise errors in the measured field data. The Bayesian strategy for reducing the streaking is to employ a prior term of penalizing structures (edges) that are not consistent with tissue structures in anatomic (typically magnitude) images. Similarly, the CSF susceptibility inhomogeneity and shadow artifacts may be regarded as artifacts arising from spatially smooth errors in the scalar dipole field model. A corresponding strategy to reduce these artifacts is to employ a prior term that penalizes CSF susceptibility variation, as described in this QSM0 work.

QSM0 may directly improve the delineation of deep gray nuclei, including the subthalamic nucleus, which is an important surgical target of deep brain stimulation. As QSM has already been used in many clinical applications, it is important to examine the extent to which QSM0 alters the relative contrast outside the CSF. For measuring relative susceptibility differences between MS lesions and NAWM (FIGS. 24a-24c), the strong agreement between MEDI and QSM0 suggests that QSM0 does not introduce significant changes in tissue contrast. This is desired, because the zero reference value should not change the tissue contrast. Therefore, the tissue contrasts measured on MEDI as reported in literature can be directly used with QSM0.

Our clinical data suggest that QSM and T2w together allow for accurate identification of enhancing lesions in MS patients without Gd injection within new lesions on serial MRI. This may be a potential clinical application of the reported observation that the magnetic susceptibility of an MS lesion increases rapidly as it changes from Gd enhancing to non-enhancing. One application of QSM in MS is that in serial MRI during regular monitoring of MS patients, QSM may substitute for Gd enhancement in assessing inflammatory activity. Enhancement on T1w±Gd is the current standard method to assess ongoing CNS inflammation for monitoring optimizing inflammation-suppressing treatment. Following the initial inflammatory reaction, the BBB opens and immune cells infiltrate the brain for about 3 weeks; therefore, T1w+Gd may only offer a small window into lesion pathology. During this period, the microglia/macrophages (m/M) take up and degrade myelin fragments, this is reflected in the initial lack of change in the susceptibilities of active lesions on QSM. However, after the BBB seals, immune cells remain active in the brain tissue. For example, m/M remove diamagnetic myelin fragments, and at the same time or afterwards, m/M cells with paramagnetic iron gather both at the periphery and within a lesion to further promote inflammation. For these reasons, both myelin debris removal and iron accumulation likely contribute to the increase in lesion susceptibility observed on QSM. MS lesions are hyperintense for a few years, typically with bright rims on QSM, these bright rims can be interpreted as iron. Therefore, another QSM application in MS is that, including QSM rather than Gd enhancement alone, in an MRI protocol for MS patients may provide more detailed insight into early lesion dynamics in MS.

In the proposed automated segmentation process, we selected the parameter R based on cases in the current study. For cases with different ventricle anatomy such as fetal and pediatric imaging, the parameter might be further tuned for robust segmentation of CSF. The algorithm with effectiveness in reducing "shadow artifacts" in the CSF ventricles can be extended to suppress general shadow artifacts throughout the whole brain region.

$$\chi^* = \arg\min_\chi \frac{1}{2} \|w(e^{-ib} - e^{-i(d^**\chi)})\|_2^2 + \lambda_1 \|M_G \nabla \chi\|_1 + \lambda_2 \|M_{LF}\chi\|_2^2 \quad [27]$$

Here $M_{LF}$ is an operator to extract the low spatial frequency component in the whole brain region. In one variation of implementing Eq.27, $M_{LF}$ may include a uniform mask of ventricle CSF as in Eq. 25, low frequency components of spatial variation at the half of superior-inferior or/and right-left or/and anterior-posterior size of the brain.

In summary, the proposed QSM0 method through automatic segmentation of CSF and enforcement of susceptibility homogeneity within ventricular CSF reduces QSM artifacts from susceptibility anisotropy and provides a consistent zero reference for the QSM value.

5. QSM Measurements of Liver Iron Concentration

In this section, we describe a method to measure liver iron content using QSM to compensating for R2* confounding factors including fibrosis, fat and edema.

5.1. Introduction

The liver is the only organ whose iron content is invariably increased in all types of systemic iron overload, whether from transfusion, increased dietary iron absorption, or both. Measurement of the liver storage iron concentration is the reference method for assessing the magnitude of the body iron burden in the diagnosis and management of both hereditary and acquired forms of iron overload. With iron overload, the amounts of iron in the functional and transport pools changes only slightly; almost all the excess iron is sequestered as paramagnetic ferritin and hemosiderin iron. MRI is highly sensitive to paramagnetic iron and has emerged as the primary non-invasive modality for tissue iron quantification needed in staging iron overload and monitoring iron reduction therapy. The transverse relaxation rate R2 (=1/T2), or the faster and more sensitive R2*(=1/T2*) are readily measured by commercially available MRI pulse sequences to quantify liver iron content (TIC). A major challenge in the R2 and R2* methods for mapping LIC is that they can be confounded by fat, fibrosis and other changes in cellularity that are known to contribute to R2 and R2*. These R2 and R2* confounding effects depend sensitively on the detailed microenvironment of water—confounder interaction and on the confounder spatial distribution within a voxel, which are difficult to model quantitatively. Consequently, R2 and R2* are complex functions of iron and confounders, making it difficult extract the quantity of iron from R2 and R2* measurements. It should be noted that fat suppression does not affect fat contribution to the R2 and R2* of water. In general, R2 and R2* contributions from fibrosis and other changes are difficult to quantify and compensate, While the magnitude data of the multi-echo gradient echo MRI is used to generate R2*, the phase data can be used to generate quantitative susceptibility maps (QSM to directly measure magnetic susceptibility without blooming artifacts in R2*. QSM has recently been applied to abdominal organs by additionally accounting for the fat contribution to the measured signal phase. Magnetic susceptibility is an intrinsic tissue property that is directly linearly related to liver iron. The fat contribution to tissue susceptibility can also be linearly compensated according to chemical composition. Other tissue cellularity changes including fibrosis and edema do not affect susceptibility. Accordingly, QSM is developed here to overcome R2* confounding factors in mapping LIC.

5.2. Methods and Materials

Theory

QSM algorithms to date have been designed to minimize the streaking artifacts arising from granular noisy sources using a regularization penalizing edges of streaks that are not in known tissue anatomy, which has been very successful. Following this Bayesian strategy, we propose to minimize shadow artifacts using biological prior information, a uniform region of interest on anatomic images such as T1 and T2 weighted images ($M_U$, which may be automatically identified using the characteristic feature of uniform intensity and can be detected using a regional variance calculation) should have uniform iron concentrations. For example, in thalassemia major patients, cirrhosis is typically absent and liver iron overload is evenly spread through the whole liver. Fibrosis with negligible magnetic susceptibility but with substantial T2 contributions (FIG. 27) may be evenly distributed in the liver in patients with thalassemia major. Therefore, after fat correction, we expect the susceptibilty over $M_U$ to be fairly uniform, which we can imonpose using a L2 norm. Furthermore, the aorta (region of interest $M_A$, which may be identified automatically from its characteristic feature on anatomic images, particularly bright intensity on time-of-flight MRA in which we have extensive experience) can be used as the zero reference because of its negligible susceptibility relative to water. Accordingly, we propose to use a prior that enforces the susceptibility homogeneity inside the aorta and to set the average aorta susceptibility $\langle\chi\rangle_A$ to zero. We have obtained preliminary data demonstrating that in brain QSM, minimal susceptibility variation in cerebrospinal fluid in the lateral ventricles can be achieved for a consistent and automated zero reference and for additional image quality improvement. Then hepatic QSM with zero reference and shadow-resistance against motion, flow, noise and other errors can be formulated as:

$$\chi^* = \arg\min_\chi \tfrac{1}{2}\|w(e^{-ib}-e^{-i(d^*\chi)})\|_2^2 + \lambda_1\|M_e\nabla\chi\|_1 + \lambda_2\|M_U(\chi-\chi_{fat}-\langle\chi-\chi_{fat}\rangle_U)\|_2^2 + \lambda_3\|M_A(\chi-\langle\chi\rangle_A)\|_2^2 \quad [28]$$

$M_e$ the binary edge mask derived from the magnitude image (105). The fat susceptibility $\chi X_{fat}$ can be estimated from the fat map by using $\chi_{fat}=\chi_{OA}\cdot\rho_{fat}/\rho_{OA}$ with $\rho_{fat}/\rho_{OA}$ is the fat fraction image with $\rho_{OA}$ the mean $\rho_{fat}$ value of subcutaneous fat regions that are assumed to be pure oleic acid. In the case of large SNR, $e^{-ib}-e^{-i(d^*\chi)} \approx -i(b-d^*\chi)$, linearizing the first term as fitting field data to the dipole model. Human adipose tissue is composed largely of oleic acid with a volume susceptibility $X_{OA}=0.75$ ppm. The pure fat may automatically be identified using maximal signal regions on the fat image. The fat contribution to susceptibility can be compensated according to fat fraction and pure fat volume susceptibility to generate quantitative iron map. Absolute LIC for liver iron biomaterial can then be obtained from fat-corrected susceptibility $\chi_c$ using the ferritin/hemosiderin specific mass susceptibility $X=1.6\cdot 10^{-6}$ m$^3$/Kg$_{Fe}$: LIC=$\chi_e$/X.

Once the liver iron concentration is estimated from the fat corrected QSM as described in the above, then liver iron contribution to R2* can be estimated according to calibration curves $C(\chi_c)$ for various imaging parameters and iron concentration. R2* increase from surrounding healthy liver tissue $\Delta R_2^*$ comes from iron and fibrosis. Therefore, liver fibrosis biomaterial can be quantitatively mapped from R2* with an iron correction: $\Delta R_2^*\|_{fib}=\Delta R_2^*-C(\chi_c)$.

The L2 biological constraints in Eq.28 may greatly improve QSM reconstruction SNR, as we have found in the piece-wise constant model. Accordingly, this hepatic QSM based on liver morphological priors should allow robust and accurate LIC measurement.

Phantom

To validate Gd quantification in the presence of fat, four fat-water-gadolinium (Gd) phantoms were constructed comprising of twenty-four balloons with a 28-mm diameter in varying fat/water concentrations with proton-density fat-fraction (PDFF)=0, 14.3, 28.9, and 43.7% and Gd concentration=1.25, 2.5, 5.0, 7.5, and 10.0 mmol/L, Each fat-water-Gd solution included mayonnaise (Olinesa Ltd., Bulgaria) and Gd solutions (Shanghai Xudong Haipu Pharmaceutical Co., Ltd, China). Gd solutions with Gd concentrations of 1.25, 2.5, 5.0, 7.5, and 10.0 mmol/L are corresponding to susceptibilities of 0.41, 0.81, 1.63, 2.45, and 3.26 ppm at room temperature, assuming a molar susceptibility of 326 ppm L/mol at 293 K. The balloons were embedded in a plastic cuboid container filled with water.

Subjects

Nine controls with no known hepatic disease, nine patients with known or suspected hepatic iron overload, and nine patients with focal liver lesions participated in this IRB approved HIPAA compliant study. All participants provided written informed consent. Subjects with iron overload had either hereditary hemochromatosis, transfusional hemosiderosis, leukemia, or a myelodysplastic syndrome.

MR Imaging

The fat-water-Gd phantoms were studied using a clinical 3.0T MR imaging system (MAGNETOM Trio Tim; Siemens Healthcare, Erlangen, Germany) with a combination of head and neck coils. QSM images and R2* mapping of the phantom were obtained from the same 3D unipolar readout multi-echo gradient-echo sequence with the following parameters: TR=13.1 ms, TE$_1$=1.24 ms, ATE=2.08 ms, Number of echoes=6, receiver bandwidth (RBW)=1028 Hz/pixel, FA=3°, Matrix=256×208×48, spatial resolution 1.5 mm×1.5 mm×2.0 mm.

The subjects with no known hepatic disease, and those with known or suspected hepatic iron overload were studied using a clinical 1.5 T MR imaging system (MAGNETOM Aera; Siemens Healthcare, Erlangen, Germany) with a combination of spine and torso coils. QSM images and R2* mapping of the liver were obtained from the same three dimensional (3D) bipolar readout multi-echo gradient-echo sequence with the following parameters: TR=10.0 ms, TE$_1$=1.44 ms, ATE=1.36 ms, Number of echoes=6, RBW=1065 Hz/pixel, FA=6°, Matrix=224×168×44, spatial resolution–1.7 mm×1.7 mm×5.0 mm. Additionally, a generalized auto-calibrating partially parallel acquisition with acceleration factor of 2 in the anterior-posterior direction and elliptical sampling were used to reduce acquisition time. The scan required 14 seconds that was readily completed during a single breath hold.

The subjects with focal lesions were imaged using a clinical 3.0 T MR imaging system (MAGNETOM Verio; Siemens Healthcare, Erlangen, Germany). QSM images and R2* mapping of the liver were obtained from the same 3D unipolar readout multi-echo gradient-echo sequence with the following parameters: TR=14.0 ms, TE$_1$=1.49 ms, ATE=2.06 ms, Number of echoes=6, RBW=1502 Hz/pixel, FA=10°, Matrix=256×176×26, spatial resolution=1.5 mm×1.5 mm×5.0 mm. The scans required 20 seconds and were completed during a single breath hold.

QSM and R2* Reconstruction

Phase images were extracted from the complex MRI data. Phase discrepancies between odd and even echoes in the bipolar readout gradients caused by non-ideal gradient behaviors were first measured, modeled as polynomials in space, and corrected in field mapping. Then the corrected complex MRI signal $s(\vec{r}, t)$ was modeled according to tissue chemical composition of water and fat: water signal $\rho_w(\vec{r})e^{-R^*_{2w}t}$ with water fraction $\rho_w$ in a voxel and fat signal $\rho_f(\vec{r})e^{-R^*_{2f}t}\Sigma_n\alpha_n^f e^{-i2\pi f_n^f t}$ with fat fraction $\rho_f$ in the voxel, in addition to the phase factor $e^{-i2\pi b(\vec{r})t}$ corresponding to the magnetic field generated by susceptibility. Therefore, $s(\vec{r}, t)=(\rho_w(\vec{r})e^{-R^*_{2w}t}+\rho_f(\vec{r})e^{-R^*_{2f}t}\Sigma_n\alpha_n^f e^{-i2\pi f_n^f t})\cdot e^{-i2\pi b(\vec{r})t}$.

Simultaneous phase unwrapping and chemical shift determination using graph cuts with conditional jump moves was then performed on the phase images to generate an estimate for fat and water fractions and the magnetic field, which were used as initialization for iterative computation in water-fat signal modeling to fine-tune the field map. The output field was then processed with background field removal using the projection-onto-dipole-field method, and the remaining susceptibility field was processed to generate QSM using the morphology enabled dipole inversion algorithm. The output field was also processed using the preconditioned total field inversion without background field removal.

For an effective R2* mapping of the liver, a Levenberg-Marquardt non-linear fitting was used to fit the magnitude component of the multi-echo data with multipeak fat.

Data Analysis

Liver magnetic susceptibility was measured on QSM using region of interest (ROI) analysis. The latissimus dorsi muscle was the reference for zero susceptibility. ROIs of approximately 12 cm$^2$ were placed on the liver region away from major vessels. ROIs of approximately 4 cm$^2$ were placed on the nearby latissimus dorsi muscle. ROIs for focal lesions were placed in the lesions, with an area corresponding to just below lesion size.

The fat contribution to liver susceptibility was estimated and removed from the measured liver susceptibility in the following manner to generate fat corrected QSM. Intensity inhomogeneity due to receiver coils was first estimated using a level set method and was then used to correct the fat image.

Statistical analyses were carried out using SPSS for Windows version 17.0. Linear regression analysis was performed to correlate liver magnetic susceptibility with liver R2*.

5.3. Results

FIGS. 25k-25l shows the measured susceptibility and R2* maps from fat-water-Gd phantoms. Susceptibility measured in the Gd-doped solutions was proportional to Gd concentration, with Gd molar susceptibility given by the linear regression slope (321, 318, 294, and 227 ppm for PDFF=0, 14.3, 28.9, and 43.7%, respectively) (FIGS. 25i & 25k) and the fat contribution to solution susceptibility given by measured value at vials of zero Gd on FIG. 25i. The fat contribution to solution total susceptibility was linearly proportional to the fat concentration for Gd concentrations up to 2.5 mmol/L (FIG. 25i). R2* values had complex relationships with Gd concentration that depended on fat contents: linear at PDFF=0, quadratic at PDFF=14.3%, and very nonlinear at higher PDFFs (FIG. 25l)

Water/fat separation was successful in all 9 controls and 17 of 18 patients. It failed in one patient with extremely high hepatic iron overload. The GRE images from this patient had a detectable liver signal only in the first echo and were therefore excluded from further analysis. Focal lesions in patients consisted of three hemangiomas, one hepatocellular carcinoma (HCC), three suspected cholangiocarcinomas or metastases, one with multiple malignant tumors, and one with multiple liver metastases after interventional therapy. The focal lesions had substantial effects on R2* but minimal effects on fat-corrected QSM. Examples are detailed in: FIGS. 26a-28f.

Figures 26A, 26B, 26C, 26D, 26E, 26F:
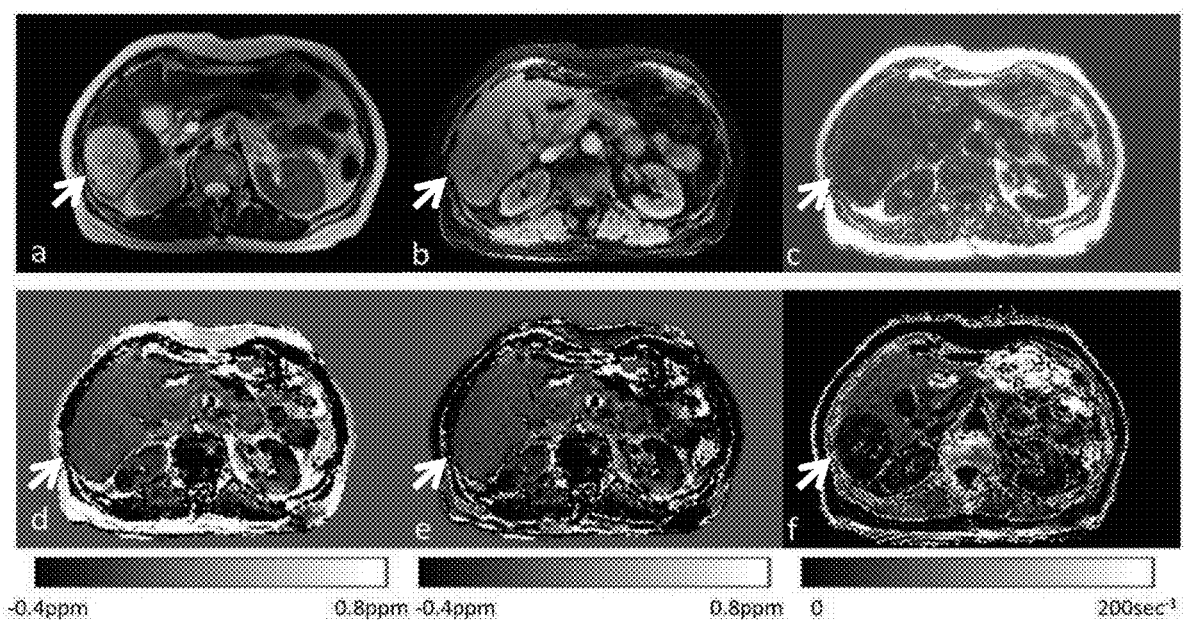
FIGS. 26a-26f. T2 weighted image (a), water map (b), fat map (c), susceptibility map without fat correction(d), susceptibility map with fat correction (e) and R2* maps (f) from a patient with hepatic hemangioma. The lesion (arrows) showed a reduced fat content (c), which substantially decreased R2* (f) but the effects were well compensated on QSM (d vs e)

FIGS. 26a-26f shows the T2 weighted image, water map, fat map, QSM susceptibility map without fat correction, susceptibility map with fat correction, and R2* map from a patient with hepatic hemangioma. The lesion showed hyperintensity in T2 weighted images (FIG. 26a) and there was a reduction on R2* (FIG. 26f). The mean R2* was 13 sec$^{-1}$ in the lesion and 42 sec$^{-1}$ in the nearby normal appearing liver tissue, and the sharp contrast between lesion to adjacent normal appealing tissue on the R2* map was spatially concordant with that on the fat map (FIGS. 26c vs 26f). The mean susceptibility value before fat correction was 0.162 ppm in the lesion and 0.203 ppm in the neighboring liver (FIG. 26d). After fat correction, there was no visually detectable contrast in the mean susceptibility value (FIG. 26e).

Figures 27A, 27B, 27C, 27D, 27E, 27F:
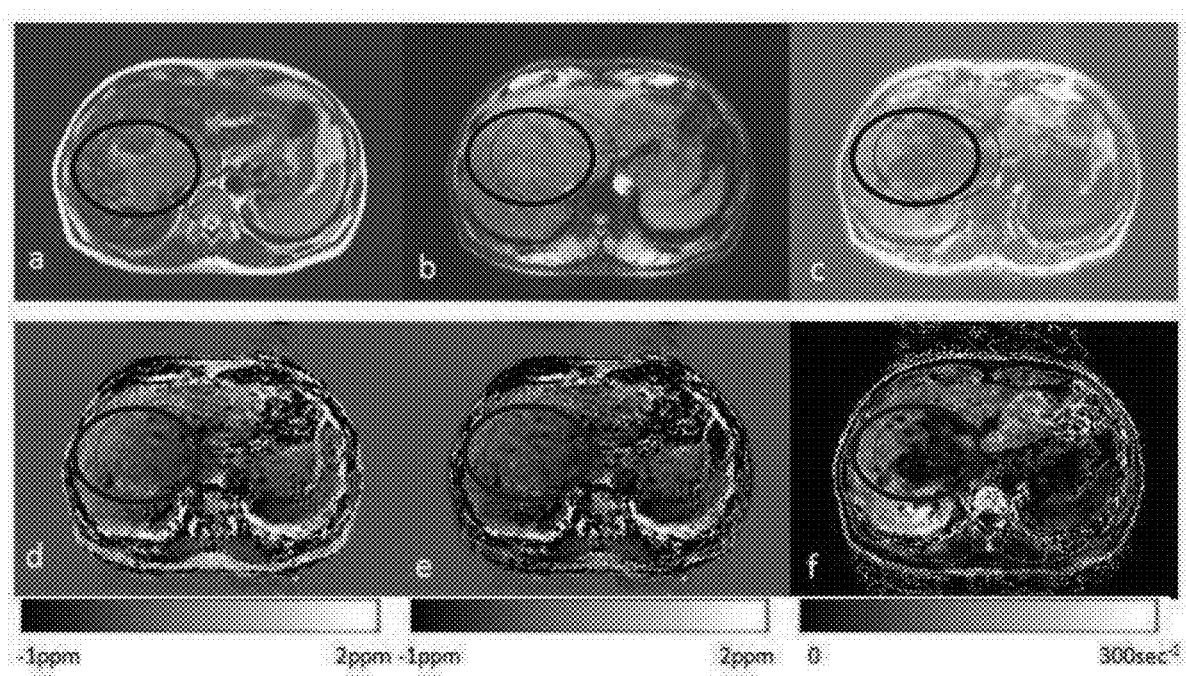
FIGS. 27a-27f. T2 weighted image (a), water map (b), fat map (c), susceptibility map without fat correction(d), susceptibility map with fat correction (e) and R2* maps (f) from a patient with suspected HCC. The substantial fat in the normal-appearing liver (c) increased R2* (f) but did not affect QSM (d vs e). The tumor (circle) had little fat (c) and consequently little R2*(l).

FIGS. 27a-27f shows the T2 weighted image, water map, fat map, susceptibility map without fat correction, susceptibility map with fat correction, and R2* map from a patient with suspected HCC. The lesion showed substantial hyperintensity on T2 weighted images (FIG. 27a) and on R2* (FIG. 27f). There was a sharp contrast between the lesion with a mean R2* of 32 sec$^{-1}$ and the adjacent normal-appearing liver tissue with a mean R2* of 121 sec$^{-1}$. The sharp contrast was spatially concordant with the sharp contrast in the fat map (FIGS. 27c vs 27f). The mean susceptibility value after fat correction was 0.081 ppm in the lesion, which gradually increased to 0.455 ppm in the neighboring normal appearing liver tissue without sharp contrast in space (FIG. 27e).

Figures 28A, 28B, 28C, 28D, 28E, 28F:
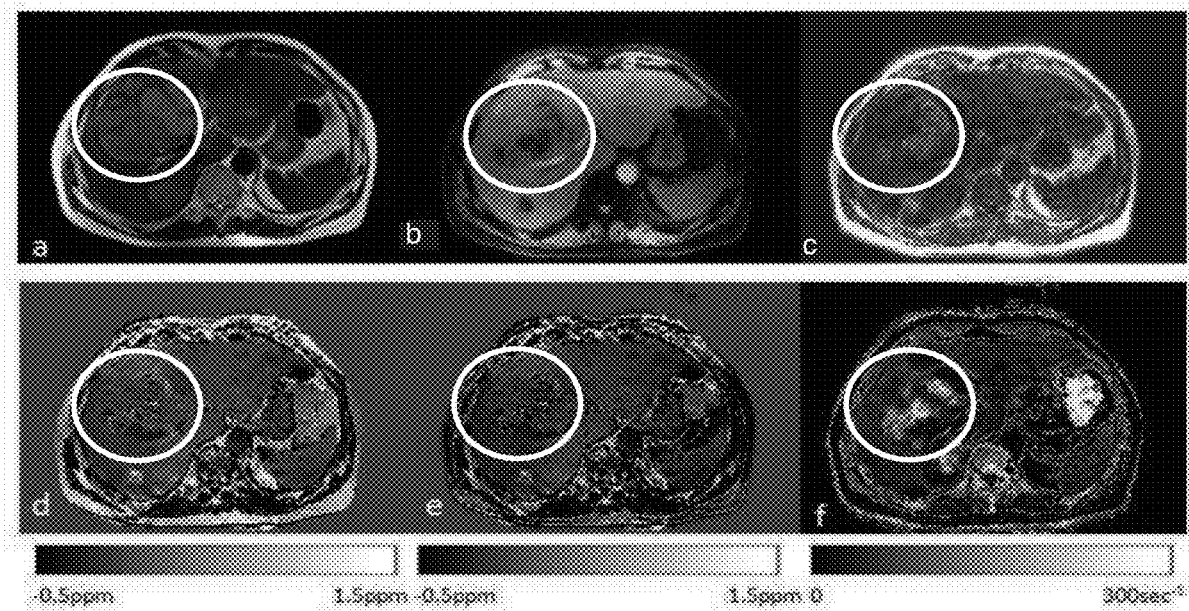
FIGS. 28a-28f. T2 weighted image (a), water map (b), fat map (c), susceptibility map without fat correction(d), susceptibility map with fat correction (e) and R2* maps (f) from a patient with multiple liver metastases after interventional therapy with transarterial chemoembolization using Lipiodol. The residual Lipiodol in metastases (circle) was seen as increased fat (c) and strongly increased R2* (f), but had little effects on QSM (d vs e).

FIGS. 28a-28f shows the T2 weighted image, water map, fat map, susceptibility map without fat correction, susceptibility map with fat correction, and R2* map from a patient with multiple liver metastases after interventional therapy with transarterial chemoembolization using Lipiodol. The metastases showed complex inhomogeneous increased and decreased signal on R2* (FIG. 28f), but only marginal change on QSM (FIGS. 28d & 28e). Residual bright spots were present on fat corrected QSM (FIG. 28e) at the treated site.

Figures 29A, 29B:
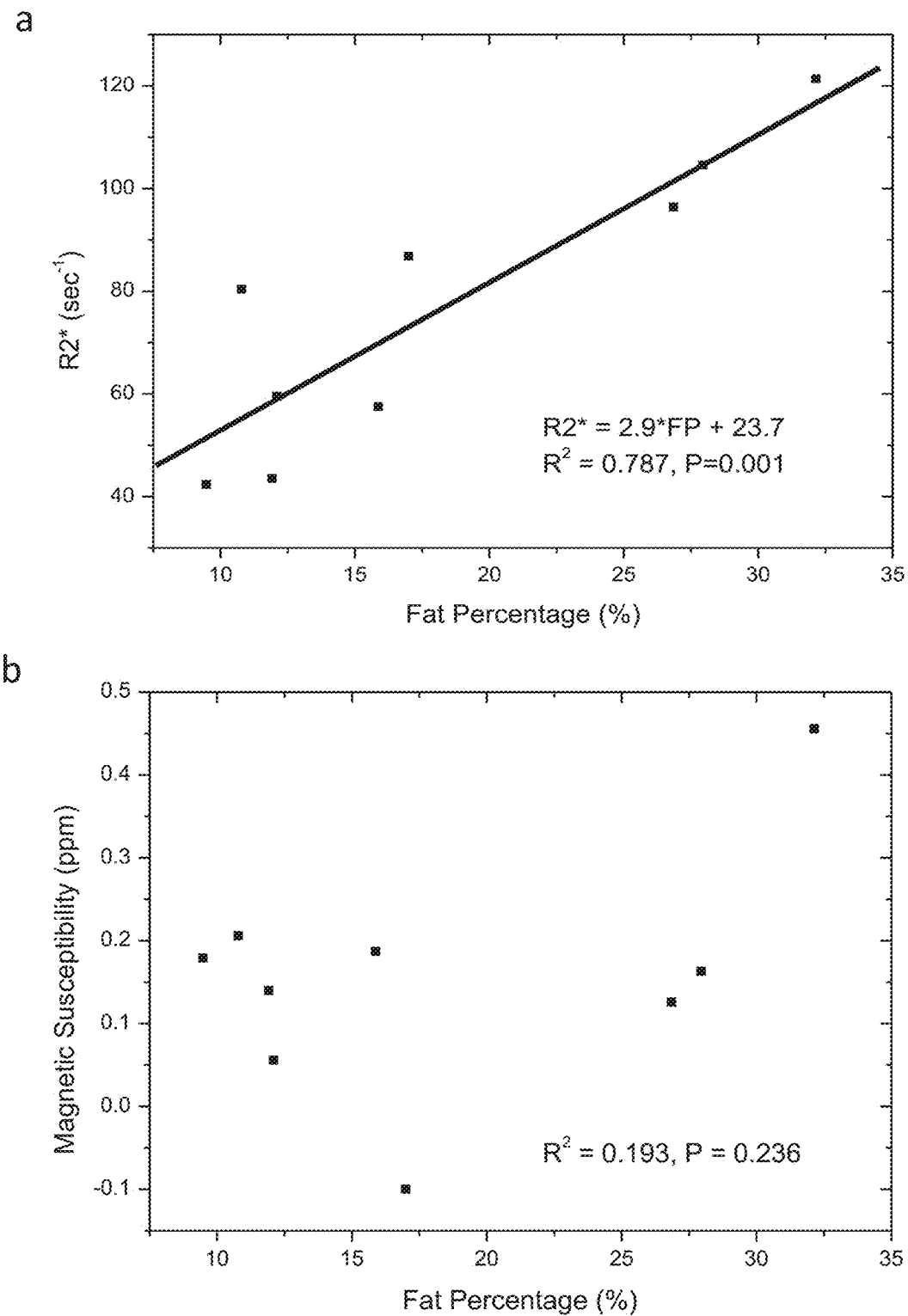
FIGS. 29a-29b. In the patients with focal liver lesions, there was (a) a linear correlation between liver fat percentages and R2* measurements, but (b) no correlation between liver magnetic susceptibility values and fat percentages.

In the patients with focal lesions, there was a correlation between liver R2* measurements and fat percentages (FIG. 29a, $R^2$=0.787, P=0,001), but no significant correlation between liver susceptibility values and fat percentages (FIG. 29b, $R^2$=0.193, P=0.236).

Figure 30:
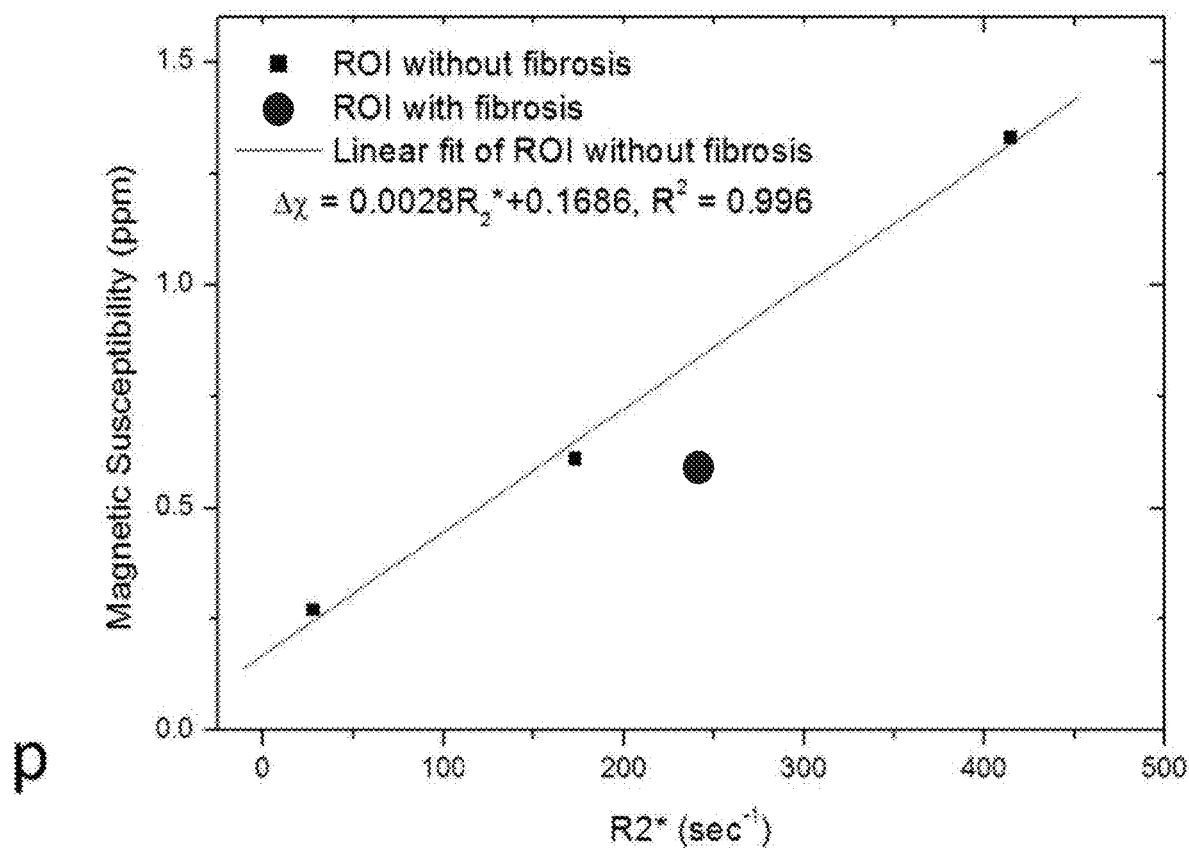
FIGS. 30a-30p. The water, fat, local field, susceptibility and R2* maps from three subjects with different levels of iron overload. For the patient with mild iron overload, there was also suspected fibrosis in the left lobe that did not affect QSM but increased R2* (arrows in the $2^{nd}$ column). Among this group of patients, there was a linear correlation (p) between liver magnetic susceptibility and $R_2^*$ in the liver regions without fibrosis (solid square), but not in liver regions with fibrosis (solid circle).

FIGS. 30a-30p shows the water, fat, local field, susceptibility, and corresponding R2* maps from three subjects with different levels of iron overload, ranging from no iron overload to moderate iron overload. As iron levels increased, both susceptibility and R2* increased. For the patient with mild iron overload, there was also suspected fibrosis in the left lobe that did not affect QSM but increased R2* (arrows in the 2$^{nd}$ column). Among this group of patients, liver magnetic susceptibility and R$_2$* were linearly correlated ($R^2$=0.996, P=0.039, FIG. 30p) in the liver regions without fibrosis, but not in the liver regions with fibrosis.

Figures 31A, 31B:
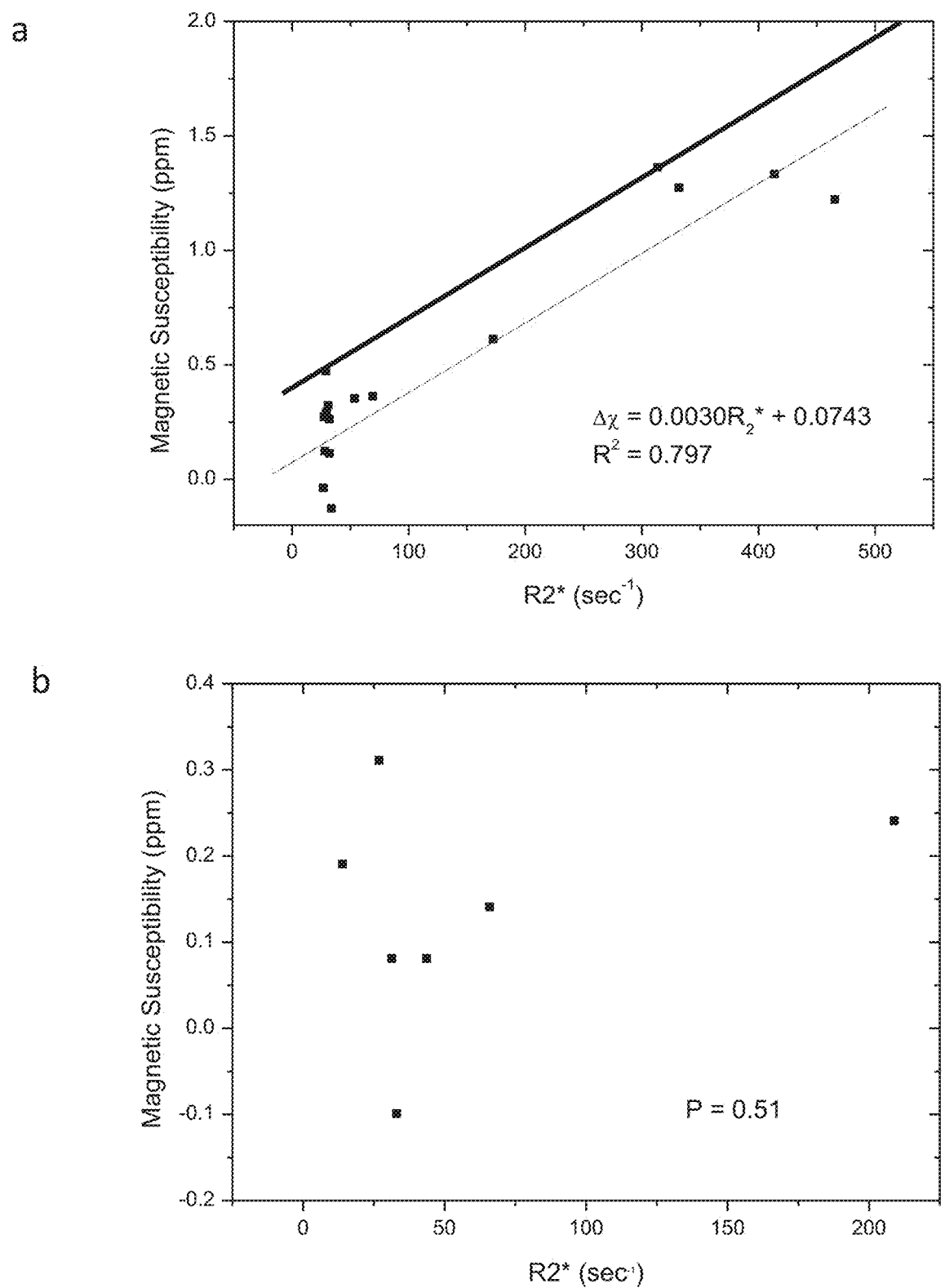
FIGS. 31a-31b. There was (a) linear correlation between liver magnetic susceptibility and $R_2^*$ in ROIs without lesions and (b) no linear correlation for ROIs within lesions.

For ROI measurements that avoided focal lesions and vascular structures, liver susceptibility and R$_2$* measurements were linearly correlated ($R^2$=0.797, P<0.0001, FIG. 31a). For measurements in ROIs on focal lesions, no significant correlation between lesional susceptibility and R2* measurements was found (P=0.51, FIG. 31b).

5.4. Conclusions

These data on liver iron mapping in 27 subjects demonstrates that the liver pathology including cysts, fibrosis, hemangioma, hepatocellular carcinoma, cholangiocarcinoma and fatty infiltration confounds R2* measurements but does not affect QSM. Lesions without fat or hemorrhage may be decreased on R2* but blend in with background liver on QSM. The fat contribution to susceptibility was corrected on QSM according to a linear tissue composition model. Our results suggest that QSM can overcome confounding factors in R2* for quantifying liver iron content (LIC).

A major challenge in current measurement of liver iron content is to correct for R2 and R2* confounding factors, including fat, fibrosis and other cellular changes that are often associated with tissue damage from iron overload. While fat fraction can be well quantified in the presence of iron using primarily the unique chemical shifts of fat, fat confounding effects on R2 and R2* depend on the detailed microenvironment of water fat interaction and the fat spatial distribution within a voxel, which are difficult to model (FIG. 25l) and compensate. Similarly, fibrosis confounding effects on R2 and R2* depend on the detailed microenvironment of water—fibrosis interaction. Fundamentally, R2 and R2* are derived from MRI signal magnitude, which depend on cellularity in complex ways that are difficult to quantify.

Fortunately, MRI signal phase allows rigorous biophysical modeling for the determination of tissue magnetic susceptibility, which is QSM. As a molecular electron cloud property linearly proportional to molecular concentration, the standard linear chemical decomposition can be applied to tissue susceptibility, enabling iron quantification with direct biophysical definition that is not possible with R2 or R2* models of iron quantity. This situation is similar to quantification of deoxygenated heme for mapping cerebral metabolic rate of oxygen consumption (CMRO2), where QSM vastly simplifies the poor traditional empirical nonlinear R2* model. Similarly, QSM enables correction for susceptibility contributions from other cellularity sources to accurately measure the amount of iron. This correction task has been made simple by the fact that fibrosis and most other confounders have virtually zero susceptibility relative to water.

Consistent with the literature, we observed decreased R2* in the presence of liver metastases, hemangioma (FIGS. 26a-26f), or malignant tumors (FIGS. 27a-27f), whereas the susceptibility values in these lesions were similar to adjacent normal liver. This can be explained by the increased water content in lesions that reduces R2* but has negligible effect on susceptibility. Liver fat increased R2* (FIGS. 27&28). The residual bright spots on fat corrected QSM at treated sites (FIGS. 28a-28f) may be explained by residual Lipiodol after interventional treatment. The case of suspected HCC (FIGS. 27a-27f) may present particularly interesting findings. The liver tissue neighboring the lesion has a mean R2* of 121 sec$^{-1}$ and susceptibility of 0.455 ppm, high values indicative of iron overload. The fat corrected QSM reveals a gradual decrease from the lesion periphery bordering normal appearing tissue to the lesion center, which may be related to hypervascularity and inflammation at the tumor margins with more necrosis in the tumor center.

Liver tissue susceptibility in this work was modeled from paramagnetic iron (gadolinium substitute in the phantom) and fat. Through signal phase analysis, the chemical shift of fat allows fat quantification through iterative water fat signal modelling and subsequent QSM. The intravoxel mixture of fat and water with different susceptibilities causes additional field inhomogeneity within a voxel and increases the apparent R2* that depends on imaging parameters including voxel size, field strength and echo time. The strong fat contribution to R2* may explain the correlation between the lesional R2* measurements and the fat percentages (FIG. 29a). As expected, lesion susceptibility values measured on fat corrected QSM were correlated with neither fat percentages (FIG. 29b) nor R2* values (FIG. 31b). Avoiding focal lesions and vascular structures, ROI measurements demonstrated a high correlation between QSM and R2* (FIGS. 30p& 31a).

The preliminary implementation can be improved with the following considerations. First, the number of patients in the preliminary study was relatively small. Patients with location lesions in this study were useful in validating QSM's effectiveness for overcoming R2* confounding factors in mapping the liver iron content. Patients with diffuse liver fibrosis caused by diffuse iron overload are of great clinical concern and should be the recruitment focus in future studies. Second, a multi-peak fat model was not considered for QSM. Multi-peak IDEAL (iterative decomposition with echo altering and least-squares-fitting) for water fat decomposition may be adopted in the last fine-tuning step in one embodiment, the iterative estimation of fat and water fractions and the magnetic field can be initialized using simultaneous phase unwrapping and chemical shift determination based on graph cuts. Another initialization approach that can be used is to include in data acquisition in-phase echoes (the Dixon method for a single-peak model) that allow estimation of R2* and magnetic field for initialization. Third, water/fat separation failed in a patient with very high hepatic iron overload and consequent extremely rapid signal decay. Ultrashort TE techniques based on radial acquisitions or offset echo GRE sequences can be used to acquire sufficient signal for data processing in patients with very rapid T2* signal decay. Fourth, there is no correlation with immunohistochemistry, which would help us interpret QSM and R2* similar to studies on white matter lesions in multiple sclerosis. Fifth, there seemed to be complications resulting in nonlinear susceptibility at high concentrations of Gd and fat in the phantom in FIG. 25i. Data at lower Gd concentrations agreed well with the linear chemical decomposition. Sixth, breath-hold acquisition is limiting for certain patients. Free-breathing method can be developed using repeated acquisition of the k-space center along the slice encoding direction to derive both respiratory and cardiac self-gating signals, which would enable a free-breathing navigator acquisition without an increase in scan time. A 3D golden ratio view order can be used to evenly distribute the acquired spiral interleaves across the k_x k_y plane, the slice-encoding plane, and across echoes. Spiral trajectories have inherent flow compensation. The redundant information in the echo dimension can be exploited using a dictionary-based reconstruction to reconstruct each echo separately.

In summary, R2* mapping of liver iron content is confounded by fat, fibrosis, edema and other cellularity pathologies. QSM overcomes confounding factors in R2* for mapping liver iron content.

6. QSM Measurements of Bone Mineralization

In this section, we describe a QSM method to measure bone mineralization by detailed biophysical modelling of fat and cortical bone signal.

6.1. Introduction

Magnetic susceptibility is a fundamental tissue property which can be observed in MRI. Densely calcified tissues such as bone have strong diamagnetic susceptibility. Quantitative susceptibility mapping (QSM) can provide quantitative, reproducible images of magnetic susceptibility sources for assessing the health and disease of most tissues but has been limited in bones. Given the importance of bone mineral density for assessing bone fracture risks in postmenopausal women and the elderly population, QSM may become a useful diagnostic tool for non-invasive imaging of bone health without the use of ionizing radiation.

QSM of the bone has been challenging because it requires complete measurements of phase everywhere within the region of interest (ROI) while cortical bone typically has very low signal at conventional echo times in gradient echo (GRE) imaging. Although water is abundant in cortical bone (~15% by volume), it mostly exists in "bound" form, connected to the crystalline mineral structures or the collagen matrix. As a result, bound bone water has an ultra-short apparent transverse relaxation time (T2* ~300 μs), resulting in no meaningful phase for QSM reconstruction on conventional MRI. Due to these limitations, previous work in muscular-skeletal applications of QSM was either focused on cartilage, or utilized piece-wise estimations of bone susceptibility. An additional problem is the intermingling of fat and water protons in the bone marrow.

In this work, we measured bone MRI signal using an ultra-short echo time (UTE) pulse sequence with FE<<1 ms. We investigated chemical shift and R2* components to properly model bone MRI signal in both UTE and conventional GRE. Finally, we present an MRI method for quantitatively mapping bone susceptibility from UTE-GRE datasets.

6.2. Theory

Magnetic field estimation is an essential initial step for QSM. For QSM of anatomical regions where magnetic susceptibility is the predominant contributor to the proton phase accrual such as in the brain, field can be estimated from the MRI signal phase. For QSM on regions with high fat content, such as bone with marrow, a complex MRI signal is modelled according to tissue chemical composition of water and fat. The inhomogeneous field generated by susceptibility is estimated through robust separation of water and fat signals.

In a multi-echo GRE sequence, the temporal behavior of the signal originating from the voxel $\vec{r}$ that contains multiple species can be expressed in general form as:

$$s(\vec{r}, t) = \sum_k \rho_k(\vec{r}) \cdot \sum_n \alpha_n^k e^{-i2\pi f_n^k t} e^{-R_{2n}^{*k} t} \cdot e^{-i2\pi b(\vec{r})t} \quad [29]$$

Here, $\rho_k$ is the complex amplitude of the signal originating from the kth chemical species within the voxel at time t=0, a is the relative amplitude of the nth peak in the chemical spectrum of the kth species, and $f_n^k$ are $R_{2n}^{*k}$ are respectively the corresponding chemical shift and R2* decay rate for the nth spectral peak of the kth species, and $b(\vec{r})$ is a spatially varying field induced by susceptibility sources experienced by protons, or the susceptibility magnetic field or the magnetic field. Extracting multiple parameters from the MRI signal is highly sensitive to noise propagation, and reducing the number of parameters in Eq.29 is a critical procedure for robust estimation. We propose the following reduction of parameter numbers:

In many clinical applications, water and fat are the dominant species and Eq.29 becomes $$s(\vec{r}, t) = \left(\rho_w(\vec{r})e^{-R_{2w}^* t} + \rho_f(\vec{r}) \sum_n \alpha_n^f e^{-i2\pi f_n^f t} e^{-R_{2n}^{*f} t}\right) \cdot e^{-i2\pi b(\vec{r})t} \quad [30]$$

Here $\alpha_n^f$ the relative amplitude of the nth spectral peak of fat, $\rho_f$ and $\rho_w$ are fat and water complex amplitude at time t=0, $R_{2w}^*$, and $R_{2n}^{*f}$ are water and the nth spectral component of fat longitudinal decay rates.

Assuming all fat spectral peaks experience similar R2* decay, can be simplified as $$s(\vec{r}, t) = \left(\rho_w(\vec{r})e^{-R_{2w}^* t} + \rho_f(\vec{r})e^{-R_{2f}^* t} \sum_n \alpha_n^f e^{-i2\pi f_n^f t}\right) \cdot e^{-i2\pi b(\vec{r})t} \quad [31]$$

Currently, the difference in water and fat R2* within a voxel $\vec{r}$ are commonly neglected:

$$s(\vec{r}, t) = \left(\rho_w(\vec{r}) + \rho_f(\vec{r}) \sum_n \alpha_n^f e^{-i2\pi f_n^f t}\right) \cdot e^{-R_2^* t} \cdot e^{-i2\pi b(\vec{r})t} \quad [32]$$

Unfortunately, for bone tissue, water is distributed through porous mineral matrix, and fat in marrow tends to aggregate together, and we have $R_{2_{bone}}^* >> R_{2_{fat}}^*$. Consequently, the use of Eq.32 to fit bone MRI signal may lead to very large errors in the estimation of fat fraction, susceptibility field, and QSM.

Therefore, we propose to avoid the R2* simplification in Eq.32. The water signal is the main component acquired in cortical bone voxels. In our experiments (see below), the largest echo time is much shorter than the $T_2^*$ of surrounding soft tissues, including marrow. Therefore, the bone water is the only species experiencing significant decay during acquisition. Accordingly, we further propose a bone-specific R2* model with the following reduction of parameters:

$$s(\vec{r}, t) = \left(\rho_w(\vec{r})e^{-R_{2w}^* t} + \rho_f(\vec{r}) \sum_n \alpha_n^f e^{-i2\pi f_n^f t}\right) \cdot e^{-i2\pi b(\vec{r})t} \quad [33]$$

6.3. Methods and Materials

Pulse sequence. A radial 3D GRE UTE sequence with TE≥40 μs was implemented on a clinical 3T scanner (GE Excite HD, Milwaukee, Wis.). The sequence used a nonselective hard pulse (rectangular pulse of 100 μs duration) to achieve volumetric excitation and two readouts per TR to accelerate acquisition (FIG. 32). On successive TRs, the echo times were shifted to achieve a total of four unique echo times, two of which are considered ultra-short.

Porcine phantom experiment. A phantom consisting of a porcine hoof (length 16 cm, thickness 6.5 cm) embedded in 1% agarose gel (container height 20 cm, average diameter 11 cm) was constructed and for the purpose of comparison was imaged using an MR scanner (3T, GE Excite HD, Milwaukee, Wis.) and a clinical CT system (LightSpeed Xtra, GE Milwaukee, Wis.). MR imaging parameters included the following: TE=0.04, 0.24, 3.0, 4.0 ms, TR=12 ms, FA=15°, FOV=18 cm, 32000 radial projections per echo, voxel size 0.7×0.7×1.4 mm, BW=±62.5 kHz., total acquisition time=13 min. CT data was acquired using the following parameters: 120 kVp, 200 mA, 0.625 mm slice thickness, 512×512 matrix, achieving nearly isotropic resolution.

Volunteer MR imaging. After obtaining written informed consent, 7 healthy volunteers (6 male, 1 female age range 25-32 years, mean=30) were scanned. All exams were performed under protocols approved by the Institutional Review Board and were HIPAA compliant. Images (11 distal femurs. 1 distal radius and 1 proximal tibia) were obtained on a 3T MRI system using an 8 channel transmit-receive knee coil and 8 channel transmit-receive wrist array. The 3D UTE GRE sequence was used with the following parameters: TE=0.04, 0.24, 3.0, 4.0 ms, TR=12 ms (pairs of the $1^{st}/3^{rd}$ and $2^{nd}/4^{th}$ echoes were acquired on successive TRs in this experiment), FA=15°, FOV=18 cm, 32000 radial projections, voxel size 0.7×0.7×1.4 mm³, Total acquisition time for all echoes 13 min.

Image processing and analysis. Each radial MR dataset was reconstructed using regridding, which interpolates the measured signal from radial spoke onto a Cartesian grid. In this work, NUFFT with Kaiser-Bessel kernel and min-max interpolation was implemented. Because of the non-uniform sampling density of our radial trajectory, density compensation was applied to the measured signal prior to re-gridding. Each data set was reconstructed on a coil-by-coil and echo-by echo basis.

For each coil, the phase of the 1st echo was subtracted from the phase of each following echo in order to remove the phase of the coil sensitivity. Then for each echo, the complex images after the phase subtraction were summed across all coils. Finally, the phase of this summed signal was used as the phase for the corresponding echo. Phase of the 1st echo became zero after this process. In mathematical form this process can be written:

$$\hat{i}_m = \hat{M}_m \exp(-i\hat{\Phi}_m)$$

where $\hat{i}_m$ is complex data corresponding to the mth echo, $\hat{M}_m = \sqrt{|\Sigma_{n=1}^{N_c} I_{1,n} I_{m,n}{}^c|}$ is the magnitude of that echo and $\hat{\Phi}_m = \angle(\Sigma_{n=1}^{N_c} I_{1,n} I_{m,n}{}^c)$ is its phase. Index n is used to denote nth coil, and $I^c$ is the conjugate of I.

Water, fat and inhomogeneity components were then obtained using IDEAL-based techniques. For this iterative method, it is important to use an initial guess for the inhomogeneity field that is reasonably close to the true solution in order to avoid convergence to a local minimal In the current work, a preliminary field map estimation was carried out using a graph cut based phase unwrapping and chemical shift estimation assuming a single chemical shift peak with value $f = -3.5$ ppm·$\gamma B_0$ Hz. An initial estimation of the distribution of R2* values was produced by mono-exponential fitting. The complex data was then fitted to $\mathrm{Ee}_j s$ [33] and [32] assuming different models for the fat chemical spectrum—single peak model ($\Delta f = 3.46$ ppm) and multi-peak model ($\overrightarrow{\Delta f} = \{-3.82, -3.46, -2.74, -1.86, -0.5, 0.5\}$ ppm). The resulting inhomogeneity field b was then passed for susceptibility mapping to the morphology enabled dipole inversion (MEDI) pipeline in which Projection onto Dipole Fields (PDF) was utilized for background field removal.

The CT images of the porcine hoof were resampled and registered to the reconstructed susceptibility map using the FLIRT algorithm in the FSL toolbox. ROI analysis was performed on co-registered volumes to correlate the CT signal (in Hounsfield units) with the MR signal (calculated susceptibility values). For this, 58 in-slice regions of interest were manually drawn in trabecular and cortical areas of metacarpal and phalanx bones, and flexor tendon. QSM (referenced to muscle tissue) and CT volumetric averages for the ROIs were recorded and used for correlation analysis.

6.4. Results

Figure 33:
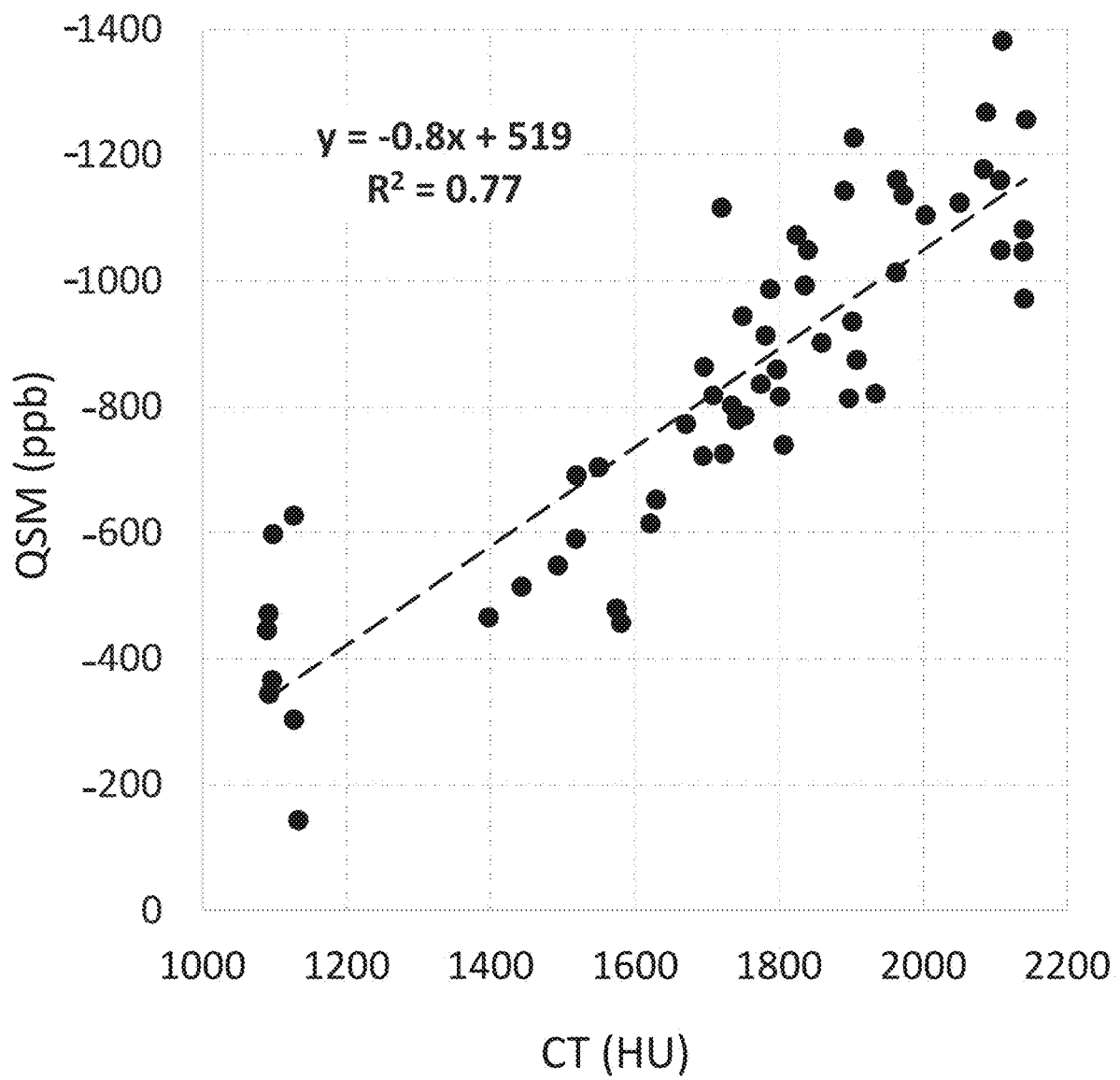
FIG. 33. Linear regression of QSM vs. CT for the ROI values in the porcine hoof phantom. Good correlation was observed between estimated susceptibility and Hounsfield units.
Figures 34A, 34B, 34C, 34D, 34E, 34F:
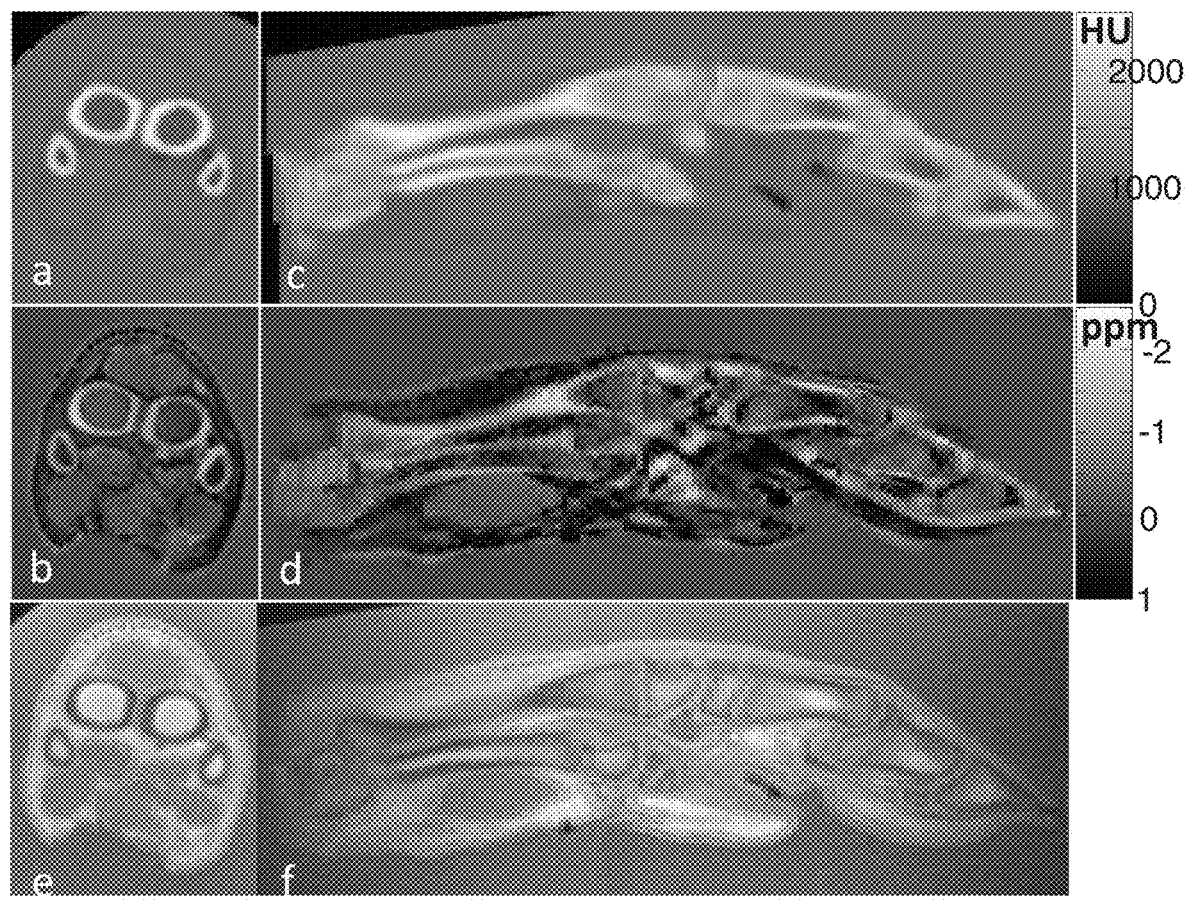
FIGS. 34a-34f. Comparison of CT images (a,c) with correspondent planes of reconstructed QSM (b,d) and ultra-short echo magnitude (e,f). Note the homogeneous diamagnetic appearance of cortical bones and overall fair correspondence between regions of high HU and low susceptibility values.

Porcine phantom results. A susceptibility map of the specimen was successfully reconstructed. Comparison of CT and QSM images is shown in FIGS. 34*a*-34*f* along with results of the ROI analysis (FIG. 33). It should be noted that the good correspondence between diamagnetic regions in QSM and regions of high Hounsfield values in CT images is supported by a strong linear correlation (correlation coefficient $R^2 = 0.77$).

Figures 35A, 35B, 35C:
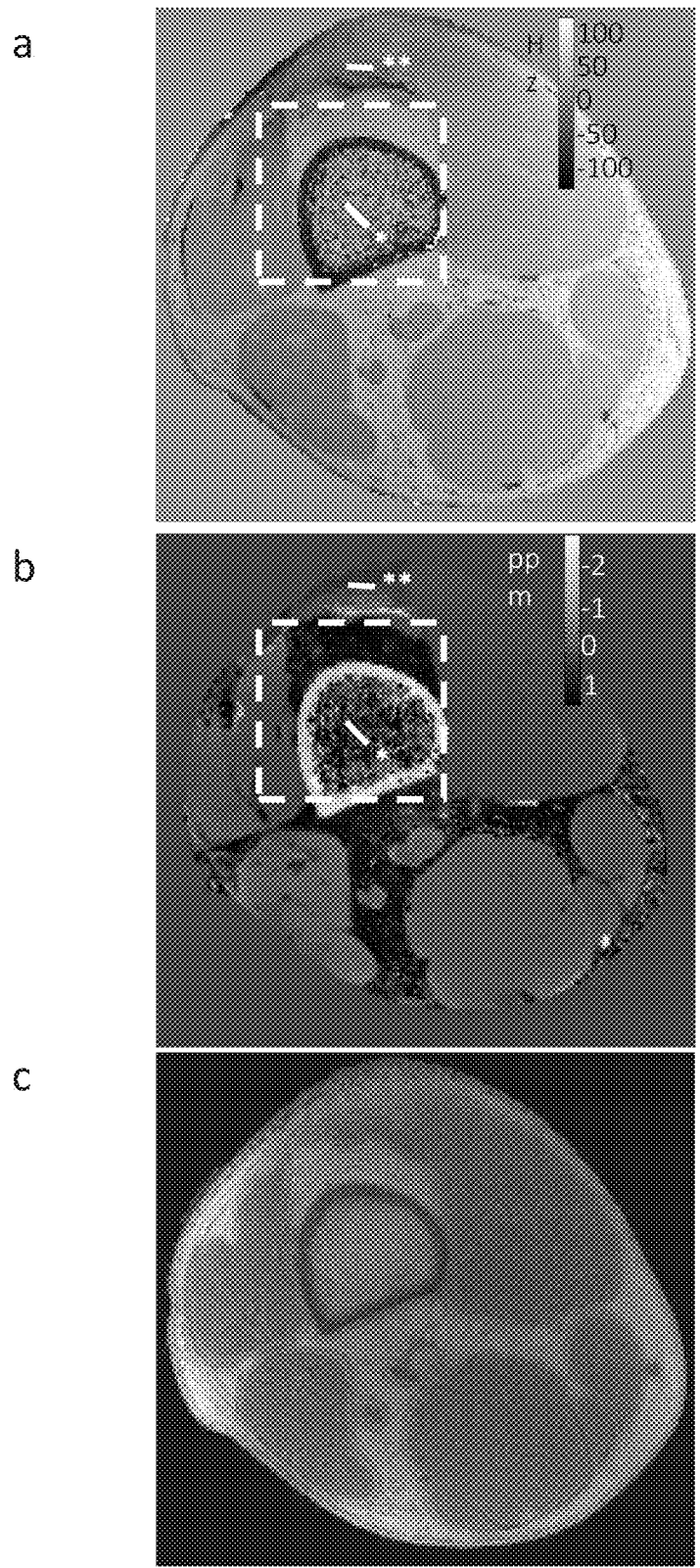
FIGS. 35a-35c. Results of field map reconstruction (a), susceptibility (b) and magnitude of the ultra-short echo (c) for femur data from a healthy volunteer. Overall homogeneous diamagnetic appearance of the cortical bone has been achieved. Notice the visible trabeculation in both the field map and QSM (*), and strong diamagnetism of the quadriceps tendon (**). Please refer to FIG. 36 for further details on the selected area (dashed line).
Figure 36:
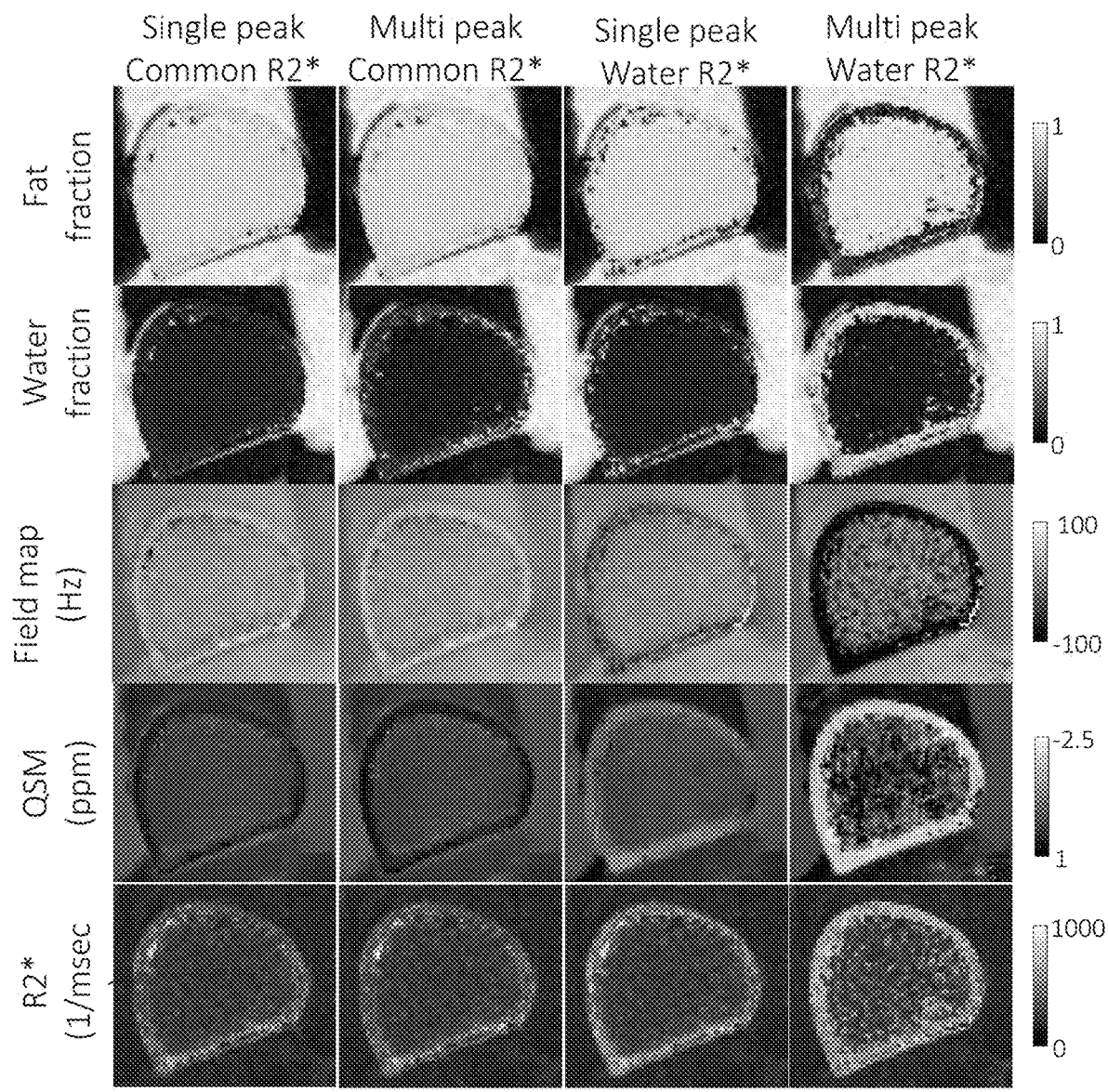
FIG. 36. Comparison of fat and water fraction maps, field maps, QSM and estimated decay rates for different signal models, including single- and multi-peak fat spectrum and common and water-only R2* modeling.

Volunteer results. QSM reconstruction using the proposed method with water-specific $R_2^*$ and multi-peak fat spectrum modelling was successful in all volunteers (see example in FIGS. 35*a*-35*c*). FIG. 36 shows a comparison of the field maps estimated with different techniques and the corresponding calculated susceptibility distributions. Systematic overestimations of the fat fraction within the bone and tendon (up to 80%, compared to negligible lipid content in healthy bones) areas were observed in maps calculated using conventional estimators. These errors were manifested in field and, subsequently, susceptibility maps, leading to significant error in bone and tendon susceptibility values—most notably, in the cortical region of the femur, where bone erroneously appeared to be paramagnetic when assuming either a single fat peak or a common R2* between fat and water. It should also be noted that our proposed technique yielded the best visualization of trabecular bone.

Figure 37:
FIG. 37. Local field (left) and thin slab MIP of knee joint QSM (right) reconstructed using the proposed technique. Good delineation of cortical areas of femur, tibia, and fibula was achieved. Also note the depiction of trabeculation and of the epiphyseal line (*) in the femur. Reconstructed QSM suffers from blur around the knee joint.

FIG. 37 shows a minimum intensity projection of the reconstructed QSM of the knee joint in one healthy subject. Homogeneous diamagnetic appearance of thick cortical areas of the femoral and tibial shafts can be noted. Throughout the entire FOV, trabeculation is well depicted by QSM, demonstrating clear appearance of the epiphyseal plate.

The results of the volunteer scans (Table 1) reveal good intra- and inter-subject agreement of susceptibility values for cortical bone (inter-subject average $\chi_{bone} = -1.4 \pm 0.2$ ppm).

6.5. Conclusions

Our data demonstrate the feasibility of mapping bone magnetic susceptibility including cortical bone, trabecular bone, and marrow. Bone QSM is improved by utilizing a radial UTE gradient echo (GRE) sequence to acquire the rapidly decaying signal of bone water, and a novel bone-specific-R2* in signal modeling to achieve accurate water/fat separation. Results in an ex vivo porcine hoof show excellent correlation with CT. By comparing QSM reconstructions using the current standard signal model with a common R2* for both fat and water components, the bone-specific-R2* approach reduces fat fraction estimation errors within cortical bone and generates realistic susceptibility values for cortical bone in 7 healthy volunteers with excellent depiction of all skeletal tissue components.

Field estimation from UTE and conventional echo GRE data using the conventional IDEAL is non-trivial, prone to noise propagation, and R2* bias. The robust extraction of biophysical parameters from GRE data require proper signal modeling with a minimal number of parameters. Standard GRE signal models assign identical R2* to both water and fat species fail to correctly estimate the field, consequently generating bone QSM with grossly erroneous values (such as paramagnetic bone), because rapid signal decay of bone is misinterpreted as dephasing due to the high fat fraction. We realize that over the echo times acquired in this study, there is negligible R2* decay of the fat signal but rapid R2* decay of water dispersed within the calcified matrix. This leads us to the bone-specific R2* model that accurately reflects the underlying tissue physics, attributing signal decay exclusively to the water component. Both the porcine hoof and human volunteer data show that this bone-specific R2* model when combined with iterative least squares fitting provides reliable estimation of chemical species distribution as well as a biologically plausible field map. Additionally, the application of the multi-peak fat spectrum model further improves quality of the water/fat separation and, consequently, the susceptibility map.

Previous studies show bone magnetic susceptibility can be estimated by a highly regularized piece-wise inversion of the local magnetic field, which may be problematic when there is a local variation in tissue susceptibility. A masked iterative calculation of susceptibility can also be used to estimate distribution of strong magnetic sources in tissue, but the iteration tends to enforce both uniformity and underestimation of high susceptibility structures. Above all, these attempts do not properly account for the underlying fat water biophysics in the MRI signal generation, nor do they acquire signal within bone using UTE, as illustrated in this work. For trabecular bones with densities much lower than those of cortical bones, QSM may be straightforwardly applied using conventional echo times.

Bone mineral density (BMD) assessment is central to the diagnosis of osteoporosis. Currently, BMD is measured using dual energy X-ray absorptiometry (DXA), which may be confounded by factors including degenerative changes, small bone size, and overlaying anatomic structures. Quantitative CT (QCT) has been proposed to overcome these limitations of DXA, but it requires a much higher X-ray dose. A number of non-invasive non-ionizing radiation based methods for characterizing bone tissue are also available. Quantitative ultrasound bone characterization is an important modality for clinical assessment of osteoporotic patients. Several studies have reported use of velocities of axial propagation of ultrasound waves along the shaft of long bones as a biomarker for monitoring of bone fracture healing and bone assessment in osteoporotic patients. Mill-based techniques (such as ZTE and UTE) rely on imaging water bound to the organic matrix of the bone. These acquired signals can provide information on density and porosity of the bone material; this requires separation of bound and free water signal components that have significantly different relaxation constants. UTE imaging with bicomponent analysis has been successfully applied before for ex- and in-vivo cortical bone imaging.

Conventional MRI may be used to assess bone quality but not mineral density. The MRI-based bone QSM presented here may provide BMD assessment without the X-ray radiation. Therefore, our results warrant fixture research in comparing bone QSM with DXA on patients including those suffering from osteoporosis to establish an accurate non-X-ray BMD assessment for predicting fracture risk and guiding therapy. Since comprehensive comparison of QSM as a biomarker with other non-ionizing radiation based measures falls outside of the scope of this paper, additional investigation is required to further assess clinical utility of bone QSM.

The preliminary implementation of including UTE in QSM can be improved with the following consideration. The scan time may be reduced substantially using data acquisition acceleration strategies in Bayesian MRI. This preliminary implementation also assumed that water is the only species experiencing significant decay by the time the last echo is acquired. Although correct in many practical situations when bone matrix bound water is present, this assumption may break down under conditions of strong field inhomogeneity (e.g., imaging near abdominal cavity). These field variations can lead to strong spin dephasing and, as a result, rapid R2* decay in soft tissue regions. In this situation, high order shimming might be required. Additional limiting factor not taken in the account in the present work is the image distortion due to off-resonance frequency of fat. Due to the limited bandwidth, in the radial acquisition used in this study off-resonance manifests itself in blurring of the water/fat tissue interfaces in both magnitude and phase images. This blurring is expected to affect final QSM results, and application of off-resonance correction methods appropriate for non-Cartesian acquisition may be required. Finally, as has previously been reported, QSM is prone to underestimation of strong susceptibility sources, and further adjustments of the imaging protocol (matrix size, resolution) may be necessary to minimize error.

Comparison of the results obtained in the current study with those previously reported in the literature demonstrates possible underestimation of bone magnetic susceptibility obtained with the proposed technique. For example, in authors report bone susceptibility $\chi_{bone} \approx 2.4$ ppm obtained in in vitro experiment. Further, in vivo estimation performed in yielded fairly wide range of values $X_{bone} \in \{-1.8, -2.3\}$ ppm depending on the used reconstruction method. Most notably, this underestimation can be observed around the joints (FIG. 37). Its exact nature of this underestimation may be related to partial voxel effects and abovementioned limitations of the technique, although this issue requires further investigation.

The bone susceptibility, being proportional to CT attenuation coefficients, can be directly used to correct for attenuation in positron emission tomography reconstruction. This would be especially useful for the combined MRI and PET scanner (MR/PET).

In conclusion, quantitative magnetic susceptibility maps across the entire bone cross-section are feasible using a combination of UTE, a conventional TE gradient echo acquisition, and a bone-specific R2* signal model.

7. QSM Cerebral Metabolic Rate of Oxygen Consumption Mapping

Implementations of the abovementioned techniques can be used in a variety of applications. As examples, the following section describes the application of one or more of these techniques to numerical simulation, phantom experiments, and human brain imaging.

7.1 Introduction

Aerobic respiration is the main energy supply for the brain: it is 2% of the adult human body weight, yet it consumes 20% of total oxygen supply. Consequently, oxygen deficiency can easily damage brain tissue, as in hypoxia in Alzheimer's disease (AD) and multiple sclerosis, and ischemia in stroke. qmCMRO2 is specifically valuable for evaluating these brain disorders. For example, in advanced stroke therapy, it is key to identify ischemic penumbra that can be salvaged. Cerebral blood flow (CBF) reduction is problematic for defining the ischemic core. Diffusion perfusion mismatch fails to demonstrate improved clinical outcomes. Oxygen extraction fraction (OEF) elevation in the peri-infarct region is only a weak indicator of tissue outcome. These inadequacies are overcome by CMRO2 (=CBF*OEF*arterial oxygen), which consistently predicts neuron death. Another example is the altered aerobic glycolysis in AD. The measurement of aerobic glycolysis depends in part on the quantitative measurement of oxygen metabolism. The growing concerns of AD in the aging population has generated increased interest in qmCMRO2.

In addition to examining disease, qmCMRO2 has also been an instrumental tool for studying basic brain function. For example, the discovery of the default mode network is arguably the most important advance in our knowledge of brain function in the last two decades, and it has relied on the use of qmCMRO2.

The $^{15}O$ tracer based PET imaging technique has been pioneered by researchers at Washington University (WU) and remains the gold standard for quantitative imaging of brain circulation and metabolism. PET using $^{15}O$-oxygen, $^{15}O$-carbon monoxide, $^{15}$-O-water and $^{18}F$-fluorodeoxyglucose (FDG) provides the only truly quantitative approach to measure human brain circulation and metabolism in health and disease. Although blood oxygenation level dependent (BOLD) fMRI is widely used for qualitative mapping of brain function, the quantitative interpretation of such mapping is difficult. Unfortunately, the short 2-min half-life of $^{15}O$ necessitates onsite production and limits its dissemination in both clinical and research settings.

To address the limitations of $^{15}$O PET, MRI has been investigated for qmCMRO2. CBF can be mapped using spatially selective RFs to generate arterial spin labeling (ASL) or using a contrast agent to label spins, but qmCMRO2 requires additional estimation of deoxyheme concentration ([dH]) from MRI. So far, efforts have been focused on magnitude signal that unfortunately has a complex dependence on [dH]. One insightful idea is to estimate [dH] by mapping blood T2 in the venules using velocity selective labeling, i.e, the quantitative imaging of extraction of oxygen and tissue consumption (QUIXOTIC) method and its variants. However, this approach suffers from problematic flow capture, poor sensitivity, and contamination from arterial blood and cerebrospinal fluid. The [dH] dependence of MRI magnitude signal has been rigorously modeled for an approximate vasculature, i.e., the quantitative BOLD (qBOLD) method, but there is error in approximation and the inverse condition for estimating [dH] is poor. The most widely investigated approach is calibrated fMRI (cfMRI), which empirically models the gradient echo (GRE) magnitude $R_2^*$ decay. The [dH] estimation from $R_2^*$ requires data acquisition during two vascular challenges, typically hypoxia and hypercapnia, which make cfMRI cumbersome to perform in research and difficult to use in clinics. In summary, these MRI based qmCRMO2 techniques have poor sensitivities, use uncertain biological assumptions, or may require complicated vascular challenges. Furthermore, MRI based qmCMRO2 has yet to be validated using PET.

7.2. Theory

QSM Eliminates Empirical Parameters in Current Calibrated fMRI (cfMRI) Based on $R_2^*$.

cfMRI is currently the most widely used MRI approach for qmCMRO2. In cfMRI, the venous deoxyheme concentration [dH] is estimated by modeling the GRE magnitude signal as an $R_2^*$ exponential decay with $R_2^*([dH])$ as:

$$R_2^*([dH]) = \alpha \cdot v \cdot [dH]^\beta + r_0 \quad [34]$$

Here, v is the cerebral venous blood volume; $r_0$ is the signal decay rate when [dH]=0, α and β in Eq.34 are empirical parameters without clear physical meaning, as they depend on field strength and vessel geometries, and require additional data acquisitions using vascular challenges such as hypoxia and hypercapnia. Consequently, the cfMRI approach for qmCMRO2 is very difficult to perform in clinical practice.

We can solve this problem by taking advantage of the typically discarded GRE phase signal, which can be used for quantitative susceptibility mapping (QSM). The magnetic susceptibility χ (QSM) model for estimating [dH] eliminates empirical parameters α and β in Eq.34:

$$\chi = v \cdot \chi_{dH'}[dH] + \eta_0 \quad [35]$$

Here $X_{dH}$=151.054 ppb ml/μmol is the dH molar magnetic susceptibility; $\eta_0$ is the susceptibility when [dH]=0. Therefore, QSM can significantly simplify the cfMRI experiment for qmCMRO2.

Obtaining qmCMRO2 from a QSM analysis of GRE phase data (Eq.35) requires regularization, which can be done using qBOLD with vasculature prior to describe the GRE magnitude data and minimal local variance (MLV) in CMRO2. The uncertainties in the vasculature used in qBOLD and in the MLV of CMRO2 are optimally managed through Bayesian inference. Therefore, qmCMRO2 can be optimally obtained from GRE magnitude and phase data and from ASL data that can be easily acquired on almost every MRI scanner.

Quantitative Mapping of CMRO2 (qmCMRO2) using QSM cfMRI+MLV+Leenders.

For Bayesian estimation for CMRO2, we approximate both data noise and prior uncertainty as Gaussian. qmCMRO2 requires mapping cerebral blood flow (CBF≡$f$) which can be obtained using ASL, and the difference between venous dH concentration [dH] and arterial dH concentration $[dH]_\alpha$ which is oxygen extraction fraction (OEF≡σ=([dH]−$[dH]_\alpha$)/H) scaled by H=7.53 μmol/ml, the heme molar concentration in tissue blood (hematocrit of Hct=0.3567 (straight sinus)). $[dH]_\alpha$=0.02 H=0.15 μmol/ml for 98% arterial oxygenation. Further, with K=$n_{Hb}M_{Hb}C_{Hb}$HctX$_{dH}$=0.0084 L/mol and $\chi_0$=Kv$[dH]_\alpha$/H+$\eta_0$, the CMRO2 equation and Eq.35 become $$CMRO_2 \equiv \varepsilon = = Hf\sigma, \chi Kv\sigma + \chi_2. \quad [36]$$

To optimally estimate CMRO2 ε from ASL data $f$ and GRE phase derived χ, we consider three biological priors: 1) Leenders prior to relate cerebral venous blood volume v to flow data $f$: v=L($f$). 2) In a block much smaller than the Brodmann area or a region of similar cytoarchitecture, gray and white matter may have uniform yet different CMRO2 values. This minimal local variance (MLV) of CMRO2 is consistent with the $^{15}$O PET CMRO2 literature and with the fMRI activation maps. 3) The sum of CMRO2 over gray/white matter tissues is equal to the global CMRO2 measurable in large veins. These three priors can be incorporated into the energy minimization problem to estimate r (and v) as follows:

$$\operatorname{argmin}_{\varepsilon,v} \|w_p((\chi-\chi_0)f - \Gamma L(f)\varepsilon)\|_2^2 + \lambda_1 \|v - L(f)\|_2^{22} + \lambda_2$$
$$\Sigma_\mathbb{b} \Sigma_{i \in \mathbb{b}} (\varepsilon(\mathbb{b}) - \varepsilon i 2 + \lambda 3\varepsilon - \varepsilon 22 \quad [37]$$

Figure 39:
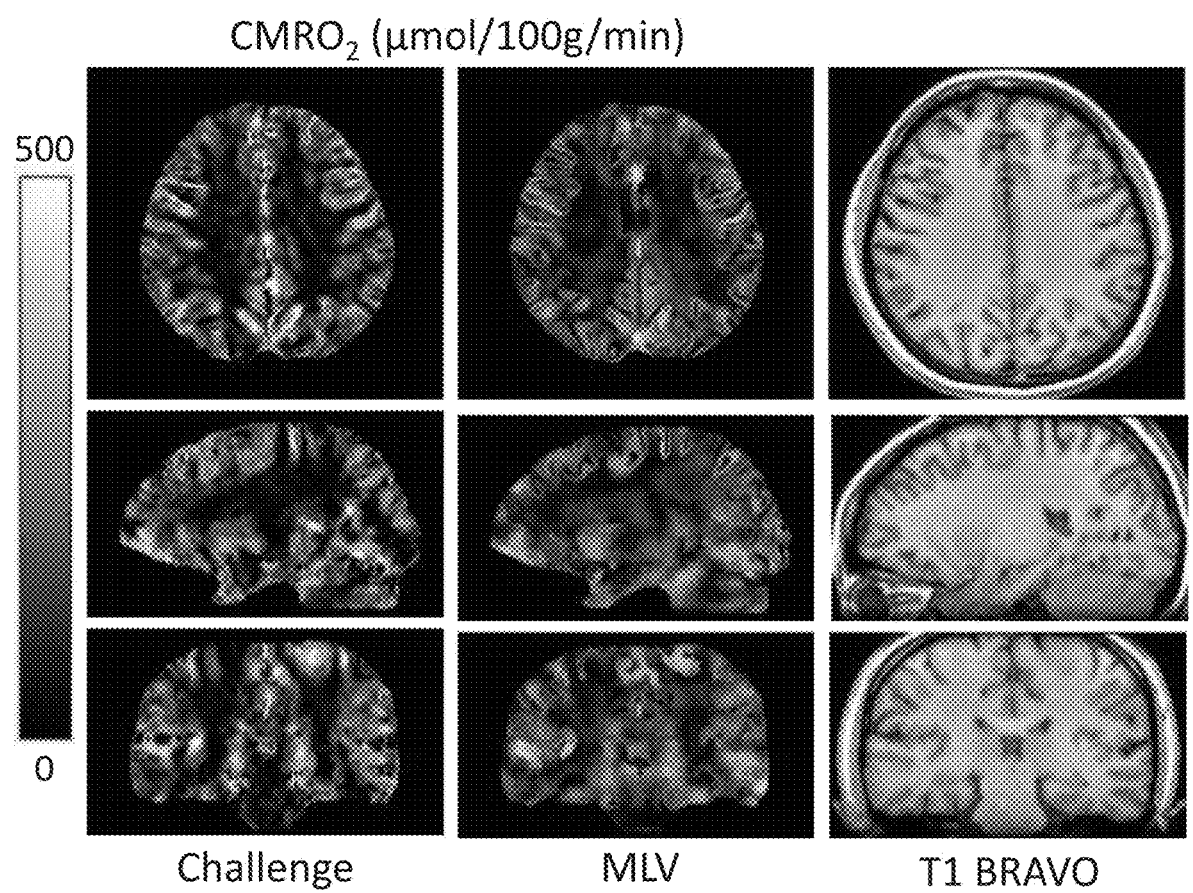
FIG. 39. An example of 3D $CMRO_2$ map in axial, sagittal and coronal section from a healthy subject using caffeine challenge and methods. The corresponding inversion prepared SPGR T1w images are shown on the right. $CMRO_2$ maps of both methods show good consistency and have good gray-white matter contrast in agreement with the inversion prepared SPGR T1w images.

Here, $w_p$ is the inverse of noise in QSM multiplied by $f$, Γ=K/H, $\epsilon(\mathbb{b})$ is the tissue specific average of ε in a block $\mathbb{b}$, and $\bar{\varepsilon}$ is the global CMRO2 measured in veins (averaged). The $1^{st}$ term on the right of Eq.37 is the QSM data fidelity of Eq.36, the $2^{nd}$ term is the Leenders relation between blood flow and volume, the $3^{rd}$ term is the MLV, and the $4^{th}$ term is the consistency with oxygenation measured at large veins. We performed a preliminary test by setting v=L($f$), σ(i)=$\epsilon(\mathbb{b})$/H$f$(i) (block constant ε). Then Eq.37 is simplified to argmin$_c$ $\Sigma_\mathbb{b} \|w_p((\chi-\chi_0)f - \Gamma L(f)\epsilon(\mathbb{b}))\|_2^2 + \lambda \varepsilon - \epsilon \mathbb{b} 22$. By shifting blocks to reduce blockiness, we obtained very encouraging challenge-free MLV results that were comparable with those seen following a caffeine challenge (FIG. 39). In addition to gray/white matter segmentation, MLV may be extended to include segmentation of diseased and normal appearing tissue within each block. We plan to investigate the solution to Eq.37 by carefully choosing regularization parameters according to the discrepancy principle and L-Curve analysis. A preconditioning technique may be applied to speed convergence. A Broyden-Fletcher-Goldfarb-Shanno-Bound (L-BFGS-B) type method will be used to take advantage of the physiological bound of OEF: σ∈[0,1].

The Leenders prior may work well for studying neurophysiology in healthy subjects and may be extended to challenged conditions using the Grubb relation. Disease may decouple blood flow and blood volume, hence, alternative is needed for estimating venous CBV v. Dynamic contrast enhanced MRI only provides total CBV. The vascular space occupancy (VASO) approach can provide v but may be problematic in patients. We will explore the qBOLD approach to over the limitation of the Leenders prior.

Optimal qmCMRO2 using QSM cfMRI+qBOLD+MLV.

The qBOLD approach uses a prior vasculature of randomly oriented tubes that can approximate veins in a voxel for most healthy and diseased tissues. qBOLD has been applied to generate CMRO2 using multi asymmetric spin echo or GRE. qBOLD only utilizes signal magnitude to estimate multiple parameters: σ and v which are relevant to CMRO2, and $S_0$, $R_2$, $\chi_0$ (defined in Eq.38 below) which are not relevant to CMRO2, qBOLD suffers from poor SNR and errors in vasculature assumptions. We propose to utilize the phase data through QSM and the magnitude data through qBOLD. The uncertainties in the qBOLD assumptions and in the MLV and other regularizations can be optimally handled by Bayesian statistics by generalizing Eq.37 as:

$$\operatorname{argmin}_{\sigma,v,S_0,R_2,\chi_0} \|w_p(\chi-\chi_0-Kv\sigma))\|_2^2 + \lambda \Sigma_t \|\|S(t)\| - Q(v,\sigma,S_0,R_2,t)\|_2^2 + \mathcal{R}\, \sigma,v,S0,R2,\chi 0 \quad [38]$$

Here, $Q(v, \sigma, S_0, R_2, t) = S_0 e^{-R_c t}[(1-v)e^{-R_2 t}\mathfrak{F}(v, G\sigma t) + v e^{-R_b(\sigma)t}]$ is the qBOLD mode with $G=(4\pi/3)\gamma B_0 \Delta\chi_0 Hct=51.6$ Hz, $S_0$ the unknown spin density signal scale, $R_c$ the dephasing by field inhomogeneity including voxel sensitivity function effects, $R_2$ the unknown tissue T2 relaxation rate, $R_b$ (σ) the blood T2 relaxation rate with known dependence on [dH], and $\mathfrak{F}$ (v, Gσt). $\mathcal{R}$ (σ, v, $S_0$, $R_2$, $\chi_0$) is the regularization, which includes the MLV in Eq.37, smoothness on $S_0$ and anatomic structural knowledge of $R_2$, $\chi_0$. The MLV idea can be extended to the signal histogram space, for example, to impose minimal variance of or similar σ and $R_2$ over all voxels with similar signal behaviors such as a similar temporal decay trend. Eq.38 will be solved using nonlinear Gauss-Newton optimization as in QSM. We will also investigate the use of the primal dual algorithm to speed up the computation.

7.3. Methods and Materials

The study was approved by the local Institutional Review Board. Healthy volunteers were recruited (n=11, 1 female, mean age 34±12 years) for brain MRI on a 3T scanner (HDxt, GE Healthcare) using an 8-channel brain receive coil. All subjects were instructed to avoid caffeine or alcohol intake 24 hours prior to MRI.

MRI was performed before and 25 min after the oral administration of 200 mg caffeine. The protocol consisted of a 3D fast spin echo (FSE) arterial spin labeling (ASL) sequence, a 3D multi-echo spoiled gradient echo (SPGR) sequence, and an inversion prepared T1w SPGR sequence (BRAVO).

The 3D SPGR sequence parameters were: 20 cm FOV, 3 mm isotropic resolution, 1500 ms labeling period, 1525 ms post-label delay, 62.5 kHz readout bandwidth, spiral sampling of 8 interleaves with 512 readout points per leaf, 35 axial slices, 10.5 ms TE, 4796 ms TR, 3 signal averages, and 6 min scan time.

The 3D SPGR sequence parameters included: 0.52 mm in-plane resolution, 2 mm slice thickness, identical volume coverage as the 3D FSE ASL sequence, 7 equally spaced echoes, TE1=4.3 ms, echo spacing 7.9 ms, TR 56.6 ms, 62.5 kHz readout bandwidth, 15° flip angle, and 7 min scan time. The pulse sequence was flow-compensated in all three directions.

The inversion prepared SPGR T1w sequence parameters were: 1.2 mm isotropic resolution, identical volume coverage as the 3D FSE ASL sequence, TE 2.92 ms, TR 7.68 ms, prep time 450 ms, +19.5 kHz readout bandwidth, 15° flip angle, and 2 min scan time.

CBF and QSM Reconstruction

CBF maps (ml/100 g/min) were generated from the ASL data using the FuncTool software package (GE Healthcare, Waukesha, Wis., USA). For QSM reconstruction, an adaptive quadratic-fit of the GRE phase followed by a projection onto dipole fields was used to obtain the local field map. Susceptibility was computed from the local field map using the Morphology Enabled Dipole Inversion (MEDI) algorithm. Susceptibility values were referenced to the susceptibility of water, as estimated in the cerebrospinal fluid (CSF) masks (see below). All images were co-registered and interpolated to the resolution of the QSM maps using the FSL FLIRT algorithm.

$MRO_2$ and OEF Reconstruction

According to mass conservation of oxygen molecules, the cerebral metabolic rate of oxygen $CMRO_2$ (μmol/100 g/min) can be expressed as $$CMRO_2 = CBF \cdot ([dH]_v - [dH]_a) \quad [39]$$

where CBF is the cerebral blood flow (ml/100 g/min) and $[dH]_v$ and $[dH]_a$ are the deoxyheme molar concentration (μmol/ml) in venous and arterial blood, respectively.

Oxygen Extraction Fraction (OEF) is the percentage of oxygen extracted from arterial blood and can be expressed as $$OEF = \frac{[dH]_v - [dH]_a}{[H] - [dH]_a} \quad [40]$$

where [H]=7.53 μmol/ml is the heme molar concentration in tissue blood assuming a tissue blood hematocrit of $Hct_{tissue}$=0.357, which is estimated from an assumed hematocrit of $Hct_{ss}$=0.47 in the straight sinus and a Hct ratio of 0.759 between large vessel and brain tissue. $[dH]_a$=0.15 μmol/ml assuming 98% arterial oxygenation. Calculation of heme concentration ([H]) in tissue blood $$[H] = 4 Hct_{tissue} \frac{\rho_{RBC,Hb}}{M_{Hb}} = 7.53 \text{ μmol/ml}$$

Where 4 account of 4 heme per Hb, $Hct_{tissue}$=0.357, $\rho_{RBC,Hb}$=0.34 g/ml is mass concentration of Hb in a red blood cell, $M_{Hb}$=64450×10$^{-6}$ g/μmol is the the molar mass of dHb.

Calculation of $\chi_o$ $$\chi_o = CBV \cdot X_{ba} + CBV_a \cdot X_{dH,mol} \cdot [dH]_a$$

Here $CBV_a$=CBV−$CBV_v$=0.23 CBV is the arterial blood volume fraction. $[dH]_a$=0.15 μmol/ml is [dH] in arterial blood assuming 98% oxygenation. $X_{ba}$ is susceptibility of 100% oxygenated blood.

$$X_{ba} = Hct_{tissue}\delta_{Hb} \cdot X_{oHb} + (1 - Hct_{tissue}\delta_{Hb})X_p = -108.3 \text{ ppb}$$

Where $\delta_{Hb}$ is volume fraction of Hb in RBC.

$$\delta_{Hb} = \frac{\rho_{RBC,Hb}}{\rho_{Hb}} = 0.255$$

Here $\rho_{RBC,Hb}$=0.34 g/ml is Hb mass concentration in a red blood cell. $\rho_{Hb}$=1.335 g/ml is Hb density in pure aggregate. $X_{oHb}$ is volume susceptibility of oxyhemoglobin (OHb). $X_{oHb}$=−4 $\pi\rho_{Hb}$(0.587×10$^{-6}$ ml/g)−(−9035 ppb)=−813 ppb. 0.587×10$^{-6}$ ml/g is mass susceptibility of globin relative to vacuum in CGS unit. 4π is for unit conversion from cgs to si units. −9035 ppb is water volume susceptibility relative to vacuum. $X_p$=−37.7 ppb are the oxyhemoglobin and blood plasma volume susceptibility. $[dH]_v$ in Eqs. 39 and 40, and subsequently $CMRO_2$ can be mapped using QSM.

$$CMRO_2 = CBF\left(\frac{\chi - \chi_{nb} - \chi_0}{CBV_v \cdot X_{dH,mol}} - [dH]_a\right) \quad [41]$$

Here, $\chi$ is the magnetic susceptibility mapped using QSM. $X_0$ reflects the susceptibility contributions from pure oxygenated blood and arterial deoxyhemoglobin. $CBV_v$ is the venous blood volume fraction, estimated as 77% of total CBV.

$X_{dH,mol}$=151.054 ppb ml/μmol is the molar magnetic susceptibility of dH.

In Eq. 41, $CMRO_2$ and $\chi_{nb}$ are the two unknowns. In previous studies, susceptibility and blood flow of baseline and challenged brain states were mapped. Hence, $CMRO_2$, $\chi_{nb}$, and subsequently OEF can be solved. However, CBF challenges such as caffeine administration are time-consuming, presenting difficulties when performing in patients.

To solve this limitation, the QSM and CBF maps were segmented into small blocks and each block was further segmented into two tissue types (gray and white matter) using T1 weighted images. Within each block and each tissue type, $\chi_{nb}$ and $CMRO_2$ are assumed to be constant. This assumes that, within a small local region, the same tissue type has similar biological and chemical makeup. Hence, $CMRO_2$ and $\chi_{nb}$ of each block and tissue type can be organized into into a vector of unknowns x in a linear system format:

$$\underbrace{\begin{bmatrix} \psi_1 & 1 \\ \psi_2 & 1 \\ \vdots & \vdots \\ \psi_N & 1 \end{bmatrix}}_{A} \underbrace{\begin{bmatrix} CMRO_2 \\ \chi_{nb} \end{bmatrix}}_{x} = \underbrace{\begin{bmatrix} \phi_1 \\ \phi_2 \\ \vdots \\ \phi_N \end{bmatrix}}_{b}$$

Here $\psi = CBV_{v,i} \cdot X_{dH,mol}/CBF_i$ and $\phi_i = \chi_i - CBV_i \cdot (X_{ba} + X_{dH,mol} \cdot [dH]_a)$. The index i=1, ..., N denotes the $i^{th}$ voxel of a given tissue type with a block with N the total number of such voxels in that block. $X_{ba}$=−108.3 ppb is the susceptibility of fully oxygenated blood.

In the following, this algorithm will be referred to as minimum local variance (MLV). To reduce error propagation and improve convergence speed, a right preconditioning technique is applied. The new system is defined as $A_P x_P = b$, where $A_P = AP$ and $x_{P=P^{-1}}x$. P is the preconditioner defined as $P = \text{diag}(CMRO_{2,ub}, \text{avg}(\chi))$ which is designed to allow the elements of $x_P$ to have similar order of magnitude. $CMRO_{2,ub}$ is the upper bound of $CMRO_2$ calculated within each block using Eqs. 39&40 using OEF=1. $\text{avg}(\chi)$ denotes the average of susceptibility of voxels within a block that are of the same tissue type.

The solution for a given tissue type (grey or white matter) was obtained by minimizing the following cost function over the whole brain using a limited-memory Broyden-Fletcher-Goldfarb-Shanno-Bound (L-BFGS-B) algorithm with physiological bounds on $CMRO_2$.

$$x = \underset{x}{\arg\min}\{\|Ax - b\|_2^2 + \lambda(CMRO_2^{global} - \overline{CMRO_2})^2\} \quad [42]$$

with $0 \leq CMRO_2 \leq CMRO_{2,ub}$

A is $\text{diag}(A_P)$, a block-wise diagonal matrix with the matrix $A_P$ for the given tissue type and for each block along the diagonal, and x, b, and $CMRO_2$ are the concatenated column vectors of $x_P$, b, and $CMRO_2$ for that same tissue type and for each block, respectively. In the second term, $\overline{CMRO_2}$ is the average $CMRO_2$ across all blocks for the given tissue type. This term imposes a global physiological constraint based on mass conservation: the global $CMRO_2$ estimated from the $CMRO_2$ map should be similar to that estimated from straight sinus. Here, $CMRO_2^{global}$ is estimated from Eq.41. Global cerebral blood flow was estimated by averaging CBF over all brain voxels. The magnetic susceptibility of venous blood in the straight sinus (SS) was measured in ROIs drawn by a neuroradiologist with 10 years' experience (A.G.) and taking $CBV=CBV_v=100\%$, $\chi_{nb}=0$ and $Hct_{ss}=0.47$ since only venous blood was present in these ROIs λ is the regularization weighting parameter on the global constraint, chosen based on the average value obtained by L-curve analysis in three randomly selected subjects.

Whole brain grey matter (GM), white matter (WM), and CSF masks were created using the FSL FAST algorithm on the inversion prepared SPGR T1w images. These masks were further divided into 6×6×6 mm³ isotropic blocks. This block based computation was performed for the GM and WM separately, selecting within each block only those pixels that belong to the corresponding tissue type. This allowed a proper convergence when solving Eq.38. To minimize potential bias due to specific block grids, blocks were shifted in (3D) diagonal directions 4 times with a step size of 1.5 mm. The data were reprocessed and the results were averaged to obtain the final images.

$CMRO_2$, OEF, and $\chi_{nb}$ were also solved as follows. Briefly, assuming $\chi_{nb}$ remained the same before and after challenge, susceptibility and CBF measurements of each voxel in baseline and challenged states were paired to solve OEF and $\chi_{nb}$ for every voxels using LBFGS-B solver with identical OEF/$CMRO_2$ bounds and global $CMRO_2$ constraint as the proposed method. The percentage change of $CMRO_2$ between the two states were estimated in the straight sinus and incorporated into the minimization.

For this feasibility study, CBV was estimated from CBF based on a linear regression derived from CBF and CBV measurements in gray and white matter using $^{15}O$ Positron Emission Tomography (PET) in healthy subjects (n=34): CBV=(0.0723 CBF+1.144)/100. Post caffeine CBV was estimated from baseline CBV using the Grubb's exponent of 0.38 because the empirical CBF and CBV relationship derived from PET data was from healthy subjects without vaso-challenges and may not be suitable for estimating post caffeine CBV. CBV changes after challenge were assumed to be on arterial side as suggested in the literature.

Statistical Analysis

Cortical grey matter (CGM) was segmented into the bilateral anterior (ACA), middle (MCA) and posterior cerebral artery (PCA) vascular territories (VT) by the same neuroradiologist (A.G.). For each ROI, the mean and standard deviation of $CMRO_2$ and OEF values were measured. Bland-Altman plots and paired sample t-tests were performed to compare $CMRO_2$ and OEF values in the VTs using previous and proposed methods. P values lower than 0.05 were considered to indicate statistical significance. All data were expressed as mean±standard deviation.

Numerical Simulation

Numerical simulation was performed to investigate CMRO2 estimation error caused by 1) CBF error, 2) partial volume effect, and 3) QSM error. One block with matrix size of 8×8×5, the same block size in this study, was constructed. The upper and lower half was set to be white (WM) and gray matter (GM), respectively. Inputs were CMRO2, $\chi_{nb}$, and CBF (ground truth): CMRO2 of GM: 181, CMRO2 of WM: 138 (μmol/100 g/min), $\chi_{nb}$ of GM: 0.02, $\chi_{nb}$ of WM: 0.45 WM (ppb). CBF values are given voxel-wise with normally randomized values, 49.5±4.3 for WM and 64.8±3.6 for GM (ml/100 g/min). These values were the average values in a subject and, for the CBF standard deviation, the whole GM and WM standard deviation was calculated and divided by five to obtain a reasonable estimation for the same tissue type in small brain region. The QSM was subsequently estimated voxel-wise with the given CMRO2, $\chi_{nb}$, and CBF values. 1) To investigate the CBF error propagation in CMRO2 map, we considered two cases; 1-1) low SNR CBF and 1-2) biased CBF. For low SNR case, noise was added to CBF (SNR: 4.5), and MLV was performed subsequently. This was repeated 100 times to obtain average and standard deviation. CBF SNR was estimated the ratio of mean over standard deviation in the caudate nucleus, 4.5±1.7 (n=5). 2) To investigate the partial volume effect within individual voxels, the QSM and CBF value at the GM boundary layer was averaged with an immediate neighboring WM QSM and CBF value, respectively. This means that GM boundary voxel actually consisted of half GM and the other half WM, but was treated as GM. 3) To estimate QSM error propagation into CMRO2 estimation, noise was added to QSM (SNR 3.1, estimated in the same way as CBF SNR). This was repeated 100 to obtain average and standard deviation. For all cases, global CMRO2 constraint weighting ($\lambda$) was set to be 500 as used in this study.

7.4. Results

Figures 38A, 38B:
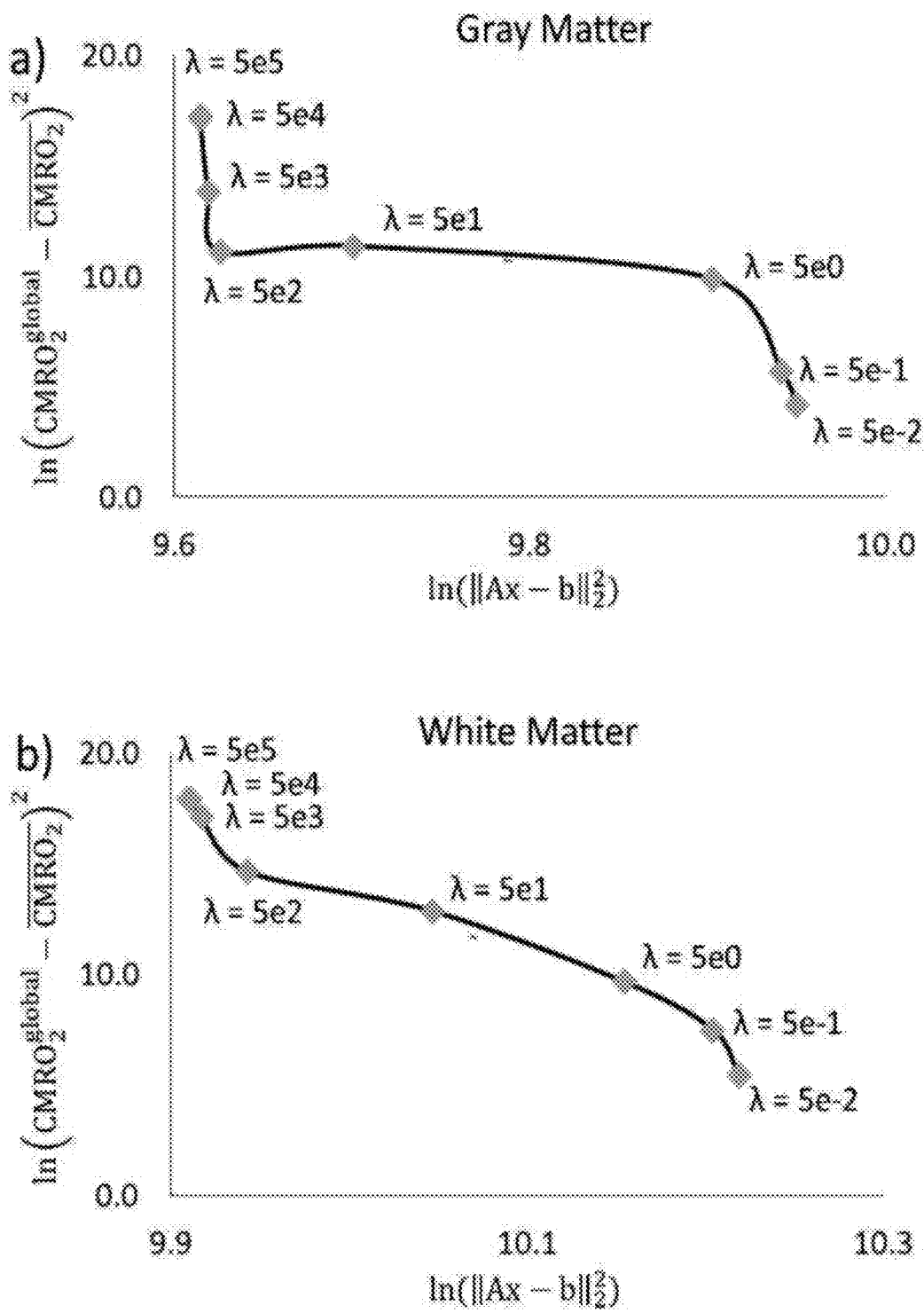
FIGS. 38a-38b. The figure shows the averaged L-curves of the three randomly selected subjects using MLV method. λ (Eq.42) was chosen to be 500.

FIGS. 38a-38b shows the averaged L-curves of the three randomly selected subjects using MLV method. $\lambda$ (Eq.42) was chosen to be 500. In CGM, CBF decreased by 16.3+7.0 ml/100 g/min (p<0.01) after the caffeine challenge. CMRO$_2$ in CGM was 142±16.5, and 139±14.8 μmol/100 g/min for the caffeine challenge based method and the MLV based method, respectively. These corresponded to OEF$_{base}$ of 33.0±4.0%, and 31.8±3.2%, and to OEF$_{chal}$ of 39.0±4.9%, and 39.3±4.1%, respectively.

FIG. 39 shows CMRO$_2$ maps reconstructed using the caffeine challenge based and the MLV based methods across the brain in one healthy volunteer, next to the corresponding inversion prepared SPGR T1w images for anatomical reference. CMRO$_2$ maps show good consistency and the gray-white matter contrasts are in reasonable agreement with anatomical images.

Figure 40:
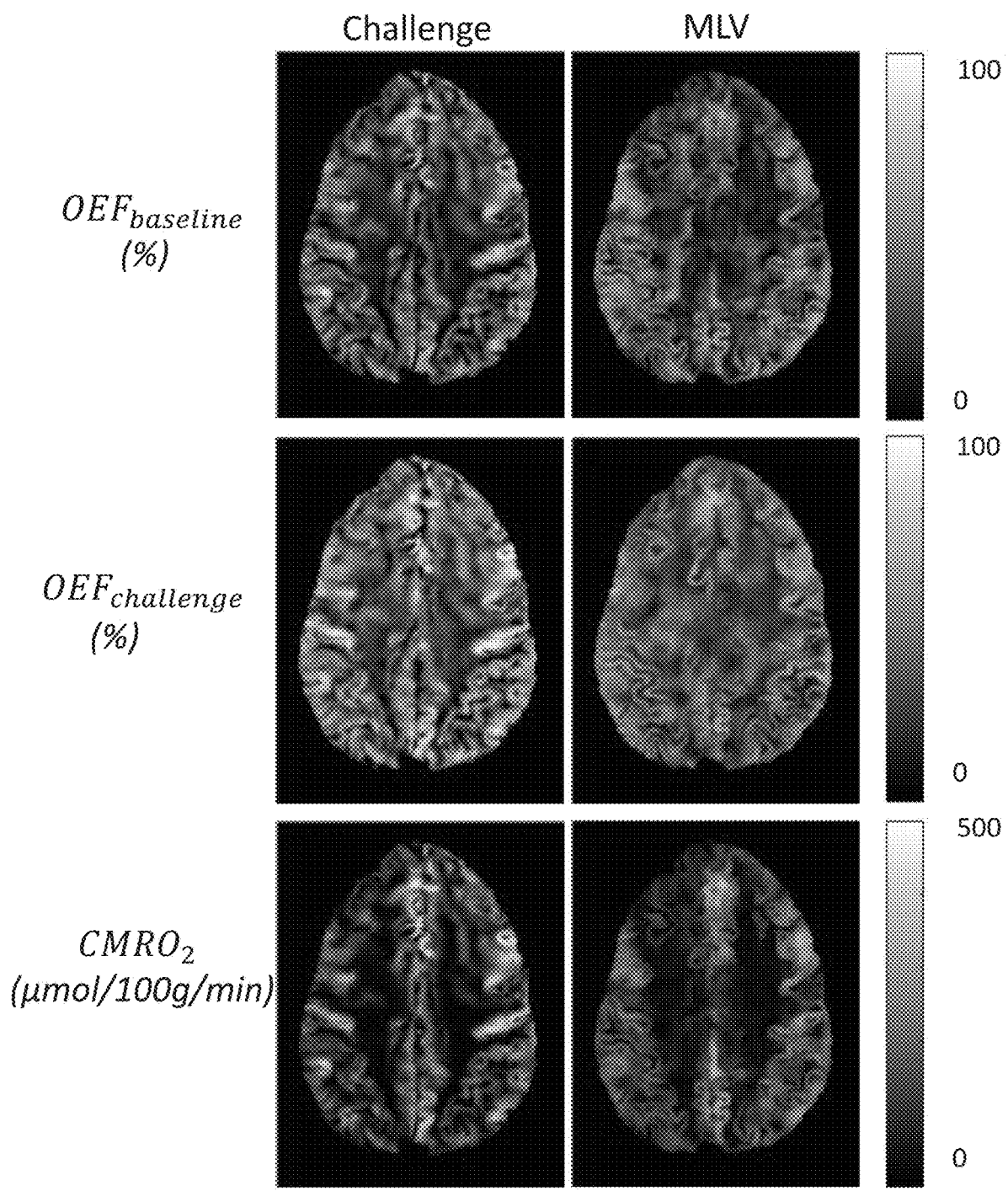
FIG. 40. An example of OEF and $CMRO_2$ maps in a second subject reconstructed using the challenge based (left) and MLV based (right) method.

FIG. 40 shows OEF$_{base}$, OEF$_{chal}$, and baseline CMRO$_2$ maps of a second subject reconstructed with the caffeine challenge and MLV methods. OEF maps also demonstrate good consistency between the different reconstruction methods. A global increase in OEF coinciding with the caffeine-induced global CBF decrease can be readily appreciated.

Figures 41A, 41B, 41C:
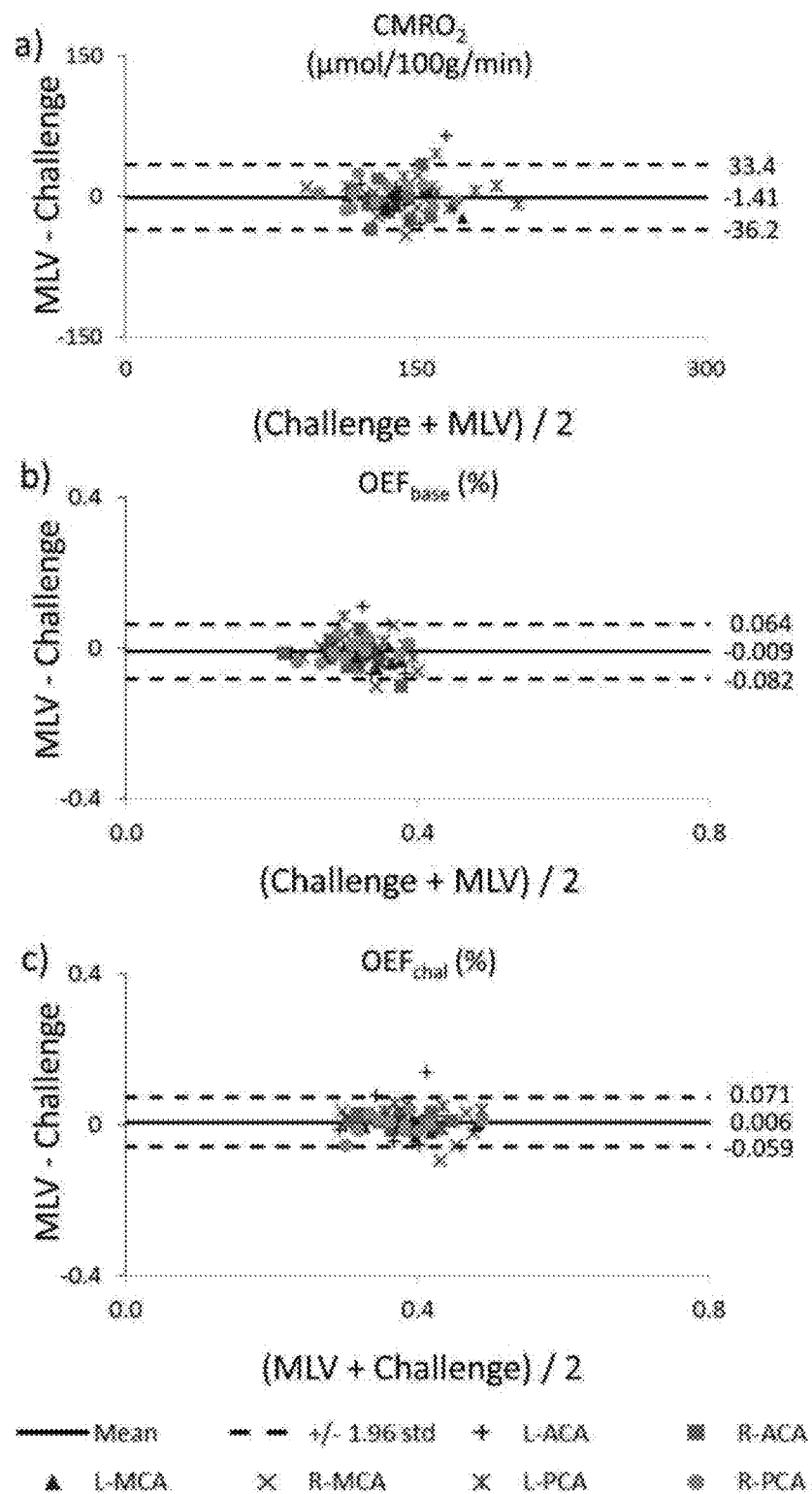
FIGS. 41a-41c. Bland-Altman plots comparing $CMRO_2$ and OEF maps reconstructed using the challenge based and the MLV based method. Small bias (<4% of the average of the two measurements) are detected in all comparisons without statistical significance (p>0.05).

FIGS. 41a-41c shows the Bland-Altman plots comparing CMRO$_2$ and OEF values in VT between the caffeine challenge based and the MLV based method. These comparisons show <4% difference of the average of the two measurements without statistical significance (p>0.05).

Numerical simulation showed that CMRO2 estimation error was affected by low SNR CBF and by biased CBF. In the case of low SNR CBF (SNR 4.5), CMRO2 error was 6.0% for GM and 4.4% for GM. In the case of biased CBF (10% underestimation), relative CMRO2 error for both GM and WM was 10%. In terms of the partial volume effect at the GM boundary, the relative CMRO2 difference was 3.0% for GM and $2.2\times10^{-5}$% for WM. In case of the QSM noise propagation into CMRO2 (SNR 3.1), the resultant CMRO2 error was 0.1% for WM 1.5% for GM.

7.5. Conclusions

Our preliminary results demonstrate the feasibility of a noninvasive CMRO$_2$ mapping without a vascular challenge based on QSM and CBF using MLV. The CMRO$_2$ measurements agrees well between the challenge and MLV methods in healthy subjects. The elimination of the vascular challenge greatly reduces the complexity of the scanning protocol, the overall exam time and the potential risks associated with the administration of agents that modify blood flow.

Previously reported R$_2$*-based CMRO$_2$ mapping methods are limited by R2* modeling for [dH]. Calibration of the model parameter is required, which may vary with scanning parameters such as field strength. Consequently, measurements at three brain states (normoxia, hypercapnia, and hyperoxia) are needed for quantitative CMRO$_2$ mapping. However, it is very cumbersome to administer stimulants to the brain to generate three distinct states. Magnetic susceptibility has a completely defined linear relation with [dH], eliminating the R2* model parameter calibration and reducing the number of required brain states for CMRO$_2$ mapping to two. The two brain states are needed to separate the susceptibility contribution from blood and non-blood tissue and can be achieved using vascular challenges, such as by administering caffeine or using hyperventilation. However, even administering a single challenge can be cumbersome in practice. Using MLV quantitative CMRO$_2$ map can be obtained without such a challenge, making CMRO$_2$ more feasible to perform in practice.

The MLV implemented in this study used an isotropic block size of 6×6×6 mm$^3$ such that multiple CBF voxels, acquired at a 3×3×3 mm$^3$ isotropic resolution, were available within each block. In 1909, Brodmann divided the human cerebral cortex into 44 areas according to its cytoarchitecture, which were later shown to be related to various neural functions. In this study, the cerebral cortex was divided into more than 4000 regions. Hence, the assumptions of constant CMRO$_2$ and $\chi_{nb}$ within the same block and tissue type may be considered as reasonable. This MLV implementation then resulted in multiple data points to uniquely estimate the two unknowns CMRO$_2$ and $\chi_{nb}$ within each block. There is substantial amount of noise propagation from the CBF and QSM input to the CMRO$_2$ output, which can be further reduced using a global CMRO$_2$ constraint as the regularization in Eq.42.

There are several limitations in this study. In MLV, $\chi_{nb}$ and CMRO$_2$ are assumed to be constant within each block and each tissue type. Therefore, MLV derived CMRO$_2$ values are block-wise constant and depend on accurate tissue segmentations. MLV may be further improved by considering physiologically relevant brain parcellations. The rationale for choosing 6×6×6 mm$^3$ isotropic blocks was that, for this data set, each block contained exactly 2×2×2 CBF and 12×12×3 QSM, both deemed large enough to avoid ill-posedness but not too large to avoid violating the homogeneous tissue assumptions. The block size was chosen to balance between these competing demands. To investigate the effect of block size, we applied different block-sizes (2×2×2 mm$^3$ and 9×9×9 mm$^3$) for one subject. CMRO2 values for cortical GM were 119.0±107.5, 123.5±83.2, and 124.8±64.2 μmol/100 g/min for 2 mm, 6 mm, and 9 mm block size respectively. As the block size increases, the standard deviation of CMRO2 decreases. Averaging over several sub-block shifts, as done in this work, suppresses the resulting piecewise constant appearance. Nevertheless, sharp transitions remain between different tissue zones (FIG. 39), since computations are performed for each tissue type separately. Tissue segmentation can be challenging in patients, which might cause error. Further investigation regarding the other potential complexities in patients, e.g. difficulties in capturing regional variation within a lesion, also needs to be investigated. Another MLV limitation is the possibility that highly deoxygenated vein contribution might be smoothed out with using block based method. If some voxels in the same tissue type have strong contribution from highly deoxygenated vein, it's possible that this effect is smoothed out by the other voxels with low vein contribution. One possible way to avoid this issue would be to remove the highly deoxygenated large veins from gray and white matter mask in the implementation of MLV. The lack of Hct measurement is another limitation. We assumed $Hct_{ss}=0.47$. We have quantified the maximum CMRO2 estimation error caused by inter-subject variability by repeating calculations for both the lower (0.38) and upper bound (0.52) of the expected human Hct range. For the cortical GM, the maximum CMRO2 difference between Hct=0.47 and the two bound cases was 2.45±0.89 (n=11). Another limitation is that QSM-based $CMRO_2$ does require CBV measurements as in R2* based methods. Our MLV feasibility study here used CBV estimated from CBF assuming an empirical relationship derived from normative PET data and assumed a 0.77 ratio between venous and total CBV, as in previous R2* and QSM studies. While both these assumptions are consistent with the literature on healthy subjects, they may be invalid in some patients. Also, the accuracy of CBF measurement by ASL might suffer from low SNR in WM or with large veins and long arterial transit times. Our simulation showed that CMRO2 estimation would be affected by low SNR CM (4.4% error in WM with SNR 4.5) and biased CBF values (10% error in both WM and GM with 10% underestimation). This may be addressed by a direct measurement of CBV using dynamic contrast enhancement (DCE) or a non-contrast MRI technique such as Vascular Space Occupancy (VASO), multiphase ASL based CBVa or quantitative BOLD. Another limitation of study is the use of straight sinus OEF for global CMRO2 constraint. Jugular veins would more ideal to estimate the global CMRO2 but are more complicated to images within the same field of view and/or coil. Moreover, QSM outside the brain remains challenging due motion and the need for additional phase preprocessing such as water-fat separation. Therefore, measurements in straight sinus are used under the assumption that straight sinus and jugular veins have similar oxygenations, given that OEF has been shown uniform in healthy subjects across the brain using $^{15}O$ PET. Because of the use of flow compensation during acquisition and the adaptive quadratic fitting of the field (Xu B et. al., MRM 2014) flow effects on QSM are minimized. Finally, the subject in this study were young and healthy, and the validation and applicability of this technique in a general patient population remains to be investigated.

In summary, our study demonstrated the feasibility of a noninvasive $CMRO_2$ mapping without vascular challenge based on QSM and CBF using MLV. In vivo imaging in heathy subjects demonstrates that the $CMRO_2$ and OEF maps obtained with the proposed MLV method agree well with those obtained using a blood flow challenge based method.

8. QSM of the Heart

In this section, we present QSM of the heart magnetic susceptibility source using navigator gating data acquisition.

8.1. Introduction

Mixed-venous oxygen saturation (SvO2) measures the percentage of oxyhemoglobin that returned to the right ventricular chamber after circulated through the vascular system. It reflects the balance between global oxygen delivery and global oxygen consumption, making it an important measure of cardiopulmonary function that is widely used to manage critically ill patients. Currently, measurement of SvO2 requires an invasive pulmonary artery catheterization procedure. Thus, a method for using non-invasive MRI to measure SvO2 may be of interest for improving patient care.

Quantitative Susceptibility Mapping (QSM) is a MRI contrast mechanism capable of quantifying the difference between diamagnetic and paramagnetic materials. Due to the difference between the number of unpaired electrons in the iron, oxyhemoglobin is diamagnetic and deoxyhemoglobin are paramagnetic. This allows QSM to be used to quantify the oxygen saturation level of blood in the body. However, in vivo QSM has yet to be applied to the heart due to three major challenges: cardiac and respiratory motions, fat chemical shift in the chest and heart, and background field. Here, we will describe our methods for overcoming these challenges to generate in vivo cardiac susceptibility maps, and use it to quantify the relative difference between the oxygen saturation level in the LV blood and RV blood.

8.2. Materials and Methods

Cardiac and Respiratory Motions:

Motion has always been a problem for cardiac MRI, and even more so for cardiac QSM, due to the need for long TR. To suppress cardiac motion, we used an ECG triggered sequence, and limited the acquisition window to be less than 200 ms within diastole. To suppress respiratory motion, we asked the volunteers to preform breath-holds during the scan. The volunteers were asked to hold their breaths at maximum exhalation to ensure that each slice was acquired at the same respiratory position.

We also developed a free-breathing navigator method. An ECG-triggered navigator gated multi-echo 3D FGRE sequence was developed for cardiac QSM on a 1.5T scanner (GE Healthcare). A pencil beam navigator echo was used to detect the diaphragm position, and an efficient 2-bin phase-ordered automatic window selection (PAWS) gating algorithm[2] was used to control the data acquisition based on the diaphragm position in real time. Two navigator echoes were played each heartbeat, one right before acquisition and one right after acquisition. If the difference between the two diaphragm positions detected by these two navigator echoes was greater than 2 mm, then the data acquired in this heartbeat was rejected. We compared the 2DBH and 3DNAV approaches for cardiac QSM in healthy volunteers.

The scan parameters for the 2DBH approach were as the following: $1^{st}TE/\Delta TE/\#TE/TR/BW$=1.5 ms/2.2 ms/5/15 ms/±62.5 kHz, acquisition resolution=192×192 with 75% phase FOV, 20 slices, 5 mm slice thickness, and 10 views per heartbeat. The scan parameters for 3DNAV were the same except that 24 slices were acquired with 0.75NEX and 0.75 partial slice encoding.

Five healthy volunteers, each consented with IRB approved protocol, were scanned with the 2DBH sequence, in which they were asked to perform breath holds at maximum exhalation, and the 3DNAV sequence, in which they were freely breathing.

The total field was obtained from the complex data from a chemical shift update method[3], which was initialized by the output of a graph-cut based phase unwrapping and fat-water separation method[4]. Then QSM was reconstructed using the Total Field Inversion Method.

A successful dipole inversion requires a continuous 3-dimensional field as the input, so consistent breath holds for every slice is necessary to ensure such conditions are met. To simulate the effect of misregistration on QSM, we retrospectively performed an in-plane shift (1.0 min in both x and y directions) on a middle slice from one stack of images that were acquired with consistent breath holds, and then computed the QSM.

Fat Chemical Shift:

Fat in the body produces artificial phase shifts, or chemical shift. If these chemical shifts are not removed prior to reconstructing QSM, the resulting QSM will have severe streaking artifacts. To accurately remove fat chemical shift, we first employed a magnitude image guide graph cuts method, for phase unwrapping and initial estimation of chemical shift. The joint field map estimation and water fat separation problem can be formulated as the following nonlinear least squares fitting problem of the complex MRI data with water and fat as the tissue chemical composition.

$$R_0(\rho_W, \rho_F, f_s, R_2^*) = \sum_{n=1}^{N} \|s(TE_n) - e^{-R_2^* TE_n} e^{-i2\pi b TE_n} (\rho_W + \rho_F e^{-i2\pi f_F TE_n})\|_2^2 \quad [43]$$

where $s(TE_n)$ is the measured MR signal at a certain echo time $TE_n$, $R_2^* = 1/T_2^*$ is the decay rate, $f_F$ is the presumed fat chemical shift ($f_F \approx -220$ HZ for 1.5T or $-440$ HZ for 3T scanner), b is the field map (or field inhomogeneity), $\rho_W$ is the water component, and $\rho_F$ is the fat component. The above objective function is a non-convex function having multiple local minima. The solution to this minimization is especially sensitive to the initial guess of b. The complex signal generated by the two species can be formulated as $s(TE_n) = \alpha(TE_n) e^{-i2\pi b TE_n - i\theta(TE_n)}$, where $\alpha(TE_n) = e^{-R_2^* TE_n} \sqrt{\rho_W^2 + \rho_F^2 + 2\rho_W \rho_F \cos(2\pi f_F FE_n)}$ is the magnitude of $s(TE_n)$ and $$\theta(TE_n) = \arctan \frac{\rho_F \sin(2\pi f_F TE_n)}{\rho_W + \rho_F \cos(2\pi f_F TE_n)}$$

is the phase of $(\rho_W + \rho_F e^{i2\pi f_F TE_n})$. We assume $\rho_W$ and $\rho_F$ are real number for simplicity. An effective $\tilde{f}$ may be estimated using a single species fitting, and here we study the relationship between $\tilde{f}$ and the true $f_s$. We aim to minimize the following residual function, which uses a single species model to fit the two species signal $$\tilde{f} = \arg\min_f \sum_{n=1}^{N} \|\alpha(TE_n) e^{-i2\pi b TE_n - i\theta(TE_n)} - \alpha(TE_n) e^{-i2\pi f TE_n}\|_2^2 \quad [44]$$

For this nonlinear least square fitting problem, it is difficult to compute the analytical solutions, so here we provide an approximate analytical solution. Briefly, we use Taylor expansion to the first order near b and set the derivative of the residual function to zero to get the approximate solution $$\tilde{f} = \begin{cases} b + \dfrac{\sum_{n=1}^{N} a^2(TE_n) TE_n \theta(TE_n)}{\sum_{n=1}^{N} 2a^2(TE_n) * \pi TE_n^2} - k/\Delta TE, & |\rho_W| \geq |\rho_F| \\ (b + f_F) + \dfrac{\sum_{n=1}^{N} a^2(TE_n) TE_n \theta'(TE_n)}{\sum_{n=1}^{N} 2a^2(TE_n) \pi TE_n^2} - k/\Delta TE, & |\rho_W| < |\rho_F| \end{cases} \quad [45]$$

where $\theta'(TE_n) = \arctan \dfrac{\rho_W \sin(-2\pi f_F TE_n)}{\rho_F + \rho_W \cos(-2\pi f_F TE_n)}$, k is an integer number and $k/\Delta TE$ wrap is caused by the limited dynamic range. The true field map can be written as $$b = \tilde{f} + k/\Delta TE - mf_F - \psi(TE_n, \rho_W, \rho_F). \quad [46]$$

where $m \in \{0, 1\}$, and the model error $\psi(TE_n, \rho_W, \rho_F)$ in the approximate solution is $$\psi(TE_n, \rho_W, \rho_F) = \begin{cases} \dfrac{\sum_{n=1}^{N} a^2(TE_n) TE_n \theta(TE_n)}{\sum_{n=1}^{N} 2a^2(TE_n) \pi TE_n^2}, & |\rho_W| \geq |\rho_F| \\ \dfrac{\sum_{n=1}^{N} a^2(TE_n) TE_n \theta'(TE_n)}{\sum_{n=1}^{N} 2a^2(TE_n) \pi TE_n^2}, & |\rho_W| < |\rho_F| \end{cases} \quad [47]$$

Assuming the actual field map $f_s$ is spatially continuous and the model error is small compared to phase wraps or chemical shifts, appropriate k and m needs to be found to address the discontinuities in $\tilde{f}$ $$k^*, m^* = \arg\min_{k,m} \|\nabla \tilde{f}_s\|_2^2 = \arg\min_{k,m} \|\nabla (\tilde{f} + k/\Delta TE - mf_F)\|_2^2 \quad [48]$$

where $\nabla$ denotes the gradient operator. This joint optimization over k and m can be efficiently solved using graph cuts with conditional jump moves. The model error in field map $\tilde{f}_s$ is bounded by $\psi(TE_n, \rho_W, \rho_F)$. From the approximate solution of $\psi(TE_n, \rho_W, \rho_F)$, we find a greater last echo $TE_N$ leads to a smaller fitting error. In addition, $\psi(TE_n, \rho_W, \rho_F) = 0$ if $\rho_W = 0$ or $\rho_F = 0$. That is, if the voxels consist of pure water or pure fat, the model error of the fitting is zero. The true model error introduced in the single species fitting will be calculated in numerical simulation detailed in the methods section. It is verified that the true model error also decreases with increasing $TE_N$ and the model error $\psi(TE_n, \rho_W, \rho_F)$ is less than 15 Hz when $TE_N$ is larger than 17.6 ms, and the average error size is 2.67 Hz. Therefore, the above simultaneous phase unwrapping and chemical shift result b can be used as a good initial guess for IDEAL.

The above result was used in the above Eq.43 signal fitting to obtain water map and fat map. This simultaneous phase unwrapping and chemical shift determination based on graph cuts was used to initialize an iterative chemical shift update method to remove chemical shift from fat.

Background Field and Dipole Inversion:

Since the T2 of lung is very short, there are usually no reliable signals from lung in GRE images. Thus, the myocardium of the heart is right next to region with no reliable signals, i.e. region with sources that generated background field. Current state of the art methods for removing or compensating for background field generally produce error in edges through either over estimation of background field, or erosion. To ensure an accurate suppression of the effect from background field in the final QSM, we used the Total Field Inversion method:

$$\chi^* = \arg\min_\chi \frac{1}{2} \|w(b - d^* P\chi)\|_2^2 + \lambda \|M_G \nabla P\chi\|_1 \quad [49]$$

Where $\chi$ is the susceptibility map in the whole FOV, b is the total field generated by susceptibility estimated from the above fat-water decomposition, including susceptibility sources from tissue of interest and from background, d is the dipole kernel, $\nabla$ is a gradient operator, $\lambda$ is the regularization parameter, $M_G$ is the edge mask, and w is a SNR weighting. P is a preconditioner that increases the convergence speed of the algorithm. The preconditioner is a binary mask with 1 inside ROI and a larger value outside ROI. The outside value of P was empirically chosen to be 30.

8.3. Results

Three of the five volunteers were able to perform adequate consistent breath holds for successful 2DBH QSM. In comparison, 3DNAV was successfully acquired on all five volunteers, and image quality of cardiac QSM from 3DNAV was consistently better than that from 2DBH on every subject.

Figure 42:
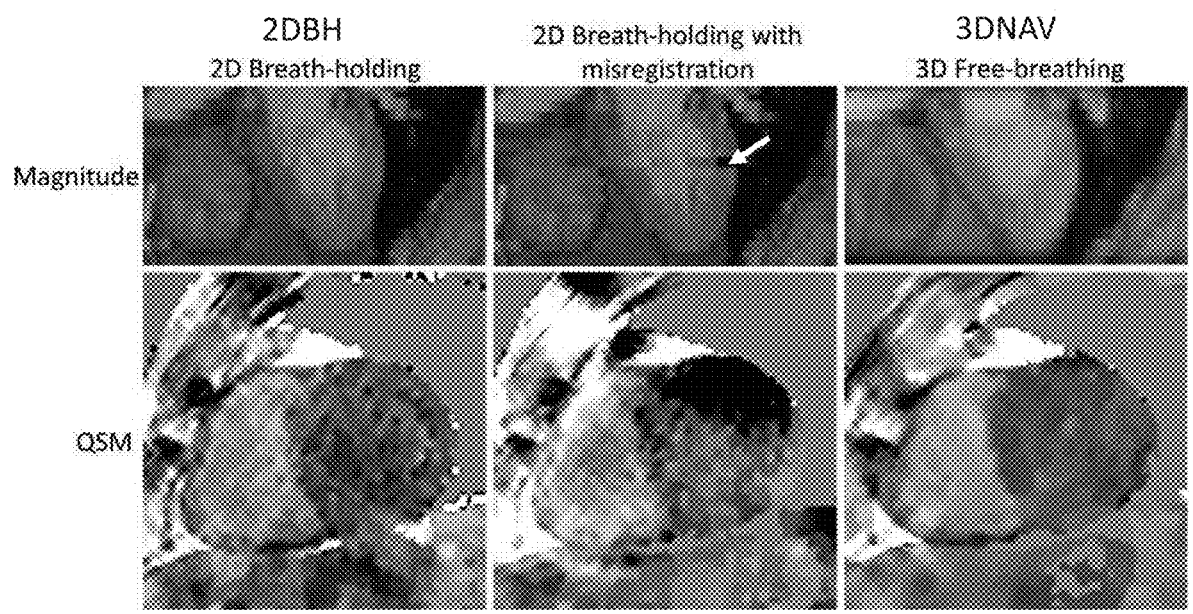
FIG. 42. QSM from 2DBH approach has similar RV to LV contrast as the QSM from 3DNAV approach. When there was a misregistration error caused by inconsistent breath hold (as indicated by the arrow), then the resulting QSM had major artifacts and did not allow for reliable interpretation. The QSM from 2DBH appeared to be noisier than the QSM from 3DNAV, due to lower SNR in 2DBH than in 3DNAV.

As shown in FIG. 42, when all breath holds were consistent, the QSM from 2DBH approach has similar RV to LV contrast as the QSM from 3DNAV approach. When there was a misregistration error caused by inconsistent breath hold (as indicated by the arrow), then the resulting QSM had major artifacts and did not allow for reliable interpretation. The QSM from 2DBH appeared to be nosier than the QSM from 3DNAV, due to lower SNR in 2DBH than in 3DNAV.

The average susceptibility difference between right and left ventricular blood pools, measured from the 2DBH QSM on the three volunteers who were able to perform adequate consistent breath holds, was 270±18 ppb, which corresponded to an oxygenation level of 79.6±1.1%. The average susceptibility difference between right and left ventricular blood pools, measured from the 3DNAV QSM on the five volunteers, was 262±13 ppb, which was 80±1% SvO2.

8.4. Conclusions

Our preliminary data showed the impracticality of the 2DBH approach for cardiac QSM, which was limited by its vulnerability to inconsistent breath holds. To understand this vulnerability, we simulated a single slice misregistration by shifting one of the slice in the volume that was successfully acquired by 2DBH approach, and we found drastically increased artifacts in QSM output. Therefore, as few as a single slice misregistration can cause major artifacts in the resulting QSM. The 3DNAV approach eliminated the need of breath holds, and the resulting cardiac QSM was uniformly better than cardiac QSM from 2DBH, making the 3DNAV approach a more viable option in clinical environment.

In summary, 3D acquisition with free-breathing navigator gating is a promising cardiac QSM approach without breath hold inconsistency and efforts.

9. Device System Implementation

Figure 43:
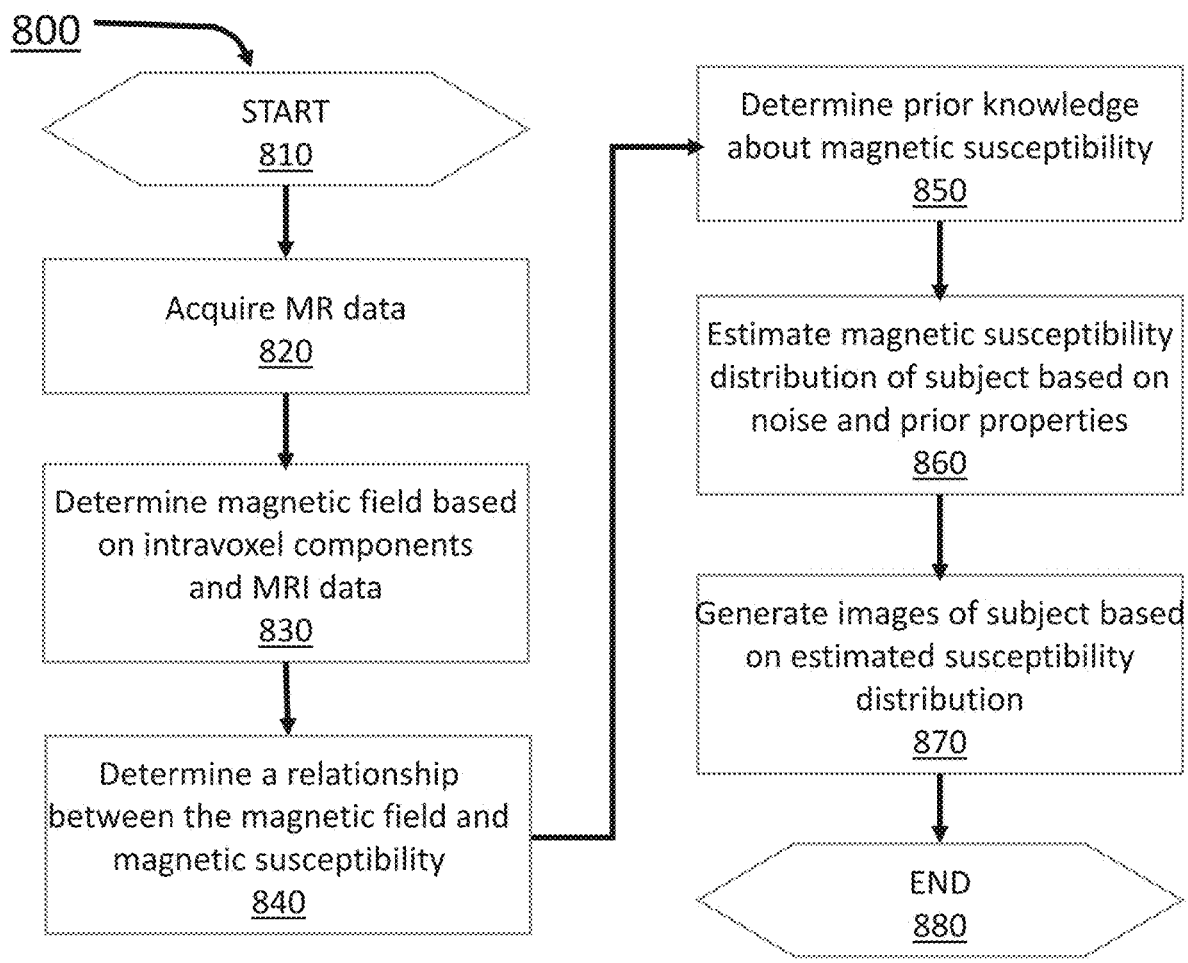
FIG. 43 shows an example process for mapping tissue magnetic susceptibility.
Figure 44:
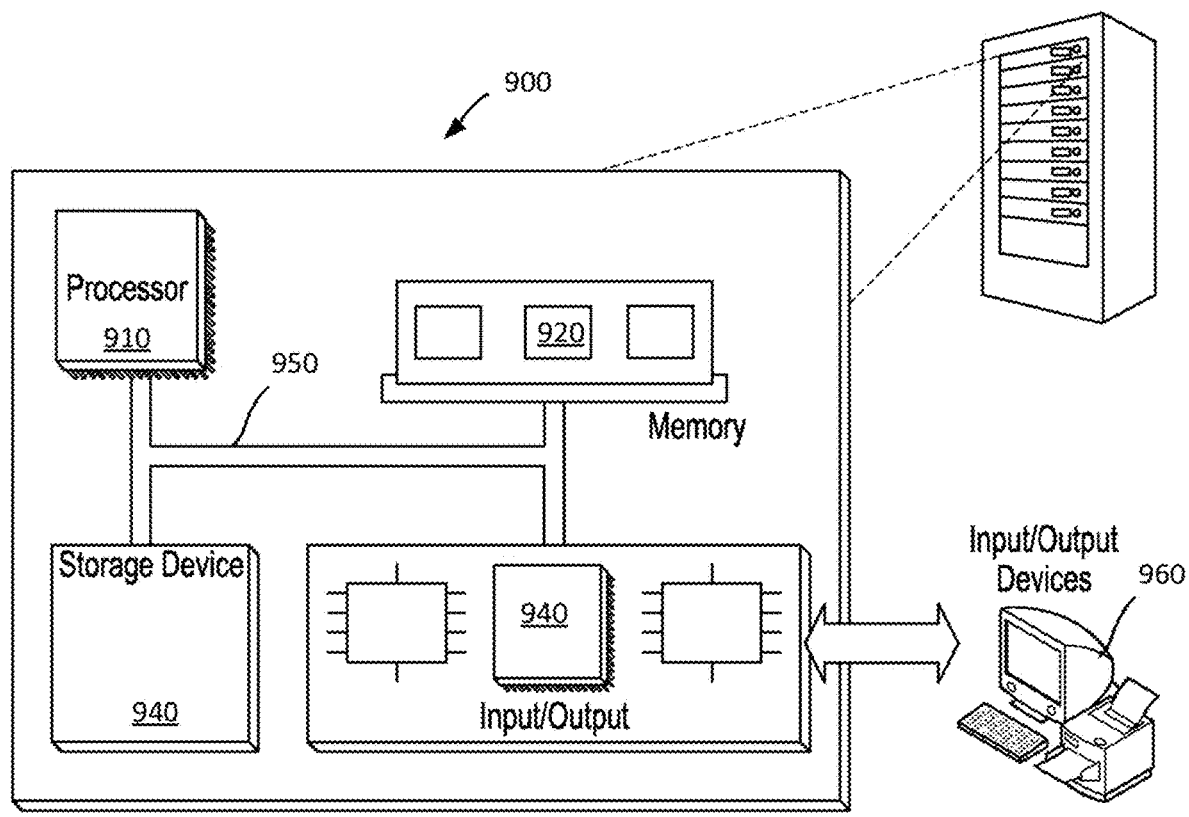
FIG. 44 is a block diagram of an example computer system.

In some cases, one or more of the above quantitative susceptibility mapping techniques can be implemented using the process 800 shown in FIG. 43. As an example, the process 800 can be used to map the tissue magnetic susceptibility of a subject, such as a patient (or portion of a patient) or an experimental sample (e.g., an imaging phantom, a sample of material or tissue, and so forth).

In some implementations, the process 800 can be used to transform MR signal data corresponding to a subject into susceptibility-based images that quantitatively depict the structure and/or composition of the subject. As an example, in some cases, the process 800 can be used to obtain MR data corresponding a subject, and process this MR data to generate a quantitative susceptibility map of the subject. Using this quantitative susceptibility map, one or more susceptibility-based images of the subject can be generated and displayed to a user. The user can then use these images for diagnostic or experimental purposes, for example to investigate the structure and/or composition and/or function of the subject, and/or to diagnose various conditions or diseases based, and/or to treat various conditions or diseases based, at least in part, on the images. As the process 800 can result in susceptibility-based images having higher quality and/or accuracy compared to other susceptibility mapping techniques, implementations of the process 800 can be used to improve a user's understanding of a subject's structure and/or composition and/or function, and can be used to improve the accuracy of any resulting medical diagnoses or experimental analyses.

The process 800 begins by acquiring magnetic resonance (MR) data corresponding to a subject (step 810). In some cases, the MR data can correspond to a patient (e.g., the entirety of a patient or a portion of a patient, such as a particular portion to the patient's body). In some cases, the MR data can correspond to one or more samples (e.g., an imaging phantom, a sample of one or more materials, a sample of one or more types of tissue, and/or one or more other objects).

In some implementations, the MR data can be acquired using an MRI scanner using one or more suitable pulse sequences. As an example, in some cases, MR data can be acquired using a gradient echo sequence that acquires MR data at a single echo time or at multiple echo times (e.g., two, three, four, five, and so forth). Various scan parameters can be used. As another example, MR data can be obtained using a 3D multi-echo spoiled gradient echo sequence on a 3T scanner (e.g., a GE Excite HD MR scanner) using a pulse sequence that samples at different echo times (TE) (e.g., 4 TEs, such as 3.8, 4.3, 6.3 and 16.3 ms) in an interleaved manner, and with following imaging parameters: repetition time (TR)=22 ms; voxel size=0.5×0.5×0.5 mm$^3$, matrix size=256×64×64; bandwidth (BW)=±31.25 kHz; flip angle=15°. As another example, MR data can be obtained using a 3D multi-gradient echo sequence on a 3T scanner using imaging parameters TE/ΔTE/#TE/TR/FA/BW/FOV/ matrix size=5 ms/5 ms/8/50 ms/20°/±62.50 kHz/21.8×24× 12.8 cm$^3$/232×256×64. Although an example sequences and example parameters are described above, these are merely illustrative. In practice, other sequences and parameters can be used, depending on various factors (e.g., the size of region to be examined, a known or assumed range of susceptibility values of the subject, scan time considerations, device limitations, and so forth).

After acquiring MR data corresponding to a subject, the process 800 continues by determining a magnetic field based on the MR data (step 820). As noted above, in some cases, the MRI signal phase is affected by the magnetic field corresponding to the magnetic susceptibility distribution of the subject and the chemical shift of tissue components.

The magnetic field can be determined from the complex MR data by fitting the detected signal as a sum over tissue spectral components, where each component signal characterized by an exponent with a negative real part representing signal decay and an imaginary part representing phase dependent on the magnetic field and the chemical shift (step 830). This fitting for such a complex signal model can be performed on iteratively using numerical optimization. A robust initialization for numerical optimization can be estimated using a simplified single species model and graph cut separating smooth field against chemical shift and phase unwrapping.

After determining the magnetic field based on the MR data, the process 800 continues by determining a relationship between the magnetic field and magnetic susceptibility (step 840). As described above, in some implementations, the relationship between the magnetic field and magnetic susceptibility can be expressed as a relationship between the magnetic field at a given location to the magnetic susceptibility at that location. In some cases, this relationship can be expressed in integral form, or in differential form. In the differential form, the relationship between the magnetic field at a given location to the magnetic susceptibility at that location can include an equation where a Laplacian of the magnetic field equals one third of the Laplacian of the magnetic susceptibility minus a second order derivative of the magnetic susceptibility.

After determining a relationship between the magnetic field and magnetic susceptibility, the process 800 continues by determining prior knowledge about tissue magnetic susceptibility distribution (step 850). One estimation of tissue susceptibility distribution is to use R2* values derived from the magnitude signal. High R2* values can be used to identify high susceptibility regions such as hemorrhages for preconditioning to accelerate the convergence of numerical optimization. An example of preconditioning is to separate the whole image volume into region with high susceptibility (including hemorrhages, air regions and background) and region with normal tissue susceptibility. Such preconditioning reduces the susceptibility search range and hence accelerates convergence. Another estimation of tissue susceptibility distribution is to use low (near zero) R2* regions for identifying regions of pure water such as cerebrospinal fluid in the ventricles in the brain, oxygenated arterial blood in the aorta, or regions of pure fat in the abdominal wall. As water and fat have known susceptibility values, they can be used to serve zero references (to water) to generate absolute susceptibility values using a minimal variance regularization.

After obtaining the susceptibility prior information and signal data noise property, the process 800 continues by estimating a magnetic susceptibility distribution of the subject based, at least in part, on the prior information and data noise property (step 860). As described above, estimating the susceptibility distribution of the subject can include determining a cost function corresponding to a susceptibility distribution, the magnetic field, masks corresponding to regions of interest. The cost function includes a data fidelity term based on data noise property expressing the relationship between the magnetic field and tissue susceptibility in an integral or differential form, and a regularization term expressing prior information. The estimated susceptibility distribution of the subject can be determined by identifying a particular susceptibility distribution that minimizes one or more of these cost functions. As described above, in some cases, this can be determined numerically.

After estimating a magnetic susceptibility distribution of the subject, the process 800 continues by generating one or more images of the subject based on the estimated susceptibility distribution of the subject (step 870). These images can be electronically displayed on a suitable display device (e.g., an LCD display device, LED display device, CRT display device, or other display device that can be configured to show images) and/or physically displayed on a suitable medium (e.g., printed, etched, painted, imprinted, or otherwise physically presented on a sheet or paper, plastic, or other material).

In some cases, the estimated susceptibility distribution of the subject can be visualized using a color scale, where each of several colors is mapped to a particular susceptibility value or range of susceptibility values. Accordingly, a two dimensional or three dimension image can be generated, where each pixel or voxel of the image corresponds to a particular spatial location of the subject, and the color of that pixel of voxel depicts the susceptibility value of the subject at that location.

In some cases, the color scale can include a gradient of colors and/or a gradient of gray shades (e.g., a gray scale), in order to depict a range of susceptibility values. In some cases, for a color scale that includes a gradient of colors or a gradient of gray shades, one end of the gradient can correspond to the lowest susceptibility value in a particular window of susceptibility values (e.g., an arbitrarily selected window of values), and the other end of the gradient can correspond to the highest susceptibility value in the window of values. For instance, for gray scale that includes a gradient of gray shades between pure white and pure black, pure white can be used to indicate the highest susceptibility value in a particular arbitrary window of values, and pure black can be used to indicate the lowest susceptibility value in the window of values. Other relationships between a color/gray scale and susceptibility values is also possible. For example, in some cases, for gray scale that includes a gradient of gray shades between pure white and pure black, pure white can be used to indicate the lower susceptibility value in a particular arbitrary window of values, and pure black can be used to indicate the highest susceptibility value in the window of values. Although the examples are described in the context of gray scales, in practice, similar relationships between color scales and susceptibility values are also possible.

Susceptibility values and colors can be mapped linearly (e.g., such that each absolute change in susceptibility value corresponds to a proportional change in color), logarithmically (e.g., such that each an exponential changes in susceptibility values correspond to a linear change in color), or according to any other mapping. Although examples mapping between color scales and susceptibility values are described above, these are merely illustrative examples. In practice, other mappings are also possible, depending on the implementation.

In some cases, the estimated susceptibility distribution can be regularized based on prior information regarding the subject. As an example, the estimated susceptibility distribution can regularized using one or more of the techniques described above. In some cases, regularizing the estimated susceptibility distribution based on prior information regarding the subject comprises determining boundary conditions associated with the subject.

Implementations of the above described techniques can be performed using a computer system. FIG. 43 is a block diagram of an example computer system 900 that can be used, for example, to perform implementations of the process 800. In some implementations, the computer system 900 can be communicatively connected to another computer system (e.g., another computer system 900), such that it receives data (e.g., MRI datasets), and analyzes the received data using one or more of the techniques described above.

The system 900 includes a processor 910, a memory 920, a storage device 930, and an input/output device 940. Each of the components 910, 920, 930, and 940 can be interconnected, for example, using a system bus 950. The processor 910 is capable of processing instructions for execution within the system 900. In some implementations, the processor 910 is a single-threaded processor. In some implementations, the processor 910 is a multi-threaded processor. In some implementations, the processor 910 is a quantum computer. The processor 910 is capable of processing instructions stored in the memory 920 or on the storage device 930. The processor 910 may execute operations such as performing one or more of the techniques described above.

The memory 920 stores information within the system 900. In some implementations, the memory 920 is a computer-readable medium. In some implementations, the memory 920 is a volatile memory unit. In some implementations, the memory 920 is a non-volatile memory unit.

The storage device 930 is capable of providing mass storage for the system 900. In some implementations, the storage device 930 is a non-transitory computer-readable medium. In various different implementations, the storage device 930 can include, for example, a hard disk device, an optical disk device, a solid-state drive, a flash drive, magnetic tape, or some other large capacity storage device. In some implementations, the storage device 930 may be a cloud storage device, e.g., a logical storage device including multiple physical storage devices distributed on a network and accessed using a network. In some examples, the storage device may store long-term data. The input/output device 940 provides input/output operations for the system 900. In some implementations, the input/output device 940 can include one or more of a network interface devices, e.g., an Ethernet card, a serial communication device, e.g., an RS-232 port, and/or a wireless interface device, e.g., an 802.11 card, a 3G wireless modem, a 4G wireless modem, etc. A network interface device allows the system 900 to communicate, for example, transmit and receive data. In some implementations, the input/output device can include driver devices configured to receive input data and send output data to other input/output devices, e.g., a keyboard, a mouse, a printer, a sensor (e.g., a sensor that measures component or system-related properties, a sensor that measures environmental-related properties, or other types of sensors), and a display device 960. In some implementations, mobile computing devices, mobile communication devices, and other devices can be used.

A computing system can be realized by instructions that upon execution cause one or more processing devices to carry out the processes and functions described above, for example, storing, maintaining, and displaying artifacts. Such instructions can include, for example, interpreted instructions such as script instructions, or executable code, or other instructions stored in a computer readable medium. A computing system can be distributively implemented over a network, such as a server farm, or a set of widely distributed servers or can be implemented in a single virtual device that includes multiple distributed devices that operate in coordination with one another. For example, one of the devices can control the other devices, or the devices may operate under a set of coordinated rules or protocols, or the devices may be coordinated in another fashion. The coordinated operation of the multiple distributed devices presents the appearance of operating as a single device.

Although an example processing system has been described in FIG. 43, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as performing one or more of the above described processes, can be implemented as one or more computer program products, e.g., one or more modules of computer program instructions encoded on a tangible program carrier, for example a computer-readable medium, for execution by, or to control the operation of, a processing system. The computer readable medium can be a machine readable storage device, a machine readable storage substrate, a memory, device, a composition of matter effecting a machine readable propagated signal, or a combination of one or more of them.

The term "processing module" may encompass all apparatus, devices, and machines for processing data, including by way of example a programmable processor, a computer, or multiple processors or computers. A processing module can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. Sometimes a server is a general purpose computer, and sometimes it is a custom-tailored special purpose electronic device, and sometimes it is a combination of these things. Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication; e.g., a communication network. Examples of communication networks include a local area network ("LAN") and a wide area network ("WAN"), e.g., the Internet.

Certain features that are described above in the context of separate implementations can also be implemented in combination in a single implementation. Conversely, features that are described in the context of a single implementation can be implemented in multiple implementations separately or in any sub-combinations.

The order in which operations are performed as described above can be altered. In certain circumstances, multitasking and parallel processing may be advantageous. The separation of system components in the implementations described above should not be understood as requiring such separation.

A number of embodiments of the invention have been described. Nevertheless, it will be understood that various modifications may be made without departing from the spirit and scope of the disclosure. Accordingly, other embodiments are within the scope of the following claims.

What is claimed is:

1. A method for generating one or more images of an object, the method comprising:
receiving magnetic resonance imaging (MRI) data obtained by a magnetic resonance scanner, wherein the MRI data is complex and comprises magnitude and phase information or real and imaginary information regarding tissue in the object, and Gaussian noise;
calculating a magnetic field experienced by the tissue in the object based on modeling the complex MRI data according to tissue composition;
identifying a region of interest in the tissue that has an approximately uniform susceptibility according to a characteristic feature, wherein the characteristic feature is low R2* value and the region of interest is determined by applying R2* thresholding and connectivity;
estimating a magnetic susceptibility distribution of the object based on the calculated magnetic field, wherein estimating the magnetic susceptibility distribution of the subject comprises:
determining a cost function, the cost function relating at least a data fidelity term associated with a likelihood function of the Gaussian noise in the MRI data, a first regularization term associated with a structure prior information, and a second regularization term associated with enforcing the approximately uniform susceptibility in the region of interest in the tissue; and
determining a magnetic susceptibility distribution based on minimizing the cost function; and
outputting, to a display device or to a storage device, one or more images of the object generated based on the determined magnetic susceptibility distribution.

2. The method of claim 1, wherein the tissue for the region of interest with an approximately uniform susceptibility is selected from: cerebrospinal fluid, blood, soft tissue, muscle, or fat.

3. The method of claim 1, wherein a susceptibility value for the region of interest with an approximately uniform susceptibility is known and is used as a reference value for the susceptibility distribution.

4. The method of claim 1, wherein the minimizing of the cost function involves preconditioning.

5. The method of claim 1, wherein tissue composition consists of fat and water, and the calculated magnetic field, a water fraction and a fat fraction in a voxel are computed iteratively from the complex MRI data using an appropriate initialization.

6. The method of claim 5, wherein an initialization for the iterative computation is determined using simultaneous phase unwrapping and chemical shift determination based on graph cuts or using in-phase echoes.

7. The method of claim 1, wherein a quantitative biomaterial map is generated to depict iron by correcting for a fat contribution to the magnetic susceptibility distribution, or to depict fibrosis by correcting for iron contribution to R2*, or to depict bone mineral by utilizing the MRI data with short TE and modeling the MRI data with a bone-specific R2*.

8. The method of claim 1, wherein tissue oxygen extraction fraction map is generated by including a model of MRI data magnitude dependence on deoxyheme concentration.

9. The method of claim 8, wherein the generation of the tissue oxygen extraction fraction map makes use of a similar signal behavior among voxels.

10. A system for generating one or more images of an object, the system comprising:
a processor;
a display device communicatively coupled to the processor;
an Input/Output (I/O) device communicatively coupled to the processor;
a non-transitory computer storage medium encoded with a computer program, the program comprising instructions that when executed by the processor cause the processor to perform operations comprising:
receiving magnetic resonance imaging (MRI) data obtained by a magnetic resonance scanner, wherein the MRI data is complex and comprises magnitude and phase information or real and imaginary information regarding tissue in the object, and Gaussian noise;
calculating a magnetic field experienced by the tissue in the object based on modeling the complex MRI data according to tissue composition;
identifying a region of interest in the tissue that has an approximately uniform susceptibility according to a characteristic feature, wherein the characteristic feature is low R2* value and the region of interest is determined by applying R2* thresholding and connectivity;
estimating a magnetic susceptibility distribution of the object based on the calculated magnetic field, wherein estimating the magnetic susceptibility distribution of the subject comprises:
determining a cost function, the cost function relating at least a data fidelity term associated with a likelihood function of the Gaussian noise in the MRI data, a first regularization term associated with a structure prior information, and a second regularization term associated with enforcing the approximately uniform susceptibility in the region of interest in the tissue; and
determining a magnetic susceptibility distribution based on minimizing the cost function; and
presenting, on the display device, one or more images of the object generated based on the determined magnetic susceptibility distribution.

11. The system of claim 10, wherein the tissue for the region of interest with an approximately uniform susceptibility is selected from: cerebrospinal fluid, blood, soft tissue, muscle, or fat.

12. The system of claim 10, wherein a susceptibility value for the region of interest with an approximately uniform susceptibility is known and is used as a reference value for the susceptibility distribution.

13. The system of claim 10, wherein the minimizing of the cost function involves preconditioning.

14. The system of claim 10, wherein the object comprises one or more of a cortex, a putamen, a globus pallidus, a red nucleus, a substantia nigra, and a subthalamic nucleus of a brain, or a liver in an abdomen, or a heart in a chest, or a bone in a body, or a lesion of diseased tissue.

15. The system of claim 10, wherein tissue composition consists of fat and water, and the calculated magnetic field, a water fraction and a fat fraction in a voxel are computed iteratively from the complex MRI data using an appropriate initialization.

16. The system of claim 15, wherein an initialization for the iterative computation is determined using simultaneous phase unwrapping and chemical shift determination based on graph cuts or in-phase echoes.

17. The system of claim 10, wherein a quantitative biomaterial map is generated to depict iron by correcting for a fat contribution to the magnetic susceptibility distribution, or to depict fibrosis by correcting for iron contribution to R2*, or to depict bone mineral by utilizing the MRI data with short TE and modeling the MRI data with a bone-specific R2*.

18. The system of claim 10, wherein tissue oxygen extraction fraction map is generated by including a model of MRI data magnitude dependence on deoxyheme concentration.

19. The system of claim 18, wherein the generation of the tissue oxygen extraction fraction map makes use of a similar signal behavior among voxels.

20. A method for generating one or more images of an object, the method comprising:
- receiving magnetic resonance imaging (MRI) data obtained by a magnetic resonance scanner, wherein the MRI data is complex and comprises magnitude and phase information or real and imaginary information regarding tissue in the object, and Gaussian noise;
- calculating a magnetic field experienced by the tissue in the object based on modeling the complex MRI data according to tissue composition;
- identifying a region of interest in the tissue that has an approximately uniform susceptibility according to a characteristic feature, wherein the characteristic feature is low R2* value;
- estimating a magnetic susceptibility distribution of the object based on the calculated magnetic field, wherein estimating the magnetic susceptibility distribution of the subject comprises:
  - determining a cost function, the cost function relating at least a data fidelity term associated with a likelihood function of the Gaussian noise in the MRI data, a first regularization term associated with a structure prior information, and a second regularization term associated with enforcing the approximately uniform susceptibility in the region of interest in the tissue; and
  - determining a magnetic susceptibility distribution based on minimizing the cost function; and
- outputting, to a display device or to a storage device, one or more images of the object generated based on the determined magnetic susceptibility distribution.

* * * * *